United States Patent
Bachovchin et al.

(10) Patent No.: US 9,956,297 B2
(45) Date of Patent: *May 1, 2018

(54) FAP-ACTIVATED PROTEASOME INHIBITORS FOR TREATING SOLID TUMORS

(71) Applicant: Trustees of Tufts College, Boston, MA (US)

(72) Inventors: William W. Bachovchin, Cambridge, MA (US); Hung-sen Lai, Andover, MA (US); Sarah E. Poplawski, Belmont, MA (US)

(73) Assignee: Trustees of Tufts College, Boston, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/167,109

(22) Filed: May 27, 2016

(65) Prior Publication Data

US 2016/0346401 A1    Dec. 1, 2016

Related U.S. Application Data

(63) Continuation of application No. 14/241,666, filed as application No. PCT/US2012/053140 on Aug. 30, 2012, now Pat. No. 9,597,410.

(60) Provisional application No. 61/528,824, filed on Aug. 30, 2011.

(51) Int. Cl.
| | |
|---|---|
| A61K 31/69 | (2006.01) |
| A61K 47/48 | (2006.01) |
| A61K 45/06 | (2006.01) |
| G01N 33/574 | (2006.01) |
| C07K 5/083 | (2006.01) |
| C07K 5/087 | (2006.01) |
| C07K 5/097 | (2006.01) |
| C07K 5/107 | (2006.01) |
| C07K 5/065 | (2006.01) |
| C07K 5/062 | (2006.01) |
| A61K 38/07 | (2006.01) |
| A61K 47/54 | (2017.01) |
| A61K 38/00 | (2006.01) |

(52) U.S. Cl.
CPC ........ *A61K 47/48361* (2013.01); *A61K 31/69* (2013.01); *A61K 38/07* (2013.01); *A61K 45/06* (2013.01); *A61K 47/54* (2017.08); *C07K 5/06026* (2013.01); *C07K 5/06034* (2013.01); *C07K 5/06078* (2013.01); *C07K 5/081* (2013.01); *C07K 5/0806* (2013.01); *C07K 5/0808* (2013.01); *C07K 5/0812* (2013.01); *C07K 5/0821* (2013.01); *C07K 5/1016* (2013.01); *G01N 33/574* (2013.01); *A61K 38/00* (2013.01)

(58) Field of Classification Search
None
See application file for complete search history.

(56) References Cited

U.S. PATENT DOCUMENTS

| | | |
|---|---|---|
| 4,499,082 A | 2/1985 | Shenvi et al. |
| 4,935,493 A | 6/1990 | Bachovchin et al. |
| 5,462,928 A | 10/1995 | Bachovchin et al. |
| 5,580,979 A | 12/1996 | Bachovchin |
| 5,776,902 A | 7/1998 | Bachovchin |
| 6,180,402 B1 | 1/2001 | Granville et al. |
| 6,227,818 B1 | 5/2001 | Falk et al. |
| 6,258,597 B1 | 7/2001 | Bachovchin et al. |
| 6,300,314 B1 | 10/2001 | Wallner et al. |
| 6,355,614 B1 | 3/2002 | Wallner |
| 6,703,238 B2 | 3/2004 | Bachovchin et al. |
| 6,770,628 B2 | 8/2004 | Wallner et al. |
| 6,803,357 B1 | 10/2004 | Bachovchin et al. |
| 6,825,169 B1 | 11/2004 | Bachovchin et al. |
| 6,890,898 B2 | 5/2005 | Bachovchin et al. |
| 6,890,904 B1 | 5/2005 | Wallner et al. |
| 6,949,514 B2 | 9/2005 | Wallner et al. |
| 6,979,697 B1 | 12/2005 | Wallner |
| 7,276,371 B2 | 10/2007 | Bachovchin et al. |
| 7,282,484 B2 | 10/2007 | Wallner et al. |
| 7,399,869 B2 | 7/2008 | Cohen et al. |

(Continued)

FOREIGN PATENT DOCUMENTS

| | | |
|---|---|---|
| AU | 2003228793 A1 | 11/2003 |
| CA | 2484551 A1 | 11/2003 |

(Continued)

OTHER PUBLICATIONS

Milo, L. J. et al., "Chemical and Biological Evaluation of Dipeptidyl Boronic Acid Proteasome Inhibitors for Use in Prodrugs and Pro-Soft Drugs Targeting Solid Tumors", *J. Med. Chem.*, 54:4365-4377 (American Chemical Society, USA, 2011).

(Continued)

*Primary Examiner* — Karlheinz R. Skowronek
*Assistant Examiner* — Ronald T Niebauer
(74) *Attorney, Agent, or Firm* — Foley Hoag LLP

(57) ABSTRACT

Disclosed are proteasome inhibitors, fibroblast activation protein (FAP)-activated prodrugs of proteasome inhibitors, and pharmaceutically acceptable salts of the inhibitors and prodrugs. Also disclosed are related pharmaceutical compositions, and methods of using the inhibitors and prodrugs and compositions thereof, for example, in treating cancer or other cell proliferative diseases. In vitro and in vivo methods of quantifying the expression of FAP in a biopsy sample and a mammal, respectively, are also disclosed.

18 Claims, 34 Drawing Sheets

(56) References Cited

U.S. PATENT DOCUMENTS

| | | | |
|---|---|---|---|
| 7,691,967 | B2 | 4/2010 | Bachovchin |
| 9,597,410 | B2 * | 3/2017 | Bachovchin ............ A61K 31/69 |
| 2003/0153509 | A1 | 8/2003 | Bachovchin et al. |
| 2003/0158114 | A1 | 8/2003 | Wallner et al. |
| 2004/0077601 | A1 | 4/2004 | Adams et al. |
| 2004/0152192 | A1 | 8/2004 | Bachovchin et al. |
| 2004/0176307 | A1 | 9/2004 | Bachovchin et al. |
| 2004/0229820 | A1 | 11/2004 | Bachovchin et al. |
| 2005/0037976 | A1 | 2/2005 | Wallner et al. |
| 2005/0049177 | A1 | 3/2005 | Bachovchin et al. |
| 2005/0070459 | A1 | 3/2005 | Bachovchin et al. |
| 2005/0070482 | A1 | 3/2005 | Bachovchin |
| 2005/0084490 | A1 | 4/2005 | Adams et al. |
| 2005/0203027 | A1 | 9/2005 | Bachovchin et al. |
| 2005/0272703 | A1 | 12/2005 | Wallner et al. |
| 2006/0052310 | A1 | 3/2006 | Wallner |
| 2006/0063719 | A1 | 3/2006 | Jesson et al. |
| 2006/0089312 | A1 | 4/2006 | Bachovchin |
| 2006/0287245 | A1 | 12/2006 | Wallner et al. |
| 2010/0168032 | A1 | 7/2010 | Bachovchin |
| 2010/0184706 | A1 * | 7/2010 | Bachovchin ............ A61K 47/64 514/1.1 |
| 2011/0014125 | A1 | 1/2011 | Bossmann et al. |
| 2013/0303435 | A1 | 11/2013 | Bachovchin |

FOREIGN PATENT DOCUMENTS

| | | |
|---|---|---|
| EP | 0 195 212 A2 | 9/1986 |
| EP | 1499336 A2 | 1/2005 |
| EP | 2204181 A2 | 7/2010 |
| EP | 2319523 A1 | 5/2011 |
| JP | 2004-500790 A | 1/2004 |
| JP | 2012-211523 A | 11/2012 |
| WO | WO-89/03223 A1 | 4/1989 |
| WO | WO-2003/092605 A2 | 11/2003 |
| WO | WO-2008/116054 A1 | 9/2008 |
| WO | WO 2009/006473 * | 1/2009 |
| WO | WO-2009/006473 A3 | 1/2009 |

OTHER PUBLICATIONS

Warnecke, A. et al., "2,4-Bis(hydroxmethyl)aniline as a Building Block for Oligomers with Self-Eliminating and Multiple Release Properties", *J. Org. Chem.*, 73:1546-1552 (American Chemical Society, USA, 2008).

International Search Report and Written Opinion from parent PCT application PCT/US2012/053140 dated Nov. 2, 2012.

Extended European Search Report from corresponding European regional application EP12827686.2 dated May 29, 2015.

Bachovchin, et al., "Inhibition of IgA1 Proteinases from Neisseria gonorrhoeae and Hemophilus influenzae by Peptide Prolyl Boronic Acids," J. Biol. Chem., 265(7):3738-3743 (1990).

Gao, et al., "Direct Selection for Catalysis from Cobinatorial Antibody Libraries Using a Boronic Acid Probe: Primary Amide Bond Hydrolysis," J. Am. Chem. Soc., 120(10):2211-2217 (1998).

Tsilikounas et al., "B NMR Spectroscopy of Peptide Boronic Acid Inhibitor Complexes of α-Lytic Protease. Direct Evidence for Tetrahedral Boron in both Boron-Histidine and Boron-Serine Adduct Complexes," Biochemistry, 32:12651-12655 (1993).

European Search Report dated Apr. 1, 2011 from EP 10 01 1375.

European Search Report for EP 09 01 2951 dated Aug. 16, 2010.

* cited by examiner

Gemcitabine

* Gemcitabine is the current standard of care for pancreatic cancer

| Agent | Tumor conc. / Liver conc. |
|---|---|
| Velcade® | 0.11 |
| ARI-3996 | 0.26 |
| ARI-2727D | 3.5 |

Figure 27

| Tissue Source | Tissue Spec No. | Serum Barcode | FAP Activity (ΔFL/min/mg protein) | |
|---|---|---|---|---|
| | | | Tissue | Serum |
| Bladder | 1007526 | 113388 | 1969 | 50 |
| Bladder | 1005013 | 106958 | 1182 | 33 |
| Bladder | 1005636 | 109017 | 474 | 42 |
| Bladder | 1006129 | 110335 | 4104 | 68 |
| Bladder | 1007027 | 110340 | 1847 | 87 |
| Breast | 1005395 | 108343 | 98 | 85 |
| Breast | 1005451 | 108499 | 1598 | 59 |
| Breast | 1008772 | 112035 | 1648 | 65 |
| Breast | 1009328 | 118686 | 1073 | 57 |
| Breast | 1009649 | 119507 | 360 | 64 |
| Colon | 1006685 | 111639 | 643 | 50 |
| Colon | 1006857 | 112000 | 1413 | 74 |
| Colon | 1006879 | 112112 | 1988 | 46 |
| Colon | 1007172 | 112887 | 569 | 45 |
| Colon | 1007407 | 113270 | 835 | 45 |
| Lung | 1009959 | 120228 | 118 | 56 |
| Lung | 1010842 | 122636 | 1374 | 55 |
| Lung | 1010756 | 122466 | 104 | 53 |
| Lung | 1009309 | 117908 | 313 | 58 |
| Lung | 1010231 | 120826 | 135 | 46 |

Figure 27 (Continued)

| Tissue Source | Tissue Spec No. | Serum Barcode | FAP Activity (ΔFL/min/mg protein) | |
|---|---|---|---|---|
| | | | Tissue | Serum |
| Ovary | 1005120 | 107660 | 5241 | 90 |
| Ovary | 1005431 | 108462 | 9 | 94 |
| Ovary | 1005817 | 109521 | 345 | 96 |
| Ovary | 1005896 | 109675 | 42 | 46 |
| Ovary | 1006594 | 111511 | 588 | 63 |
| Renal | 1005560 | 108834 | 29 | 56 |
| Renal | 1009391 | 118759 | 553 | 31 |
| Renal | 1009454 | 118987 | 471 | 52 |
| Renal | 1009526 | 119039 | 53 | 51 |
| Renal | 1009522 | 119183 | 101 | 35 |
| Sarcoma | 1005042 | 107420 | 309 | 59 |
| Sarcoma | 1005118 | 107612 | 21 | 117 |
| Sarcoma | 1005228 | 107876 | 1982 | 69 |
| Sarcoma | 1005746 | 109227 | 353 | 61 |
| Sarcoma | 1005744 | 109270 | 302 | 68 |
| Uterine | 1006279 | 110607 | 1840 | 46 |
| Uterine | 1010225 | 120790 | 1325 | 37 |
| Uterine | 1008368 | 116201 | 780 | 67 |
| Uterine | 1008591 | 116699 | 1606 | 75 |
| Uterine | 1009314 | 118623 | 230 | 61 |

Figure 27 (Continued)

| | FAP Activity (ΔFL/min/mg protein) | | | | | | |
|---|---|---|---|---|---|---|---|
| | Pancreatic Tissue | | Plasma | | | | |
| Sample ID | Normal | Tumor | Baseline | Pre-Op Labs | Pre-Surgery | Immediate Post-Follow Up | Follow Up |
| NWL-001 | 393 | 57 | | 48 | 46 | 40 | 31 |
| M-V-002 | 74 | 6700 | 34 | | 38 | 35 | 32 |
| E-G-003 | | | 35 | | 38 | 35 | 44 |
| HSB-004 | | | | 40 | 41 | | |
| L-K-005 | | | | 41 | 41 | | |
| NAB-006 | 2181 | 9878 | 75 | | 65 | 71 | 129 |
| HJM-007 | 21 | 16528 | 65 | | 69 | 53 | 61 |
| BFM-008 | 105 | 2726 | 29 | | 32 | 21 | 23 |
| JLG-009 | | | 49 | | 43 | | |
| DLE-010 | 216 | 85 | 49 | | 42 | 41 | 26 |
| JLS-011 | 223 | 5400 | 71 | | 69 | 71 | 54 |
| JRP-012 | | | 49 | | 50 | | |
| JEP-013 | 22 | 2713 | 36 | 30 | 27 | 18 | |
| G-F-014 | | | 35 | | 32 | 28 | 35 |
| GAA-015 | 553 | 319 | 69 | | 71 | 43 | 75 |
| R-H-016 | | | 27 | | | 22 | 30 |
| S-S-017 | 1818 | | 56 | | 55 | 41 | 49 |
| RJS-018 | 1266 | 1678 | 32 | | 31 | 21 | |
| D-T-019 | | | 28 | | 22 | | |
| S-M-020 | | 7428 | 32 | | 31 | 26 | 48 |
| CEB-021 | 806 | 3430 | 51 | | 50 | 35 | 52 |
| KDW-022 | 340 | 7083 | 43 | | 40 | 41 | 39 |
| E-P-023 | 5289 | 4788 | 49 | | 45 | 40 | 33 |
| R-P-024 | 1773 | 6972 | 61 | | 57 | 47 | 44 |

FAP-ACTIVATED PROTEASOME INHIBITORS FOR TREATING SOLID TUMORS

RELATED APPLICATIONS

This application is a Continuation of U.S. patent application Ser. No. 14/241,666, filed May 19, 2014, which is the U.S. national phase of International Patent Application No. PCT/US2012/053140, filed Aug. 30, 2012, which claims the benefit of priority to U.S. Provisional Patent Application Ser. No. 61/528,824, filed Aug. 30, 2011, the entirety of each of which is incorporated herein by reference.

GOVERNMENT SUPPORT

This invention was made with government support under grant CA156930 awarded by the National Institutes of Health. The government has certain rights in the invention.

BACKGROUND OF THE INVENTION

One in four deaths in the USA is due to cancer, the second leading cause of death after heart disease. Lung cancer is the leading cause of mortality among cancers, and the majority of patients have locally advanced or metastatic non-small cell lung cancer (NSCLC) at the time of diagnosis. In women, breast cancer is the most prevalent cancer and is the second leading cause of cancer-related death.

The current standard of care for treatment of solid cancers has limited efficacy. For instance, in NSCLC survival remains poor despite improvements achieved by addition of targeted agents to first-line platinum-based chemotherapy. In metastatic breast cancer the efficacy of trastuzumab is limited by tumor resistance. When NSCLC progresses after first-line therapy, approved second-line agents only achieve modest survival rates.

More effective anticancer agents are clearly needed. Many approved cancer drugs, such as bortezomib (Velcade®), are cytotoxic agents that kill normal cells as well as tumor cells. The therapeutic benefit of these drugs depends on tumor cells being more sensitive than normal cells, thereby allowing clinical responses to be achieved at relatively safe drug doses; however, damage to normal tissues is unavoidable and often limits treatment. Following the success of bortezomib in treating multiple myeloma (MM), inhibition of the proteasome complex emerged as a promising new approach to chemotherapy. Due to its remarkable efficacy in treating multiple myeloma, bortezomib has been tested in solid cancers; unfortunately, it has generally failed to produce clinical responses.

Bortezomib inhibits an intracellular protein complex called the proteasome. The proteasome is an attractive drug target because it is involved in regulation of the cell cycle and apoptosis, processes that when dysregulated in cancer cells lead to tumor progression, drug resistance and altered immune surveillance. By inhibiting the 20S proteasome, which selectively degrades proteins involved in cellular homeostasis, bortezomib stabilizes proapoptotic members of the Bcl-2 family, inhibits two major pathways leading to NF-κB activation, and causes intracellular accumulation of misfolded proteins; all of which effects contribute to killing tumor cells. Blockade of NF-κB activation increases apoptosis, reduces production of angiogenic cytokines, inhibits tumor cell adhesion to stroma, and alleviates immune suppression.

However, broader use of bortezomib to treat cancer appears to be prevented by systemic toxicity. Bortezomib distributes to healthy tissues, causing diarrhea, fatigue, fluid retention, hypokalemia, hyponatremia, hypotension, malaise, nausea, orthostasis, bortezomib-induced peripheral neuropathy (BIPN) and hematologic toxicities, of which thrombocytopenia is the most severe. At the recommended dose of bortezomib there is a therapeutic window for the treatment of MM that may be afforded by the unique sensitivity of MM cells to inhibition of nuclear factor-κB (NF-κB) and induction of the unfolded protein response. Solid cancers (e.g., prostate, pancreatic and breast cancer) appear to be less sensitive, however, and attempts to achieve efficacy by increasing bortezomib dosage have been prevented by dose-limiting toxicities (DLTs). The poor localization of bortezomib to tumors appears to contribute to its low therapeutic index (TI) in solid cancers. In mice bearing PC3 prostate tumors, healthy organ exposure to $^{14}$C-bortezomib was as much as 9-fold greater than tumor exposure, and proteasome inhibition in healthy tissue appears to be greater than in solid tumors. Thus, it is necessary to design compounds that selectively target the proteasome in tumor cells to overcome the obstacle of DLTs due to proteasome inhibition in healthy tissues.

Extensive efforts over the past few decades have focused on therapies tailored to the specific patient—so-called personalized medicine. Due to advances in genetic sequencing technology it is now possible and increasingly cost-effective to genotype cancerous tissue to identify the individual genetic profile of the cancer and thus the specific mutated or dysfunctional proteins that may be responsible for tumor growth. Such "driver" proteins may be then targeted with agents that block their function and thus kill the cancer. While conceptually sound, this approach has been hampered by the unexpected genetic diversity and genomic instability of cancer. Significantly different genotypes of cancer may be present within a single tumor, making targeted therapy ineffective for many patients. Even when the majority of cancer cells in a tumor share a sufficiently similar genetic makeup that a single targeted therapy is effective, small numbers of cancer cells bearing a resistant mutation may survive the therapy, leading to relapse after an initial improvement.

Therapies selectively targeting the tumor and its microenvironment with cytotoxic agents whose effect does not depend on the genetic makeup of the cancer are needed. Such therapies remain elusive, however.

SUMMARY OF THE INVENTION

One aspect of the present invention relates to a FAP-activated prodrug of a proteasome inhibitor represented by A-B, or a pharmaceutically acceptable salt thereof, wherein
  A represents a substrate for Fibroblast Activation Protein (FAP);
  B represents a proteasome inhibitor moiety which, when released in a free form from the prodrug as a product of cleavage by FAP, inhibits the proteolytic activity of a proteasome with a Ki of 500 nM or less;
  A and B being covalently linked by a bond that is enzymatically cleaved by FAP to release B in said free form; and
  the prodrug has a $k_{cat}/K_m$ for FAP cleavage of the bond linking A and B of at least 10 fold more than for prolyl endopeptidase EC 3.4.21.26 (PREP).

Another aspect of the present invention relates to a FAP-activated proteasome inhibitor represented by formula I:

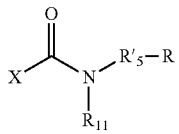

or a pharmaceutically acceptable salt thereof,
wherein
X—C(=O)NR$_{11}$—R'$_5$— represents the FAP substrate sequence, X is an N-acyl peptidyl group, —NR$_{11}$—R'$_5$ is an amino acid residue or analog thereof that binds the P'$_1$ specificity subsite of FAP, and the FAP substrate sequence is cleaved by FAP to release NHR$_{11}$—R'$_5$—R; and
NHR$_{11}$—R'$_5$—R is a proteasome inhibitor.

Another aspect of the present invention relates to a compound or a pharmaceutically acceptable salt thereof represented by the formula:

R—Xaa$_1$-Xaa$_2$-Y wherein
R is an acyl group;
Xaa$_1$ is selected from the group consisting of Ala, Cys, Asp, Glu, Phe, Gly, His, Ile, Lys, Leu, Met, Asn, Pro, Gln, Arg, Ser, Thr, Val, Trp, and Tyr;
Xaa$_2$ is selected from the group consisting of Ala, Cys, Asp, Glu, Phe, Gly, His, Ile, Lys, Leu, Met, Asn, Pro, Gln, Arg, Ser, Thr, Val, Trp, and Tyr; and
Y is

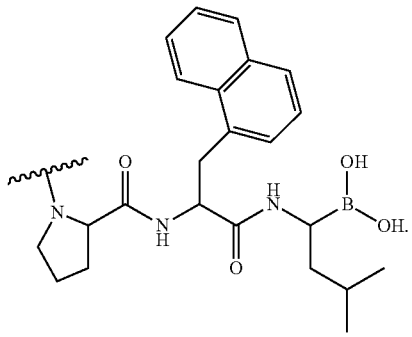 [SMILES: *N1CCC[C@@H]1C(=O)NC(Cc1cccc2ccccc12)C(=O)NC(CC(C)C)B(O)O]

Another aspect of the present invention relates to pharmaceutical compositions, and methods of using the compounds and compositions in, for example, treating cancer or other cell proliferative diseases.

BRIEF DESCRIPTION OF THE FIGURES

FIG. 27 shows the FAP activity in various human cancer cell lines.

DETAILED DESCRIPTION OF THE INVENTION

Figure 1:
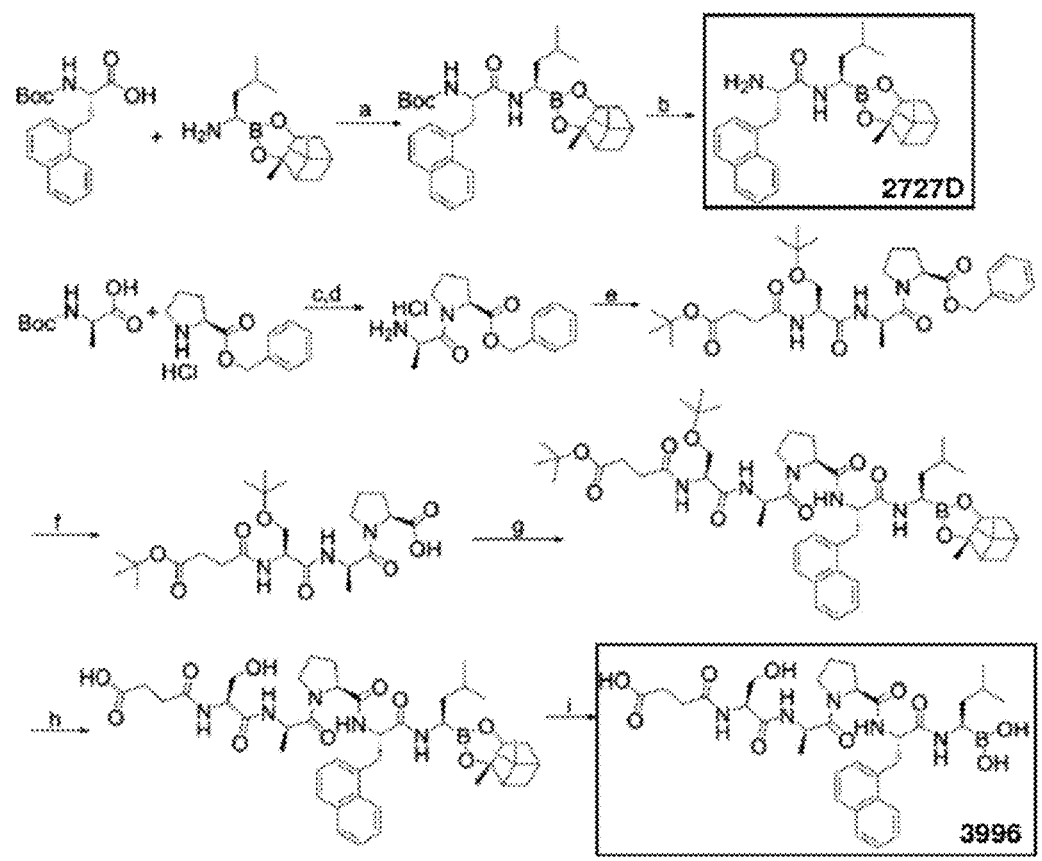
FIG. 1 shows the synthesis of ARI-2727D and ARI-3996. The following reagents were used: (a) HATU/DMF/DIPEA, 95%; (b) 4 M HCl in dioxane, 100%; (c) HATU/DMF/DIPEA, 90%; (d) 4M HCl in dioxane, 100%; (e) tBu-Suc-Ser(tBu)-OH, HATU/DMF/DIPEA, 90%; (f) Pd(OH)$_2$—C/H$_2$/methanol, 90%; (g) 2727D, HATU/DMF/DIPEA, 85%; (h) TFA/DCM, 90%; (i) PhB(OH)$_2$, pentane-water-acetonitrile, 70%.

The present invention relates to compounds designed selectively to target solid tumors with a reduced toxicity profile. Bortezomib (Velcade®) is an effective treatment for multiple myeloma, but its mechanism of action results in dose-limiting toxicities (DLTs) of peripheral neuropathy and loss of platelets, which prevent treatment of common solid cancers. The compounds of the present invention are designed to remain inactive in healthy organs and to be activated by the tumor-associated enzyme called fibroblast activation protein (FAP) to unleash a cytotoxic bortezomib-like warhead in tumors, thereby reducing the toxic side effects that prevent safe treatment of solid tumors with bortezomib.

The selective targeting and reduced toxicity of the compounds of the invention allows the treatment of solid cancers independent of their genetic makeup. Furthermore, the selective activation of the compounds in the vicinity of the tumors results in a high concentration of the cytotoxic agent in the tumor but a low concentration in the rest of the body. The high local concentration kills tumors with a lower dose of the drug than previously possible, because a drug lacking the capability to be selectively delivered circulates throughout the body, causing systemic toxicity, often at a dose that is suboptimal for treatment of the cancer.

The present invention also allows the offsetting of the immunosuppressive properties of tumors. Because solid tumors are often surrounded by cancerous stromal cells, they are protected from the immune system of the patient. This immunosuppression can be removed by killing the stromal cells, but conventional chemotherapies including Velcade® fail to do so. The present invention is capable of killing stromal cells because they overexpress FAP and thus activate the compounds of the invention to release the warhead. Thus the present invention can have multiple mechanisms of action, such as direct killing of tumors or re-activation of the patient immune response after killing of the supportive stromal tissue, resulting in killing of the tumor through a natural immune response.

The FAP address moiety, or FAP binding portion, of the invention may be chemically attached to a variety of cytotoxic warheads. Thus, any proteasome inhibitor with a validated target and mode of action would benefit from use with the claimed invention. Conjugation (chemical attachment) of a validated proteasome inhibitor possessing anticancer activity, to the FAP address moiety confers selective delivery, increased potency, and decreased off-target toxicity.

Conjugation of the FAP address moiety to a known protease inhibitor is similar to, but conceptually different from, a prodrug, because the FAP address moiety is designed to bind and be cleaved by FAP selectively over other proteases present in the body, especially DPPII, DPP8, DPP9, DPPIV, and PREP. This specificity for enzyme subtype is essential for the desired effect of delivering the released cytotoxic agent to the tumor.

Many proteasome inhibitors with anticancer activity are known in the art, and may be divided according to covalent and non-covalent inhibitors, with the covalent inhibitors further divided into aldehydes, boronates, epoxyketones, beta-lactones, vinyl sulfones, and α,β-unsaturated carbonyls, among others. Examples in the aldehyde class include MG-132, PSI, and fellutamide B. Examples in the boronate class include bortezomib (Velcade®), CEP-18770, MLN2238, and MLN9708. Examples in the epoxyketone class include epoxomicin, carfilzomib (PR-171), NC-005, YU-101, LU-005, YU-102, NC-001, LU-001, NC-022, PR-957 (LMP7), CPSI (f35), LMP2-sp-ek, BODIPY-NC-001, azido-NC-002, and ONX 0912 (opromozib). Examples in the beta-lactone class include omuralide, PS-519, marizomib, and belactosin A. Examples in the vinyl sulfone class include $^{125}$I-NIP-L$_3$VS, NC-005-VS, and MV151. Discussion and validation of these inhibitors and others may be found, for example, in Kisselev et al. "Proteasome Inhibitors: An Expanding Army Attacking a Unique Target," Chemistry and Biology 19, Jan. 27, 2012, 99-115 (incorporated by reference).

Chemical conjugation of any of these proteasome inhibitors with a FAP address moiety as described in the present invention would be expected to deliver selectively the cytotoxic agent to solid tumors and the surrounding stromal cells. Since the FAP address moiety is a selective substrate for FAP, the identity of the cytotoxic agent attached to the FAP address moiety is not important to the selective delivery. FAP will cleave the chemical bond attaching the address moiety to the warhead; such a chemical bond may be, for example, an ester or amide bond, among others.

One aspect of the present invention relates to a FAP-activated prodrug of a proteasome inhibitor represented by A-B, or a pharmaceutically acceptable salt thereof, wherein
    A represents a substrate for Fibroblast Activation Protein (FAP);
    B represents a proteasome inhibitor moiety which, when released in a free form from the prodrug as a product of cleavage by FAP, inhibits the proteolytic activity of a proteasome with a Ki of 500 nM or less;

A and B being covalently linked by a bond that is enzymatically cleaved by FAP to release B in said free form; and the prodrug has a $k_{cat}/K_m$ for FAP cleavage of the bond linking A and B of at least 10 fold more than for prolyl endopeptidase EC 3.4.21.26 (PREP).

In certain embodiments, the free form of said proteasome inhibitor moiety has an $IC_{50}$ for inhibiting proteasome activity of cells in vitro that is at least 10 fold less relative to said prodrug.

In certain embodiments, the free form of said proteasome inhibitor moiety has a Ki for inhibiting proteasome activity that is at least 10 fold less relative to said prodrug.

In certain embodiments, the free form of said proteasome inhibitor moiety has at least 5 fold greater cell permeability into human cells than said prodrug.

In certain embodiments, the prodrug has a therapeutic index in vivo at least 5 fold greater than said free form of said proteasome inhibitor moiety.

In certain embodiments, the prodrug has a therapeutic index in vivo of at least 10.

In certain embodiments, the prodrug has a maximum tolerated dose at least 10 times greater than [(1R)-3-methyl-1-({(2S)-3-phenyl-2-[(pyrazin-2-ylcarbonyl)amino]propanoyl}amino)butyl]boronic acid.

In certain embodiments, said free form of said proteasome inhibitor moiety is a dipeptidyl moiety, which when released from the prodrug as an open chain product of cleavage by FAP, undergoes cyclization-dependent inactivation over time.

In certain embodiments, said open chain product undergoes cyclization-dependent inactivation with a $T_{1/2}$ of 5 hours or less.

In certain embodiments, A represents a peptide or peptide analogue which is a substrate for FAP, which peptide or peptide analogue includes an N-terminal blocking group.

In certain embodiments, the peptide or peptide analogue is 2-10 amino acid residues in length.

In certain embodiments, the peptide or peptide analogue is C-terminally linked to B.

In certain embodiments, at least one amino acid residue of the peptide or peptide analog is a non-naturally occurring amino acid analog.

In certain embodiments, the N-terminal blocking group is a moiety which, at physiological pH, reduces the cell permeability of said prodrug relative to said free form of said proteasome inhibitor.

In certain embodiments, the N-terminal blocking group includes one or more functional groups that are ionized at physiological pH.

In other embodiments, the N-terminal blocking group is a (lower alkyl)-C(=O)— substituted with one or more functional groups that are ionized at physiological pH.

In certain other embodiments, the N-terminal blocking group is represented by the formula —C(=O)—(CH$_2$)$_{1-10}$—C(=O)—OH.

In certain embodiments, the N-terminal blocking group includes one or more carboxyl groups. In another embodiment, the N-terminal blocking group is succinyl.

In certain embodiments, B is a covalent or non-covalent proteasome inhibitor.

In certain other embodiments, B is a covalent proteasome inhibitor.

In certain embodiments, B is a dipeptidyl moiety having at its carboxy terminus an electrophilic functional group that can form a covalent adduct with an amino acid residue in the active site of a proteasome.

In certain embodiments, the electrophilic functional group is an aldehyde, boronic acid, boronate ester, epoxyketone, beta-lactone, vinyl sulfone, or α,β-unsaturated carbonyl.

In certain embodiments, the electrophilic functional group is an aldehyde, boronic acid, or epoxyketone.

In another embodiment, the electrophilic functional group is an epoxyketone.

In certain embodiments, B is selected from the group consisting of:

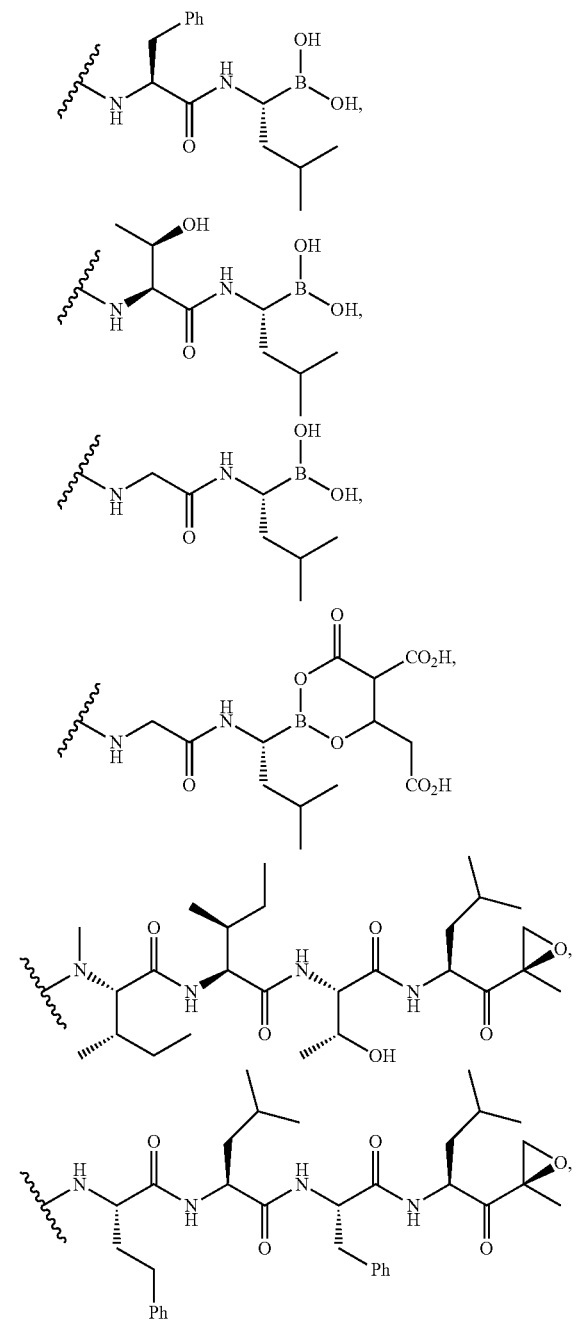

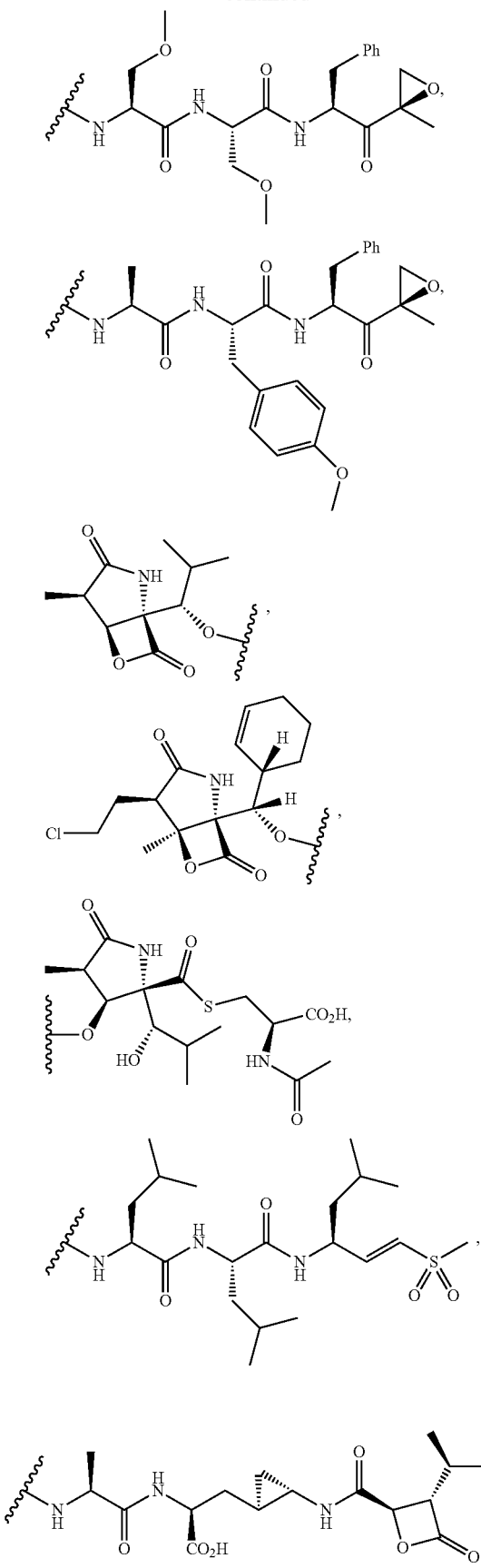
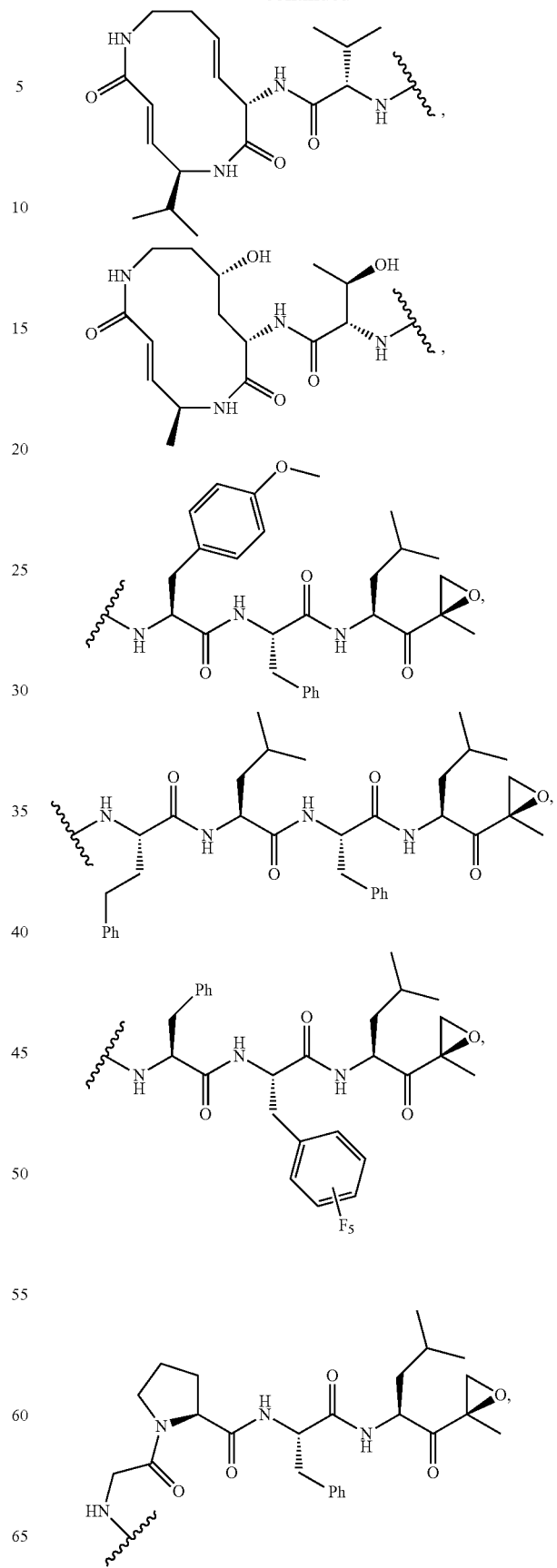

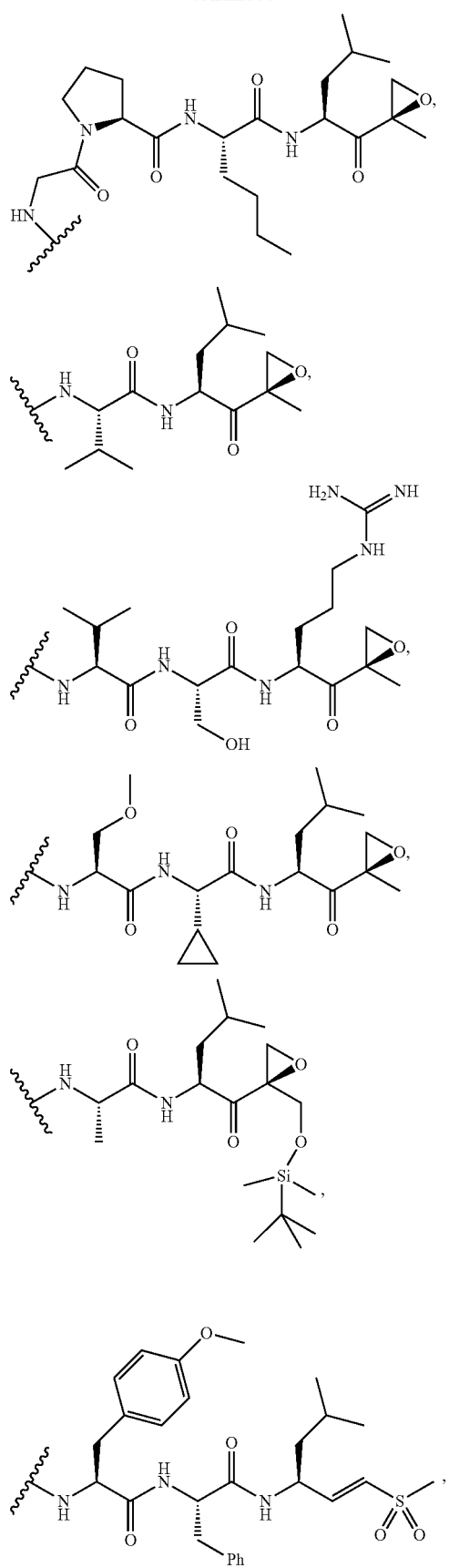
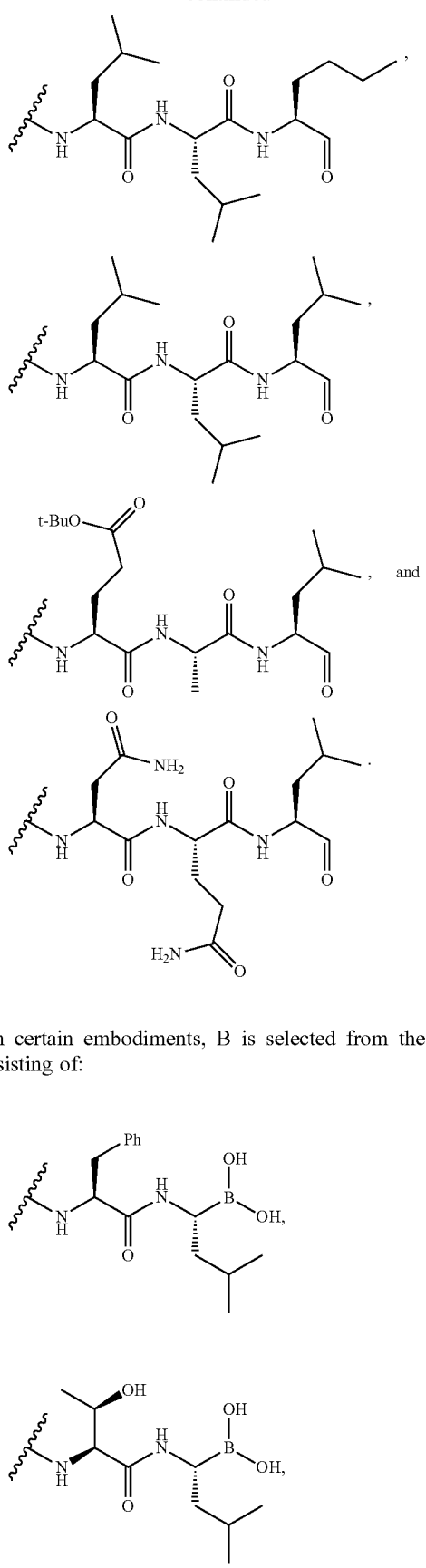
In certain embodiments, B is selected from the group consisting of:
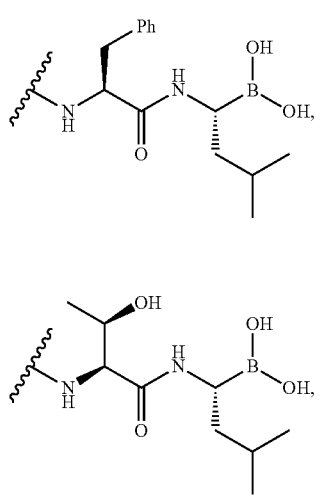

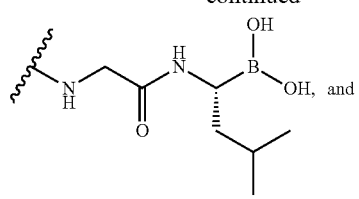
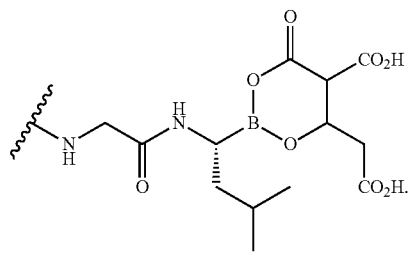
In certain other embodiments, B is selected from the group consisting of:
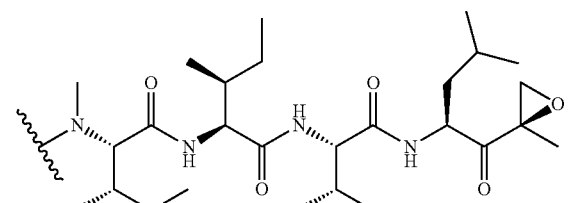
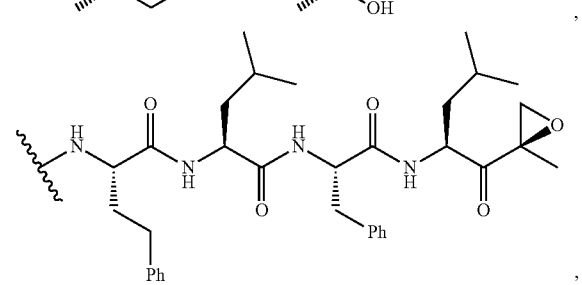
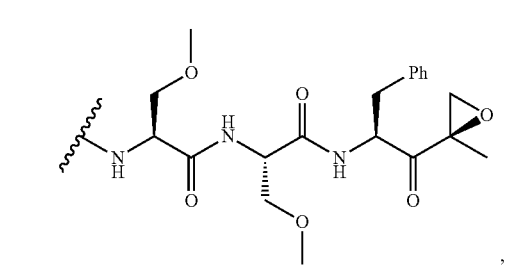
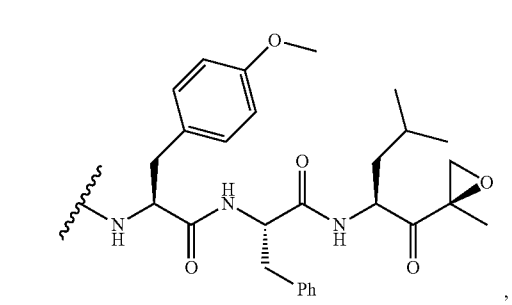
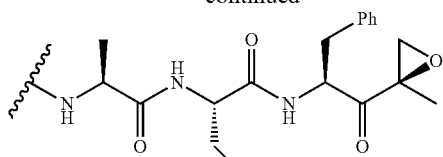
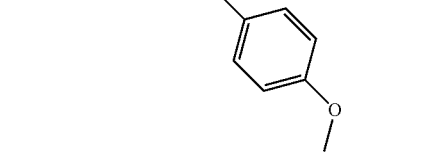
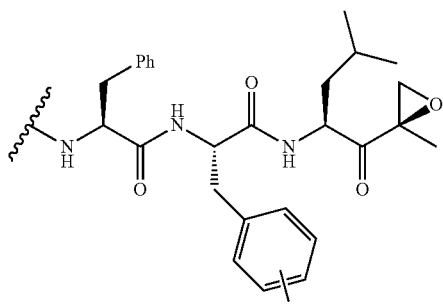
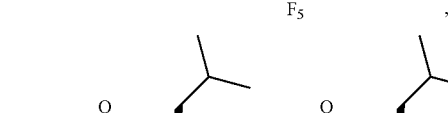

-continued

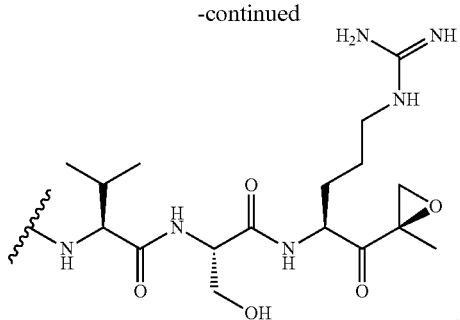

,

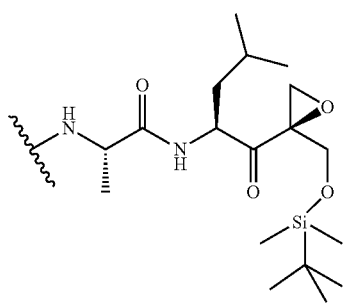

, and

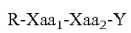.

Another aspect of the present invention relates to the compounds described above, wherein A further comprises a self-eliminating linker attached to B by a chemical bond.

In certain embodiments, the self-eliminating linker is p-aminobenzyloxocarbonyl (PABC) or 2,4-bis(hydroxymethyl)aniline.

Another aspect of the present invention relates to a compound or a pharmaceutically acceptable salt thereof represented by the formula:

R-Xaa$_1$-Xaa$_2$-Y wherein

R is an acyl group;

Xaa$_1$ is selected from the group consisting of Ala, Cys, Asp, Glu, Phe, Gly, His, Ile, Lys, Leu, Met, Asn, Pro, Gln, Arg, Ser, Thr, Val, Trp, and Tyr;

Xaa$_2$ is selected from the group consisting of Ala, Cys, Asp, Glu, Phe, Gly, His, Ile, Lys, Leu, Met, Asn, Pro, Gln, Arg, Ser, Thr, Val, Trp, and Tyr; and Y is

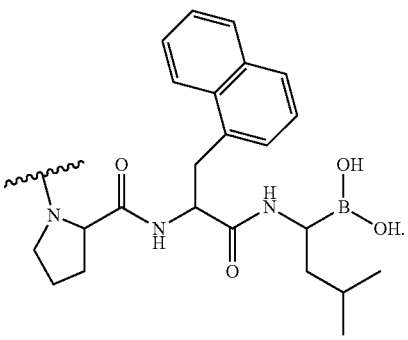 [SMILES: *N1CCC[C@@H]1C(=O)NC(Cc1cccc2ccccc12)C(=O)NC(CC(C)C)B(O)O]

In certain embodiments, the compound further comprises a self-eliminating linker with a chemical bond to the carboxyl terminus of Xaa$_2$ and a chemical bond to Y.

In certain embodiments, the self-eliminating linker is p-aminobenzyloxocarbonyl (PABC) or 2,4-bis(hydroxymethyl)aniline.

In certain embodiments, R is selected from the group consisting of formyl, acetyl, benzoyl, trifluoroacetyl, succinyl, and methoxysuccinyl.

In certain other embodiments, R is succinyl or methoxysuccinyl.

In another embodiment, R is succinyl.

In certain embodiments, Xaa$_1$ is Cys, Met, Ser, or Thr.

In certain other embodiments, Xaa$_1$ is Ser.

In certain embodiments, Xaa$_2$ is Ala, Gly, Ile, Leu, or Val.

In certain embodiments, Xaa$_2$ is Ala.

In certain other embodiments, Xaa$_2$ is (D)-Ala.

Y is

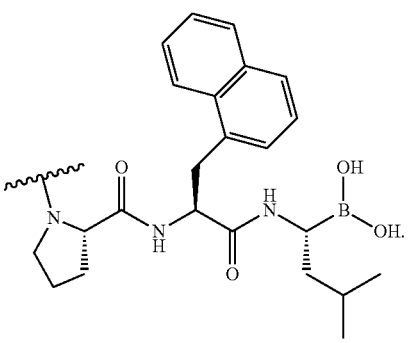

In certain embodiments, R is selected from the group consisting of formyl, acetyl, benzoyl, trifluoroacetyl, succinyl, and methoxysuccinyl; Xaa$_1$ is Cys, Met, Ser, or Thr; Xaa$_2$ is Ala, Gly, Ile, Leu, or Val; and Y is

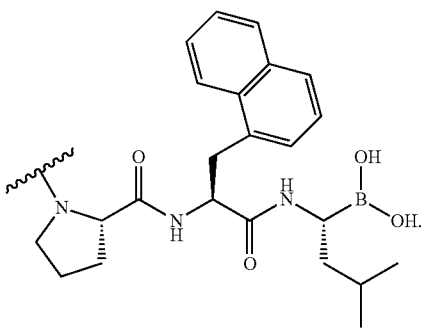 [SMILES: *N1CCC[C@H]1C(=O)N[C@@H](Cc1cccc2ccccc12)C(=O)N[C@@H](CC(C)C)B(O)O]

In certain embodiments, R is succinyl or methoxysuccinyl; Xaa$_1$ is Ser; Xaa$_2$ is Ala; and Y is

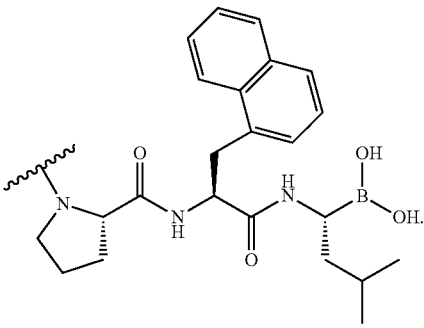 [SMILES: *N1CCC[C@H]1C(=O)N[C@@H](Cc1cccc2ccccc12)C(=O)N[C@@H](CC(C)C)B(O)O]

In certain embodiments, R is succinyl; Xaa$_1$ is Ser; Xaa$_2$ is (D)-Ala; and Y is

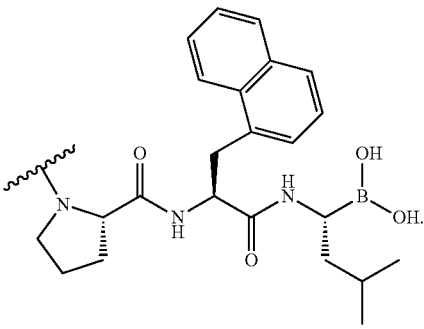 [SMILES: *N1CCC[C@H]1C(=O)N[C@@H](Cc1cccc2ccccc12)C(=O)N[C@@H](CC(C)C)B(O)O]

In certain embodiments, the present invention relates to a compound or a pharmaceutically acceptable salt thereof represented by

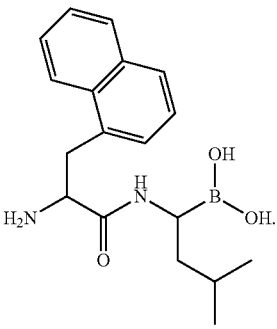 [SMILES: CC(C)CC(NC(=O)C(N)Cc1cccc2ccccc12)B(O)O]

In certain embodiments, the compound is represented by

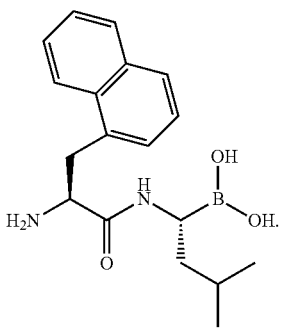 [SMILES: CC(C)C[C@H](NC(=O)[C@@H](N)Cc1cccc2ccccc12)B(O)O]

Another aspect of the present invention relates to a FAP-activated proteasome inhibitor represented by formula I:

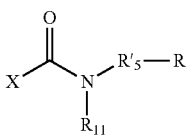

or a pharmaceutically acceptable salt thereof, wherein

X—C(=O)NR$_{11}$—R'$_5$— represents the FAP substrate sequence, X is an N-acyl peptidyl group, —NR$_{11}$—R'$_5$ is an amino acid residue or analog thereof that binds the P'$_1$ specificity subsite of FAP, and the FAP substrate sequence is cleaved by FAP to release NHR$_{11}$—R'$_5$—R; R$_{11}$ represents H or lower alkyl; and NHR$_{11}$—R'$_5$—R is a proteasome inhibitor.

In certain embodiments, the present invention relates to the FAP-activated proteasome inhibitor described above, represented by formula II:

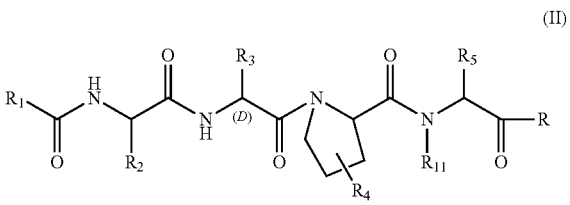

wherein

R$_1$—(C=O)— represents an acyl N-terminal blocking group;

R$_2$ represents H, lower alkyl, or a mono- or di-hydroxy-substituted lower alkyl;

R$_3$ represents H, halogen, or lower alkyl;

R$_4$ is absent or represents lower alkyl, —OH, —NH$_2$ or halogen;

R$_5$ represents a large hydrophobic amino acid sidechain;

R$_{11}$ represents H or lower alkyl; and the FAP-activated proteasome inhibitor is cleaved by FAP to release a proteasome inhibitor represented by

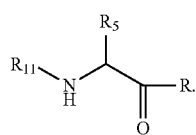
In certain embodiments of the FAP-activated proteasome inhibitor,
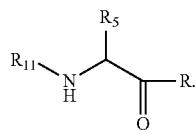
is selected from the group consisting of:
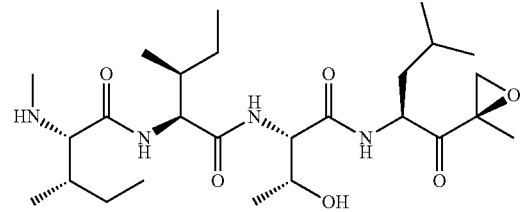,
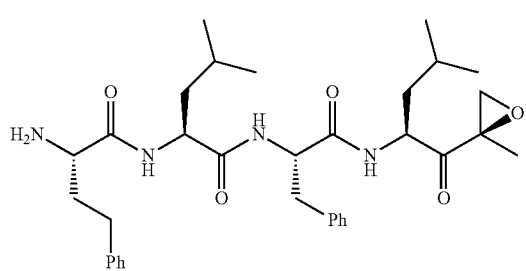,
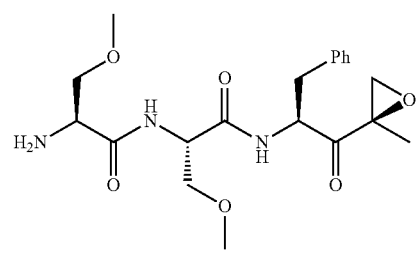,
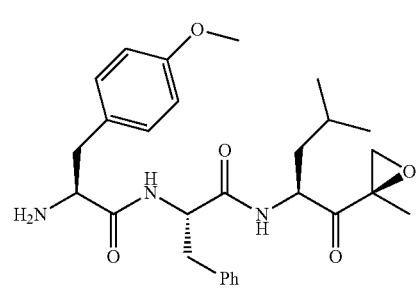,
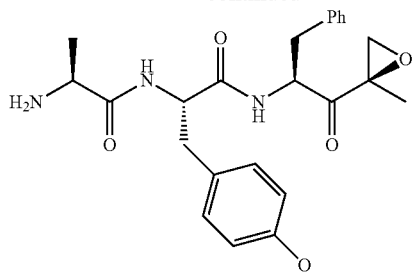,
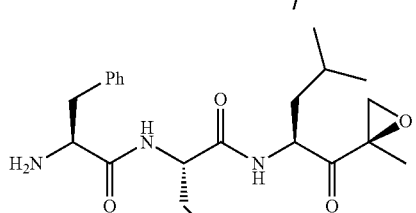,
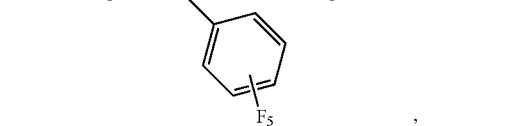,
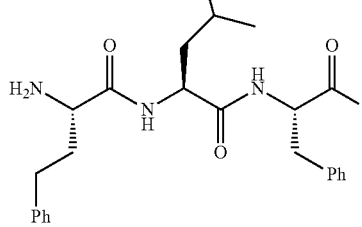,
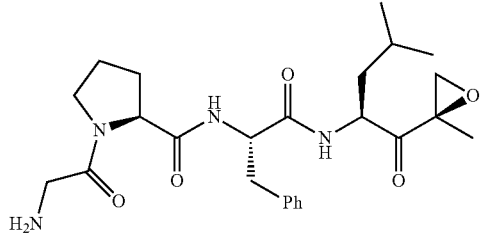,
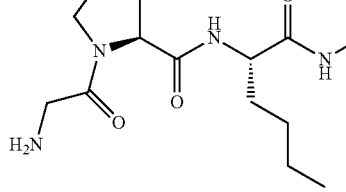,
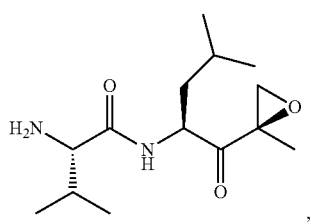, -continued

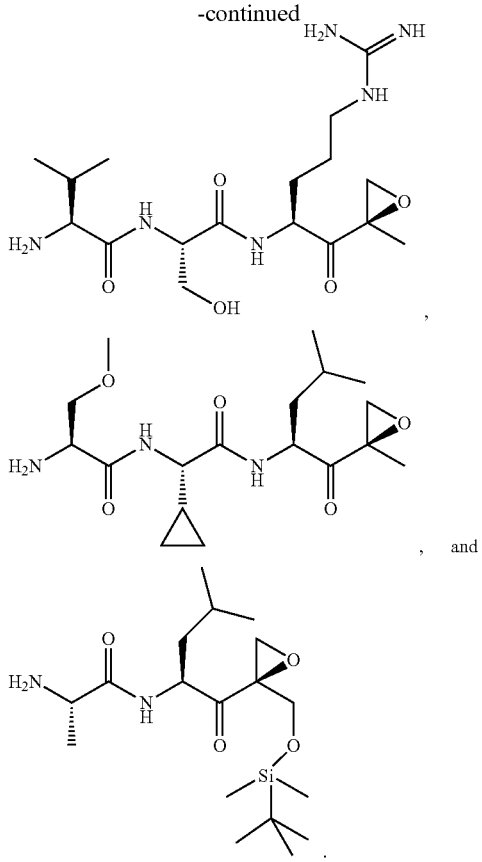

, and

In certain embodiments, the FAP-activated proteasome inhibitor is represented by formula III:

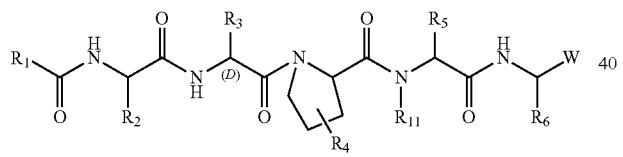

(III)

wherein
$R_1$—(C=O)— represents an acyl N-terminal blocking group;
$R_2$ represents H, lower alkyl, or a mono- or di-hydroxy-substituted lower alkyl;
$R_3$ represents H, halogen, or lower alkyl;
$R_4$ is absent or represents lower alkyl, —OH, —NH$_2$ or halogen;
$R_5$ represents a large hydrophobic amino acid sidechain;
$R_6$ represents alkyl, cycloalkyl, aryl, heterocycle or —(CH$_2$)$_n$—R$_7$;
$R_7$ represents aryl, aralkyl, cycloalkyl, alkoxy, alkylthio, —OH or —SH;
$R_{11}$ represents H or lower alkyl;
W represents —CN, an epoxyketone, —CH=NR$_5$,

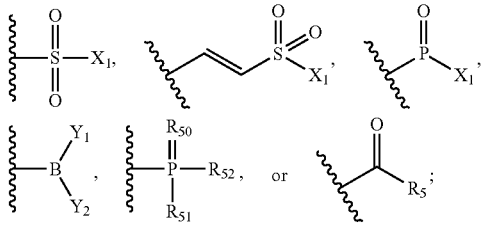

$R_8$ represents H, alkyl, alkenyl, alkynyl, —C(X$_1$)(X$_2$)X$_3$, —(CH$_2$)$_m$—R$_9$, —(CH$_2$)$_n$—OH, —(CH$_2$)—O-alkyl, —(CH$_2$)—O-alkenyl, —(CH$_2$)—O-alkynyl, —(CH$_2$)$_n$—O—(CH$_2$)$_m$—R$_9$, —(CH$_2$)$_n$—SH, —(CH$_2$)$_n$—S-alkyl, —(CH$_2$)—S-alkenyl, —(CH$_2$)$_n$—S-alkynyl, —(CH$_2$)$_n$—S—(CH$_2$)$_m$—R$_9$, —C(=O)C(=O)NH$_2$, —C(=O)C(=O)OR$_{10}$;
$R_9$ represents, independently for each occurrence, a substituted or unsubstituted aryl, aralkyl, cycloalkyl, cycloalkenyl, or heterocycle;
$R_{10}$ represents, independently for each occurrence, hydrogen, or a substituted or unsubstituted alkyl, alkenyl, aryl, aralkyl, cycloalkyl, cycloalkenyl, or heterocycle;
$Y_1$ and $Y_2$ can independently or together be OH, or a group capable of being hydrolyzed to a hydroxyl group, including cyclic derivatives where $Y_1$ and $Y_2$ are connected via a ring having from 5 to 8 atoms in the ring structure;
$R_{50}$ represents O or S;
$R_{51}$ represents N$_3$, SH$_2$, NH$_2$, NO$_2$ or —OR$_{10}$;
$R_{52}$ represents hydrogen, lower alkyl, amine, —OR$_{10}$, or a pharmaceutically acceptable salt, or $R_{51}$ and $R_{52}$ taken together with the phosphorous atom to which they are attached complete a heterocyclic ring having from 5 to 8 atoms in the ring structure;
$X_1$ is halogen;
$X_2$ and $X_3$ each represent H or halogen;
m is zero or an integer in the range of 1 to 8; and n is an integer in the range of 1 to 8.
In certain embodiments, the present invention relates to the FAP-activated proteasome inhibitor described above, represented by

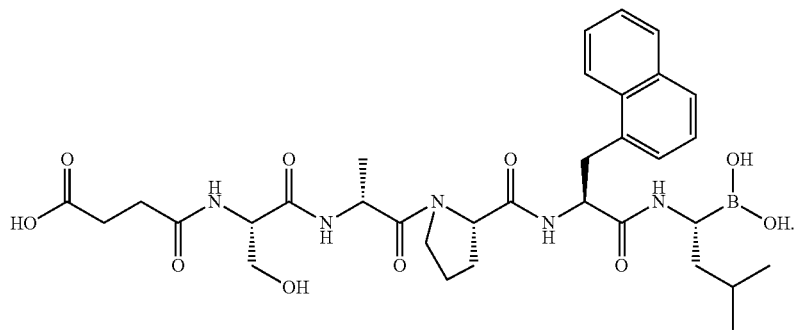 [SMILES: CC(C)C[C@H](NC(=O)[C@H](Cc1cccc2ccccc12)NC(=O)[C@@H]1CCCN1C(=O)[C@@H](C)NC(=O)[C@H](CO)NC(=O)CCC(=O)O)B(O)O]

Another aspect of the present invention relates to a pharmaceutical composition, comprising a compound described herein; and a pharmaceutically acceptable excipient.

Another aspect of the present invention relates to a method of inhibiting proteasome function in a cell, comprising contacting the cell with an effective amount of a compound described herein.

Another aspect of the present invention relates to a method of reducing the rate of muscle protein degradation in a cell, comprising contacting the cell with an effective amount of a compound described herein.

Another aspect of the present invention relates to a method of reducing the activity of NF-κB in a cell, comprising contacting the cell with an effective amount of a compound described herein.

Another aspect of the present invention relates to a method of reducing the rate of proteasome-dependent intracellular protein breakdown, comprising contacting a cell with an effective amount of a compound described herein.

Another aspect of the present invention relates to a method of reducing the rate of degradation of p53 protein in a cell, comprising contacting the cell with an effective amount of a compound described herein.

Another aspect of the present invention relates to a method of inhibiting cyclin degradation in a cell, comprising contacting the cell with an effective amount of a compound described herein.

Another aspect of the present invention relates to a method of inhibiting antigen presentation in a cell, comprising contacting the cell with an effective amount of a compound described herein.

Another aspect of the present invention relates to a method of treating cancer, psoriasis, restenosis, or other cell proliferative disease, comprising administering to a mammal in need thereof a therapeutically effective amount of a compound described herein.

Another aspect of the present invention relates to a method of treating cancer, psoriasis, restenosis, or other cell proliferative disease, comprising co-administering to a mammal in need thereof a therapeutically effective amount of a compound described herein; and a therapeutically effective amount of a chemotherapeutic agent.

In certain embodiments, the chemotherapeutic agent is docetaxel, paclitaxel, imatinib mesylate, gemcitabine, cis-platin, carboplatin, 5-fluorouracil, pemetrexed, methotrexate, doxorubicin, lenalidomide, dexamethasone, or monomethyl auristatin.

In certain other embodiments, the chemotherapeutic agent is docetaxel, gemcitabine, carboplatin, or doxorubicin.

In yet other embodiments, the chemotherapeutic agent is MG-132, PSI, fellutamide B, bortezomib, CEP-18770, MLN-2238, MLN-9708, epoxomicin, carfilzomib (PR-171), NC-005, YU-101, LU-005, YU-102, NC-001, LU-001, NC-022, PR-957 (LMP7), CPSI (β5), LMP2-sp-ek, BODIPY-NC-001, azido-NC-002, ONX-0912, omuralide, PS-519, marizomib, belactosin A, $^{125}$I-NIP-L$_3$VS, NC-005-VS, or MV151.

Another aspect of the present invention relates to a method of treating cancer, comprising administering to a mammal in need thereof a therapeutically effective amount of a compound described herein.

In certain embodiments, the cancer is a solid tumor.

In certain other embodiments, the method further comprises administering to a mammal in need thereof a therapeutically effective amount of a chemotherapeutic agent.

In yet other embodiments, the cancer is a solid tumor.

In still yet other embodiments, the chemotherapeutic agent is docetaxel, paclitaxel, imatinib mesylate, gemcitabine, cis-platin, carboplatin, 5-fluorouracil, pemetrexed, methotrexate, doxorubicin, lenalidomide, dexamethasone, or monomethyl auristatin.

In another embodiment, the chemotherapeutic agent is docetaxel, gemcitabine, carboplatin, or doxorubicin.

In certain embodiments, the chemotherapeutic agent is MG-132, PSI, fellutamide B, bortezomib, CEP-18770, MLN-2238, MLN-9708, epoxomicin, carfilzomib (PR-171), NC-005, YU-101, LU-005, YU-102, NC-001, LU-001, NC-022, PR-957 (LMP7), CPSI (β5), LMP2-sp-ek, BODIPY-NC-001, azido-NC-002, ONX-0912, omuralide, PS-519, marizomib, belactosin A, $^{125}$I-NIP-L$_3$VS, NC-005-VS, or MV151.

Another aspect of the present invention relates to method of reducing the rate of loss of muscle mass in a mammal, comprising administering to a mammal in need thereof a therapeutically effective amount of a compound described herein.

Another aspect of the present invention relates to a method of reducing the activity of NF-κB in a mammal, comprising administering to a mammal in need thereof a therapeutically effective amount of a compound described herein.

Another aspect of the present invention relates to a method of reducing the rate of proteasome-dependent intracellular protein breakdown in a mammal, comprising administering to a mammal in need thereof a therapeutically effective amount of a compound described herein.

Another aspect of the present invention relates to a method of reducing the rate of degradation of p53 protein in a mammal, comprising administering to a mammal in need thereof a therapeutically effective amount of a compound described herein.

Another aspect of the present invention relates to a method of inhibiting cyclin degradation in a mammal, comprising administering to a mammal in need thereof a therapeutically effective amount of a compound described herein.

Another aspect of the present invention relates to a method of inhibiting antigen presentation in a mammal, comprising administering to a mammal in need thereof a therapeutically effective amount of a compound described herein.

Another aspect of the present invention relates to a method of inhibiting inducible NF-κB dependent cell adhesion in a mammal, comprising administering to a mammal in need thereof a therapeutically effective amount of a compound described herein.

Another aspect of the present invention relates to a method of inhibiting HIV infection in a mammal, comprising administering to a mammal in need thereof a therapeutically effective amount of a compound described herein.

Another aspect of the present invention relates to a method of quantifying the amount of FAP expressed by or in the vicinity of a tumor in a mammal, comprising the steps of:

administering to said mammal an effective amount of a compound represented by Formula IV:

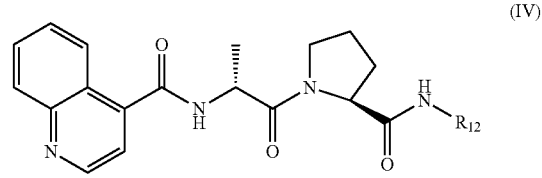

(IV)

wherein $R_{12}$ is a fluorophore or chromophore;

illuminating the mammal in the vicinity of the tumor; and measuring the amount of fluorescence in the vicinity of the tumor.

In certain embodiments, $R_{12}$ is selected from the group consisting of:

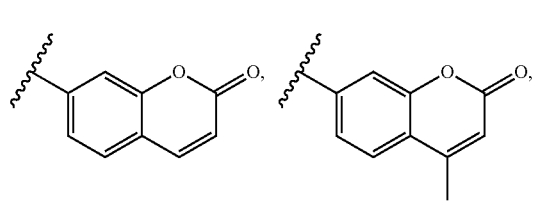

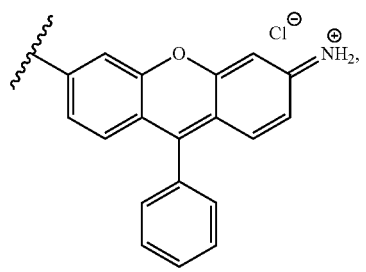

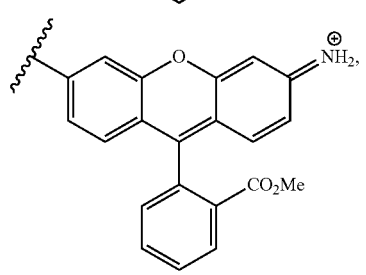

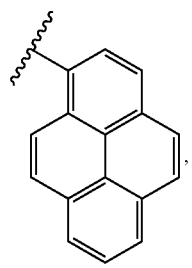

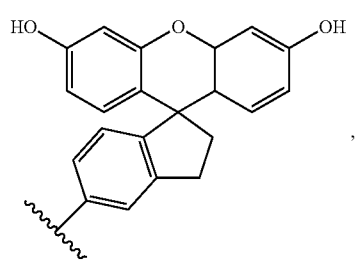

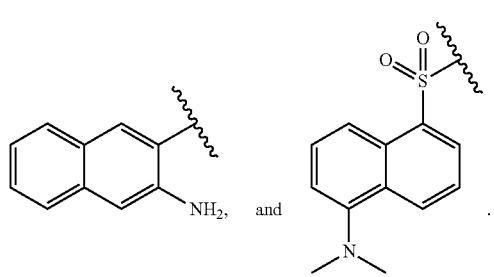

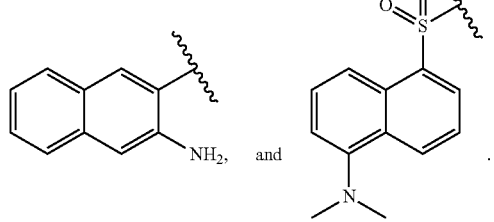

In certain other embodiments, $R_{12}$ is

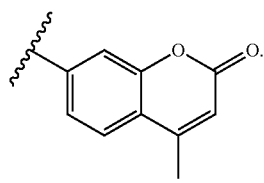 [SMILES: *c1ccc2c(C)cc(=O)oc2c1]

Another aspect of the present invention relates to a method of quantifying the amount of FAP expressed by a tumor biopsy sample, comprising the steps of:

combining said tumor biopsy sample with an effective amount of a compound represented by Formula IV, thereby forming a mixture:

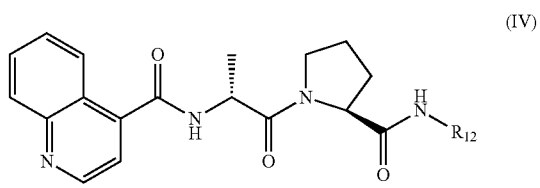

(IV)

wherein $R_{12}$ is a fluorophore or chromophore;
illuminating the mixture; and
measuring the amount of fluorescence in the mixture.

In certain embodiments, $R_{12}$ is selected from the group consisting of:

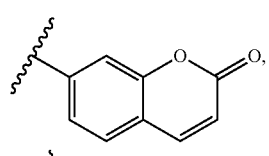

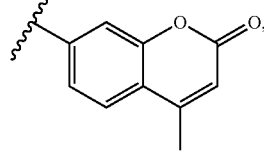

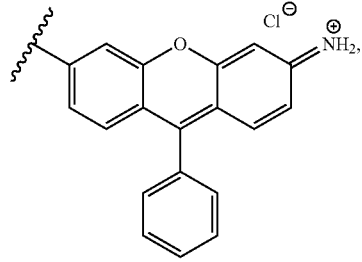

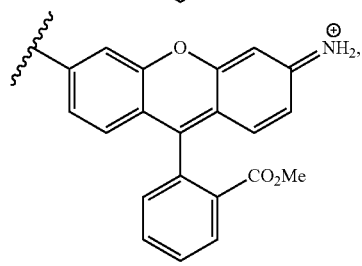

-continued

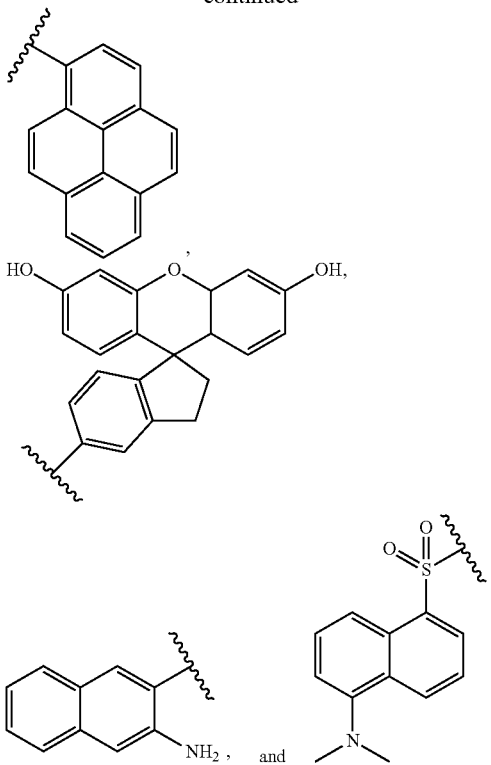

In certain other embodiments, $R_{12}$ is

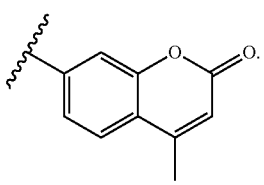 [SMILES: *c1ccc2c(C)cc(=O)oc2c1]

Another aspect of the present invention relates to a method described herein, wherein said mammal is a primate, equine, canine, feline, or bovine.

Another aspect of the present invention relates to a method described herein, wherein said mammal is a human.

Another aspect of the present invention relates to a method described herein, wherein the compound is administered to the mammal by inhalation, orally, intravenously, sublingually, ocularly, transdermally, rectally, vaginally, topically, intramuscularly, intra-arterially, intrathecally, subcutaneously, buccally, or intranasally.

Another aspect of the present invention relates to a method described herein, wherein the compound is administered to the mammal intravenously.

Another aspect of the present invention relates to a method for reducing local immunosuppression and/or tumor supporting-activity mediated by FAP+ stromal cells, comprising administering to a patient in need thereof a therapeutically effective amount of a prodrug of an active agent, wherein the active agent is cytotoxic or inhibits protein expression or secretion to said FAP+ stromal cells, and is at least 2 fold more cytotoxic to the FAP+ stromal cells than the prodrug; and the prodrug (i) includes an FAP substrate sequence; (ii) is converted to the active agent by cleavage of the FAP substrate sequence by FAP, which substrate sequence has a $k_{cat}/K_m$ for cleavage by FAP at least 10 fold more than for cleavage by prolyl endopeptidase EC 3.4.21.26 (PREP); and (iii) is selectively converted in vivo to the active agent by FAP+ stromal cells.

Another aspect of the present invention relates to a method described herein, wherein the FAP substrate sequence has a $k_{cat}/K_m$ for cleavage by FAP at least 10 fold more than for cleavage by other S9 prolyl endopeptidases.

Another aspect of the present invention relates to a method described herein, wherein the prodrug is represented by formula V:

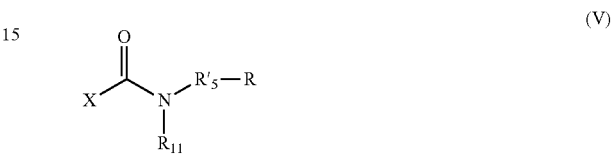

or a pharmaceutically acceptable salt thereof,
wherein
X—C(=O)NR$_{11}$—R'$_5$— represents the FAP substrate sequence, X is an N-acyl peptidyl group, —NR$_{11}$—R'$_5$ is an amino acid residue or analog thereof that binds the P'$_1$ specificity subsite of FAP, and the FAP substrate sequence is cleaved by FAP to release NHR$_{11}$—R'$_5$—R; R$_{11}$ represents H or lower alkyl; and
R'$_5$ and R taken together form the cytotoxic agent, or a moiety further metabolized at the site of the FAP+ stomal cells to form the cytotoxic agent.

Another aspect of the present invention relates to a method described herein, wherein the prodrug is represented by formula VI:

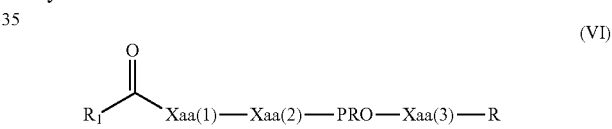

or a pharmaceutically acceptable salt thereof,
wherein
R$_1$—C(=O)— represents an acyl N-terminal blocking group;
Xaa(1) is an amino acid residue;
Xaa(2) is glycine, or a (D)-amino acid residue;
PRO represents a proline residue or an analog thereof;
Xaa(3) is a large hydrophobic amino acid residue; and
the prodrug is cleaved by FAP to release Xaa(3)-R, and Xaa(3)-R is the cytotoxic agent.

Another aspect of the present invention relates to a method described herein, wherein the prodrug is represented by formula VII:

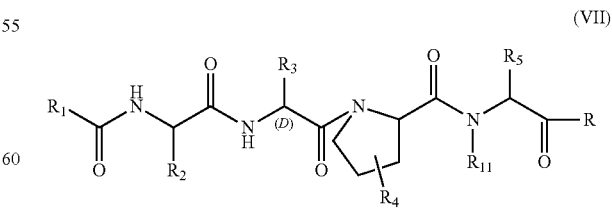

or a pharmaceutically acceptable salt thereof,
wherein
R$_1$—(C=O)— represents an acyl N-terminal blocking group;

$R_2$ represents H, lower alkyl, or a mono- or di-hydroxy-substituted lower alkyl;

$R_3$ represents H, halogen, or lower alkyl;

$R_4$ is absent or represents lower alkyl, —OH, —$NH_2$ or halogen;

$R_5$ represents a large hydrophobic amino acid sidechain;

$R_{11}$ represents H or lower alkyl; and the prodrug is cleaved by FAP to release the cytotoxic agent,

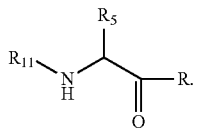

In certain embodiments, the acyl N-terminal blocking group is a moiety which, at physiological pH, reduces the cell permeability of said prodrug relative to said cytotoxic agent.

In certain embodiments, the acyl N-terminal blocking group is selected from the group consisting of formyl, acetyl, benzoyl, trifluoroacetyl, succinyl and methoxysuccinyl.

In certain embodiments, the acyl N-terminal blocking group includes one or more functional groups that are ionized at physiological pH.

In certain embodiments, the acyl N-terminal blocking group includes one or more carboxyl groups.

In certain embodiments, the acyl N-terminal blocking group is (lower alkyl)-C(=O)— substituted with one or more functional groups that are ionized at physiological pH.

In certain embodiments, the acyl N-terminal blocking group is selected from the group consisting of aryl($C_1$-$C_6$)acyl, and heteroaryl($C_1$-$C_6$)acyl.

In certain embodiments, the acyl N-terminal blocking group is an aryl($C_1$-$C_6$)acyl, wherein aryl($C_1$-$C_6$)acyl is a ($C_1$-$C_6$)acyl substituted with an aryl selected from the group consisting of benzene, naphthalene, phenanthrene, phenol and aniline.

In certain embodiments, the acyl N-terminal blocking group is an heteroaryl($C_1$-$C_6$)acyl, wherein heteroaryl($C_1$-$C_6$)acyl is a ($C_1$-$C_6$)acyl substituted with a heteroaryl selected from the group consisting of pyrrole, furan, thiophene, imidazole, oxazole, thiazole, triazole, pyrazole, pyridine, pyrazine, pyridazine and pyrimidine.

In certain embodiments, the acyl N-terminal blocking group is represented by the formula —C(=O)—($CH_2$)$_{1-10}$—C(=O)—OH.

In certain embodiments, the acyl N-terminal blocking group is succinyl.

In certain embodiments, at least one of Xaa(1), Xaa(2) and Xaa(3) is a non-naturally occurring amino acid analog.

Another aspect of the invention relates to a method described herein, wherein the cytotoxic agent is a proteasome inhibitor.

Another aspect of the invention relates to a method described herein, wherein the proteasome inhibitor is represented by formula VIII:

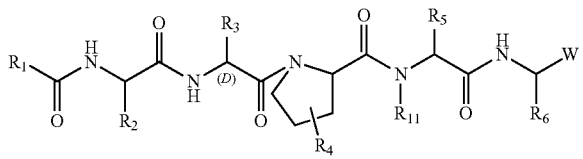

(VIII)

or a pharmaceutically acceptable salt thereof,
wherein
$R_1$—(C=O)— represents an acyl N-terminal blocking group;

$R_2$ represents H, lower alkyl, or a mono- or di-hydroxy-substituted lower alkyl;

$R_3$ represents H, halogen, or lower alkyl;

$R_4$ is absent or represents lower alkyl, —OH, —$NH_2$ or halogen;

$R_5$ represents a large hydrophobic amino acid sidechain;

$R_6$ is alkyl, cycloalkyl, aryl, heterocycle or —($CH_2$)$_n$—$R_7$;

$R_7$ is aryl, aralkyl, cycloalkyl, alkoxy, alkylthio, —OH or —SH;

$R_{11}$ represents H or lower alkyl;

W represents —CN, an epoxyketone, —CH=$NR_5$,

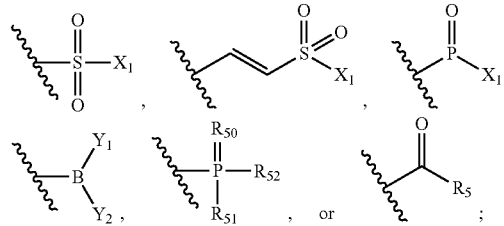

$R_8$ represents H, an alkyl, an alkenyl, an alkynyl, —C($X_1$)($X_2$)$X_3$, —($CH_2$)$_m$—$R_9$, —($CH_2$)$_n$—OH, —($CH_2$)$_n$—O-alkyl, —($CH_2$)—O-alkenyl, —($CH_2$)$_n$—O-alkynyl, —($CH_2$)$_n$—O—($CH_2$)$_m$—$R_9$, —($CH_2$)$_n$—SH, —($CH_2$)—S-alkyl, —($CH_2$)—S-alkenyl, —($CH_2$)—S-alkynyl, —($CH_2$)$_n$—S—($CH_2$)$_m$—$R_9$, —C(=O)C(=O)$NH_2$, —C(=O)C(=O)$OR_{10}$;

$R_9$ represents, independently for each occurrence, a substituted or unsubstituted aryl, aralkyl, cycloalkyl, cycloalkenyl, or heterocycle;

$R_{10}$ represents, independently for each occurrence, hydrogen, or a substituted or unsubstituted alkyl, alkenyl, aryl, aralkyl, cycloalkyl, cycloalkenyl, or heterocycle;

$Y_1$ and $Y_2$ can independently or together be OH, or a group capable of being hydrolyzed to a hydroxyl group, including cyclic derivatives where $Y_1$ and $Y_2$ are connected via a ring having from 5 to 8 atoms in the ring structure;

$R_{50}$ represents O or S;

$R_{51}$ represents $N_3$, $SH_2$, $NH_2$, $NO_2$ or —$OR_{10}$;

$R_{52}$ represents hydrogen, lower alkyl, amine, —$OR_{10}$, or a pharmaceutically acceptable salt, or $R_{51}$ and $R_{52}$ taken together with the phosphorous atom to which they are attached complete a heterocyclic ring having from 5 to 8 atoms in the ring structure;

$X_1$ is halogen;

$X_2$ and $X_3$ each represent H or halogen; and m is zero or an integer in the range of 1 to 8; and n is an integer in the range of 1 to 8.

In certain embodiments, the proteasome inhibitor is

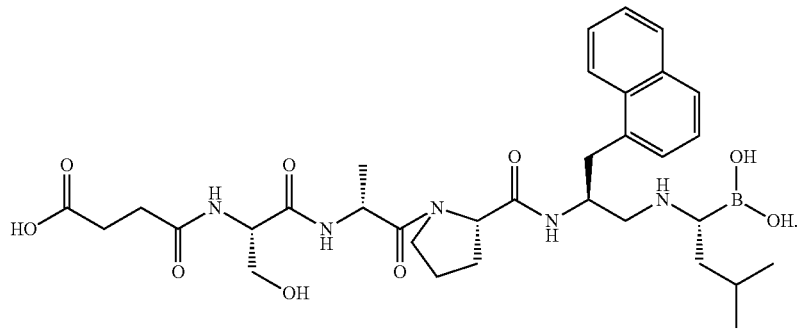 [SMILES: CC(C)C[C@H](NC[C@H](Cc1cccc2ccccc12)NC(=O)[C@@H]1CCCN1C(=O)[C@@H](C)NC(=O)[C@H](CO)NC(=O)CCC(=O)O)B(O)O]

In certain embodiments, the prodrug has a therapeutic index at least two times greater than the therapeutic index for the proteasome inhibitor when administered alone.

Another aspect of the invention relates to a method described herein, wherein the prodrug is administered as a single agent therapy.

Another aspect of the invention relates to a method described herein, wherein the prodrug is administered in a combination therapy with one or more anti-cancer agents.

Another aspect of the invention relates to a method described herein, wherein the anti-cancer agent is a covalent proteasome inhibitor.

Another aspect of the invention relates to a method described herein, wherein the anti-cancer agent is a chemotherapeutic.

Another aspect of the invention relates to a method described herein, wherein the chemotherapeutic is docetaxel, paclitaxel, imatinib mesylate, gemcitabine, cis-platin, carboplatin, 5-fluorouracil, pemetrexed, methotrexate, doxorubicin, lenalidomide, dexamethasone, or monomethyl auristatin.

Another aspect of the invention relates to a method described herein, wherein the chemotherapeutic is docetaxel, gemcitabine, carboplatin, or doxorubicin.

Another aspect of the invention relates to a method described herein, wherein the chemotherapeutic is MG-132, PSI, fellutamide B, bortezomib, CEP-18770, MLN-2238, MLN-9708, epoxomicin, carfilzomib (PR-171), NC-005, YU-101, LU-005, YU-102, NC-001, LU-001, NC-022, PR-957 (LMP7), CPSI (β5), LMP2-sp-ek, BODIPY-NC-001, azido-NC-002, ONX-0912, omuralide, PS-519, marizomib, belactosin A, $^{125}$I-NIP-L$_3$VS, NC-005-VS, or MV151.

Another aspect of the invention relates to a method described herein, wherein the anti-cancer agent is an immunotherapeutic agent.

Another aspect of the invention relates to a method described herein, wherein the immunotherapeutic agent is an anti-tumor antibody.

Another aspect of the invention relates to a method described herein, wherein the immunotherapeutic agent is a tumor antigen vaccine or anti-tumor dendritic cell vaccine.

Another aspect of the invention relates to the use of a compound described herein in the manufacture of a medicament for the treatment of a disorder for which inhibition of proteasome activity provides therapeutic benefit.

Another aspect of the invention relates to a packaged pharmaceutical, comprising a prodrug described herein formulated in a pharmaceutically acceptable excipient, in association with instructions (written and/or pictorial) describing the recommended dosage and/or administration of the formulation to a patient.

In certain embodiments, the compounds and compositions of the invention may also be combined with chemotherapy. The efficacy of chemotherapy—a mainstay of the standard of care in carcinoma—is limited by chemoresistance due to the activation of NF-κB by chemotherapeutic agents, resulting in inhibition of the apoptotic response of tumor cells. Tumor cells also resist chemotherapy by overexpression of Bcl-2 and P-glycoprotein. Proteasome inhibitors (PIs) counter these effects by repressing activation of NF-κB, inducing cleavage of Bcl-2 into proapoptotic fragments, and preventing maturation of P-glycoprotein into the active form that removes chemotherapeutic agents from the cancer cell. Therefore, PIs could act as adjuvants to chemotherapy. Compared to bortezomib in this role, the compounds and compositions disclosed herein may reduce compounded toxicities: e.g., increased grade ¾ hematologic toxicity associated with bortezomib plus gemcitabine, docetaxel or carboplatin. Chemotherapeutic agents are usually administered at high doses in cycles interspersed with breaks. More continuous administration of chemotherapeutic agents (metronomic chemotherapy) has recently been initiated in order to lengthen exposure of cancer cells to drug and inhibit angiogenesis. Due to reduced toxicity, the compounds and compositions disclosed herein would be ideally suited for longer periods of administration in combination with metronomic chemotherapy.

Definitions

The term "amino acid" is intended to encompass all compounds, whether natural or synthetic, which include both an amino functionality and an acid functionality, including amino acid analogues and derivatives. In certain embodiments, the amino acids contemplated in the present invention are those naturally occurring amino acids found in proteins, or the naturally occurring anabolic or catabolic products of such amino acids, which contain amino and carboxyl groups. Naturally occurring amino acids are identified throughout by the conventional three-letter and/or one-letter abbreviations, corresponding to the trivial name of the amino acid, in accordance with the following list. All amino acids described herein are contemplated as both (D)- and (L)-isomers unless otherwise designated. The abbreviations are accepted in the peptide art and are recommended by the IUPAC-IUB commission in biochemical nomenclature.

By the term "amino acid residue" is meant an amino acid. In general the abbreviations used herein for designating the naturally occurring amino acids are based on recommendations of the IUPAC-IUB Commission on Biochemical Nomenclature. See Biochemistry (1972) 11:1726-1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group.

The term "amino acid side chain" is that part of an amino acid residue exclusive of the backbone, as defined by K. D. Kopple, "Peptides and Amino Acids", W. A. Benjamin Inc., New York and Amsterdam, 1966, pages 2 and 33; examples of such side chains of the common amino acids are $-CH_2CH_2SCH_3$ (the side chain of methionine), $-CH_2(CH_3)-CH_2CH_3$ (the side chain of isoleucine), $-CH_2CH(CH_3)_2$ (the side chain of leucine) or H— (the side chain of glycine). These sidechains are pendant from the backbone Cα carbon.

The term "amino acid analog" refers to a compound structurally similar to a naturally occurring amino acid wherein the C-terminal carboxy group, the N-terminal amino group or side-chain functional group has been chemically modified. For example, aspartic acid-(beta-methyl ester) is an amino acid analog of aspartic acid; N-ethylglycine is an amino acid analog of glycine; or alanine carboxamide is an amino acid analog of alanine.

The phrase "protecting group" as used herein means substituents which protect the reactive functional group from undesirable chemical reactions. Examples of such protecting groups include esters of carboxylic acids and boronic acids, ethers of alcohols, and acetals and ketals of aldehydes and ketones. For instance, the phrase "N-terminal protecting group" or "amino-protecting group" as used herein refers to various amino-protecting groups which can be employed to protect the N-terminus of an amino acid or peptide against undesirable reactions during synthetic procedures. Examples of suitable groups include acyl protecting groups such as, to illustrate, formyl, dansyl, acetyl, benzoyl, trifluoroacetyl, succinyl, and methoxysuccinyl; aromatic urethane protecting groups as, for example, benzyloxycarbonyl (Cbz); and aliphatic urethane protecting groups such as t-butoxycarbonyl (Boc) or 9-Fluorenylmethoxycarbonyl (Fmoc).

The term "amino-terminal protecting group" as used herein, refers to terminal amino protecting groups that are typically employed in organic synthesis, especially peptide synthesis. Any of the known categories of protecting groups can be employed, including acyl protecting groups, such as acetyl, and benzoyl; aromatic urethane protecting groups, such as benzyloxycarbonyl; and aliphatic urethane protecting groups, such as tert-butoxycarbonyl. See, for example, Gross and Mienhoffer, Eds., *The Peptides*, Academic Press: New York, 1981; Vol. 3, 3-88; and Green, T. W.; Wuts, P. G. M., *Protective Groups in Organic Synthesis,* 2nd ed, Wiley: New York, 1991. Preferred protecting groups include aryl-, aralkyl-, heteroaryl- and heteroarylalkyl-carbonyl and sulfonyl moieties.

As used herein the term "physiological conditions" refers to temperature, pH, ionic strength, viscosity, and like biochemical parameters which are compatible with a viable organism, and/or which typically exist intracellularly in a viable mammalian cell The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salts" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. See, for example, Berge et al. (1977) "Pharmaceutical Salts", *J. Pharm. Sci.* 66:1-19.

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A "therapeutically effective amount" of a compound with respect to use in treatment, refers to an amount of the compound in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "self-eliminating linker" or "self-immolative linker" refers to a temporary extender, spacer, or placeholder unit attaching two or more molecules together by chemical bonds that are cleaved under defined conditions to release the two molecules. Examples of self-eliminating linkers include, but are not limited to, p-aminobenzyloxycarbonyl (PABC) and 2,4-bis(hydroxymethyl)aniline. The self-eliminating or self-immolative linker may be linear or branched, and may link two or more of the same molecules together, or may link two or more different molecules together. The self-eliminating or self-immolative linker may degrade, decompose, or fragment under, for example, physiological conditions, acidic conditions, basic conditions, or in the presence of specific chemical agents.

As noted above, certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis or by derivation with a chiral auxiliary, where the resulting diastereomeric mixture is separated and the auxiliary group cleaved to provide the pure desired enantiomer. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomer.

An aliphatic chain comprises the classes of alkyl, alkenyl and alkynyl defined below. A straight aliphatic chain is limited to unbranched carbon chain moieties. As used herein, the term "aliphatic group" refers to a straight chain, branched-chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer.

"Cycloalkyl" means mono- or bicyclic or bridged saturated carbocyclic rings, each having from 3 to 12 carbon atoms. Likewise, preferred cycloalkyls have from 5-12 carbon atoms in their ring structure, and more preferably have 6-10 carbons in the ring structure.

Unless the number of carbons is otherwise specified, "lower alkyl," as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In certain embodiments, a substituent designated herein as alkyl is a lower alkyl.

"Alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located any where in the moiety and can have either the (Z) or the (E) configuration about the double bond(s).

"Alkynyl" refers to hydrocarbyl moieties of the scope of alkenyl, but having one or more triple bonds in the moiety.

The term "alkylthio" refers to an alkyl group, as defined above, having a sulfur moiety attached thereto. In certain embodiments, the "alkylthio" moiety is represented by one of —(S)-alkyl, —(S)-alkenyl, —(S)-alkynyl, and —(S)—$(CH_2)_m$—$R^1$, wherein m and $R^1$ are defined below. Representative alkylthio groups include methylthio, ethylthio, and the like.

The terms "alkoxyl" or "alkoxy" as used herein refers to an alkyl group, as defined below, having an oxygen moiety attached thereto. Representative alkoxyl groups include methoxy, ethoxy, propoxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O— alkenyl, —O-alkynyl, —O—$(CH_2)_m$—$R^1$, where m and $R_1$ are described below.

The terms "amine" and "amino" are art-recognized and refer to both unsubstituted and substituted amines, e.g., a moiety that can be represented by the formulae:

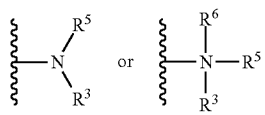

wherein $R^3$, $R^5$ and $R^6$ each independently represent a hydrogen, an alkyl, an alkenyl, $-(CH_2)_m-R^1$, or $R^3$ and $R^5$ taken together with the N atom to which they are attached complete a heterocycle having from 4 to 8 atoms in the ring structure; $R^1$ represents an alkenyl, aryl, cycloalkyl, a cycloalkenyl, a heterocyclyl, or a polycyclyl; and m is zero or an integer in the range of 1 to 8. In certain embodiments, only one of $R^3$ or $R^5$ can be a carbonyl, e.g., $R^3$, $R^5$, and the nitrogen together do not form an imide. In even more certain embodiments, $R^3$ and $R^5$ (and optionally $R^6$) each independently represent a hydrogen, an alkyl, an alkenyl, or $-(CH_2)_m-R^1$. Thus, the term "alkylamine" as used herein means an amine group, as defined above, having a substituted or unsubstituted alkyl attached thereto, i.e., at least one of $R_3$ and $R_5$ is an alkyl group. In certain embodiments, an amino group or an alkylamine is basic, meaning it has a conjugate acid with a $pK_a \geq 7.00$, i.e., the protonated forms of these functional groups have $pK_a$s relative to water above about 7.00.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Preferably, aryl groups include 5- to 12-membered rings, more preferably 6- to 10-membered rings The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carboycyclic aryl groups include benzene, naphthalene, phenanthrene, phenol, aniline, and the like. Heteroaryl groups include substituted or unsubstituted aromatic 3- to 12-membered ring structures, more preferably 5- to 12-membered rings, more preferably 6- to 10-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like.

The terms "heterocyclyl" or "heterocyclic group" refer to 3- to 12-membered ring structures, more preferably 5- to 12-membered rings, more preferably 6- to 10-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, $-CF_3$, $-CN$, and the like.

The term "carbonyl" is art-recognized and includes such moieties as can be represented by the formula:

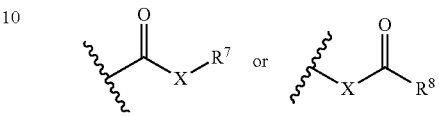

wherein X is a bond or represents an oxygen or a sulfur, and $R^7$ represents a hydrogen, an alkyl, an alkenyl, $-(CH_2)_m-R^1$ or a pharmaceutically acceptable salt, $R^8$ represents a hydrogen, an alkyl, an alkenyl or $-(CH_2)_m-R^1$, where m and $R^1$ are as defined above. Where X is an oxygen and $R^7$ or $R^8$ is not hydrogen, the formula represents an "ester." Where X is an oxygen, and $R^7$ is as defined above, the moiety is referred to herein as a carboxyl group, and particularly when $R^7$ is a hydrogen, the formula represents a "carboxylic acid". Where X is an oxygen, and $R^8$ is a hydrogen, the formula represents a "formate." In general, where the oxygen atom of the above formula is replaced by a sulfur, the formula represents a "thiocarbonyl" group. Where X is a sulfur and $R^7$ or $R^8$ is not hydrogen, the formula represents a "thioester" group. Where X is a sulfur and $R^7$ is a hydrogen, the formula represents a "thiocarboxylic acid" group. Where X is a sulfur and $R^8$ is a hydrogen, the formula represents a "thioformate" group. On the other hand, where X is a bond, and $R^7$ is not hydrogen, the above formula represents a "ketone" group. Where X is a bond, and $R^7$ is a hydrogen, the above formula represents an "aldehyde" group.

The term "thioxamide," as used herein, refers to a moiety that can be represented by the formula:

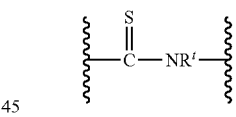

in which $R^t$ is selected from the group consisting of the group consisting of hydrogen, alkyl, cycloalkyl, aralkyl, or aryl, preferably hydrogen or alkyl. Moreover, "thioxamide-derived" compounds or "thioxamide analogues" refer to compounds in which one or more amide groups have been replaced by one or more corresponding thioxamide groups. Thioxamides are also referred to in the art as "thioamides."

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "nitro" means —NO₂; the term "halogen" designates —F, —Cl, —Br, or —I; the term "sulfhydryl" means —SH; the term "hydroxyl" means —OH; the term "sulfonyl" means —SO₂—; the term "azido" means —N₃; the term "cyano" means —CN; the term "isocyanato" means —NCO; the term "thiocyanato" means —SCN; the term "isothiocyanato" means —NCS; and the term "cyanato" means —OCN.

The term "sulfamoyl" is art-recognized and includes a moiety that can be represented by the formula:

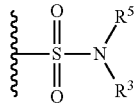

in which R³ and R⁵ are as defined above.

The term "sulfate" is art recognized and includes a moiety that can be represented by the formula:

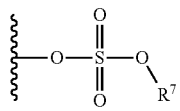

in which R⁷ is as defined above.

The term "sulfonamide" is art recognized and includes a moiety that can be represented by the formula:

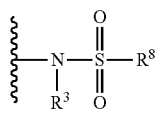

in which R³ and R⁸ are as defined above.

The term "sulfonate" is art-recognized and includes a moiety that can be represented by the formula:

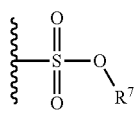

in which R⁷ is an electron pair, hydrogen, alkyl, cycloalkyl, or aryl.

The terms "sulfoxido" or "sulfinyl", as used herein, refers to a moiety that can be represented by the formula:

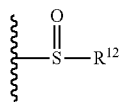

in which R¹² is selected from the group consisting of the group consisting of hydrogen, alkyl, alkenyl, alkynyl, cycloalkyl, heterocyclyl, aralkyl, or aryl.

As used herein, the definition of each expression, e.g., alkyl, m, n, etc., when it occurs more than once in any structure, is intended to be independent of its definition elsewhere in the same structure.

For purposes of this invention, the chemical elements are identified in accordance with the Periodic Table of the Elements, CAS version, *Handbook of Chemistry and Physics,* 67th ed., 1986-87, inside cover.

EXEMPLIFICATION

The invention now being generally described, it will be more readily understood by reference to the following examples, which are included merely for purposes of illustration of certain aspects and embodiments of the present invention, and are not intended to limit the invention.

Example 1. ARI-3996 and Proteasome Inhibitors of the Invention

ARI-3996 and its PI warhead ARI-2727D were synthesized as shown in FIG. 1, using synthetic and analytical methods previously described for obtaining peptide boronic acids. Bortezomib was purchased from Selleck Chemicals or ChemieTek. Each batch of ARI-3996 was validated for selective cleavage by FAP versus PREP as described herein.

The following reagents were used: (a) HATU/DMF/DIPEA, 95% yield; (b) 4 M HCl in dioxane, 100% yield; (c) HATU/DMF/DIPEA, 90% yield; (d) 4M HCl in dioxane, 100% yield; (e) tBu-Suc-Ser(tBu)-OH, HATU/DMF/DIPEA, 90% yield; (f) Pd(OH)₂—C/H₂/methanol, 90% yield; (g) 2727D, HATU/DMF/DIPEA, 85% yield; (h) TFA/DCM, 90% yield; (i) PhB(OH)₂, pentane-water-acetonitrile, 70% yield. The chemical synthesis of peptides, particularly short peptides such as di- and tripeptides such as those described herein, is well-known in the art and sufficiently predictable due to its modular nature. Therefore the synthetic methods of Table 1 or standard solid-phase synthetic methods as applied to peptides would be successful in delivering any compound of formula I.

Figure 15:
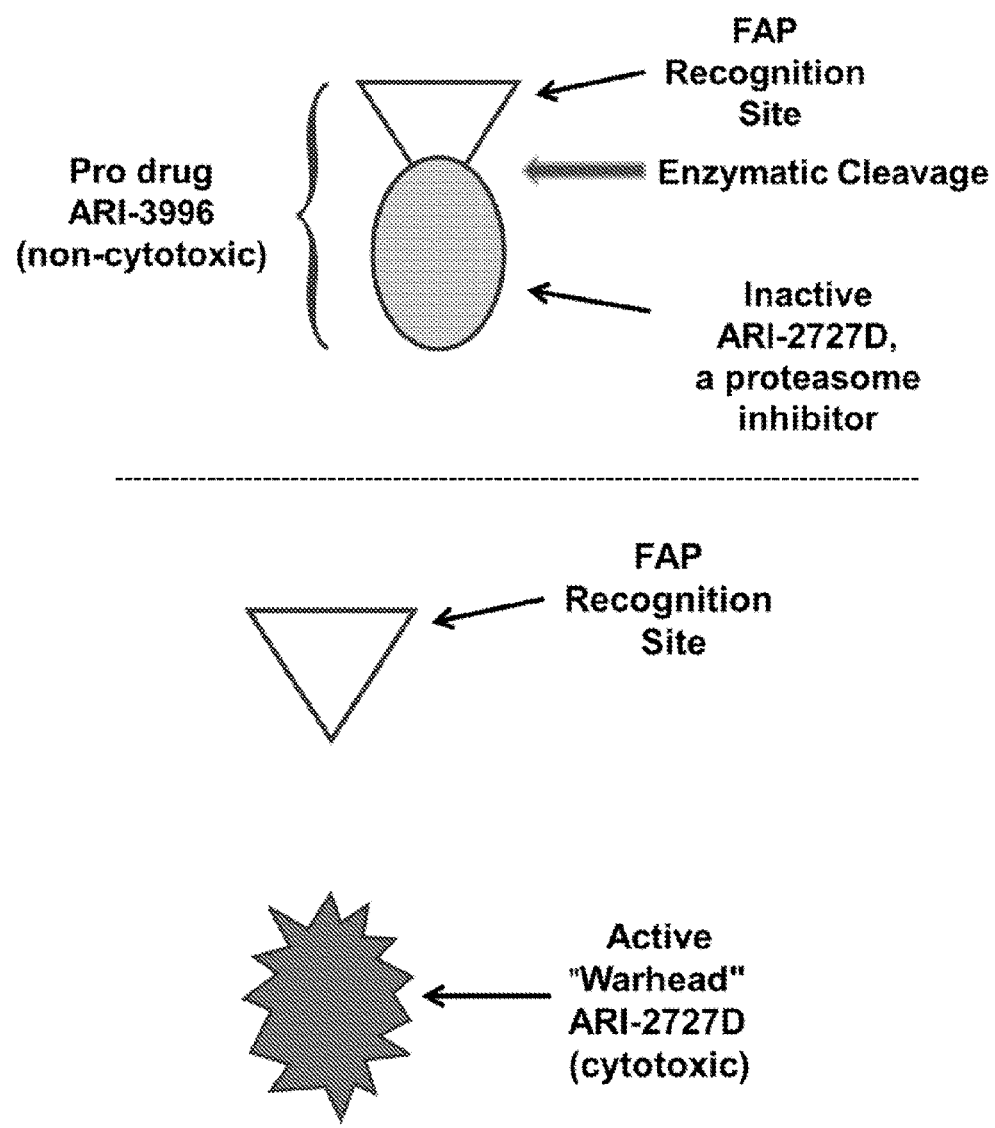
FIG. 15 shows a cartoon of the prodrug ARI-3996, which contains a FAP recognition site chemically bound to ARI-2727D, a proteasome inhibitor which remains inactive while bound to the FAP recognition site (top) and a cartoon of what takes place after cleavage by FAP; the active "warhead" ARI-2727D is released from the FAP recognition site (bottom).

ARI-3996 is a pro-drug version of a bortezomib-like cytotoxic agent designed to more selectively target the proteasome in solid tumors (FIG. 15). ARI-3996 was designed to reduce the mechanism-based DLTs associated with proteasome inhibition by remaining inactive until it is cleaved by fibroblast activation protein (FAP) on the surface of reactive stromal fibroblasts of epithelial tumors. Because FAP is produced in epithelial tumors but not usually in healthy tissues (FAP is expressed in the stroma of many common epithelial tumors-lung, colon, breast and pancreatic cancer), ARI-3996 should not be activated in nervous tissue or in bone marrow where platelets are generated. ARI-3996 is relatively non-toxic to all cells and cannot kill tumor cells until it is activated by FAP. Therefore, ARI-3996 should kill FAP-producing tumors with less severe PN and thrombocytopenia than that associated with bortezomib.

Fibroblast activation protein (FAP) is a post-prolyl cleaving serine protease belonging to the (dipeptidyl peptidase) DPP-IV-like subfamily in which FAP and prolyl endopeptidase (PREP) are the only mammalian proteases that can cleave on the C-terminal side of internal proline. Unlike FAP, PREP is constitutively and ubiquitously expressed. We have solved the specificity problem of FAP versus PREP cleavage required to make a pro-drug selectively activated by FAP.

Figure 2:
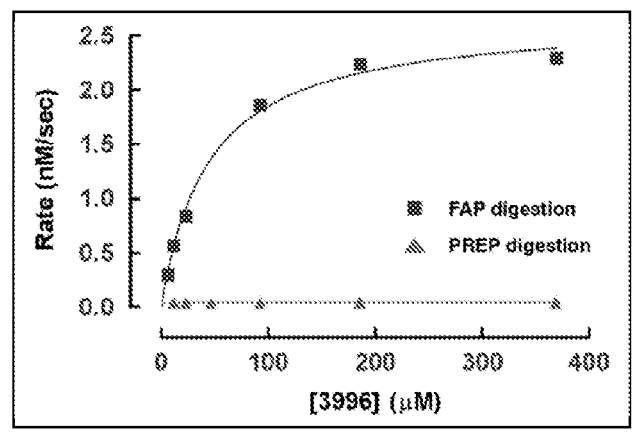
FIG. 2 shows the rate of in vitro cleavage of ARI-3996 by FAP and PREP as a function of the concentration of ARI-3996. Cleavage was monitored by assay of release of "warhead" ARI-2727 using LCMS.

FAP's $P_4$-$P_1$ cleavage specificity requires proline at $P_1$, glycine or D-amino acids at $P_2$, prefers small uncharged amino acids at $P_3$, and tolerates most amino acids at $P_4$. We have discovered that D-alanine at $P_2$ allows cleavage by FAP as expected but prevents cleavage by PREP. Thus, linkage of the tripeptide Suc-Ser-D-Ala-Pro by a C-terminal peptide bond to the bortezomib-like aminoboronate dipeptide Ala (1-Nal)-boroLeu (ARI-2727D) produces the pro-drug ARI-3996 in which the proteasome inhibitory activity is unleashed selectively by FAP cleavage of the Pro-Ala(1-Nal) bond. In vitro, ARI-3996 is cleaved by FAP, but to a far lesser extent by PREP, to yield the cytotoxic "warhead" ARI-2727D as demonstrated by mass spectrometry (FIG. 2) and by assay of tumor-cell killing in vitro by fluorescent cell-titer blue (Promega) (Table 1).

TABLE 1

FAP specifically activates ARI-3996 to kill tumor cells in vitro

| | Cytotoxic $EC_{50}{}^a$ ($\mu$M) of ARI-3996 incubated with[b]: | | |
|---|---|---|---|
| Cell line | None | FAP | PREP |
| RPMI 8226 | 5.8 | 0.16 | 3.1 |
| KG-1 | 22.0 | 0.30 | 13.0 |
| RPMI 1788 | 6.2 | 0.13 | 3.6 |
| BxPC-3 | 34.0 | 0.80 | 21.0 |

[a]Drug concentrations that kills 50% of cells.
[b]24 hours at 37° C. except BxPC-3, 48 hours Example 2. Use of ARI-3144 as a Diagnostic/Patient Stratification Tool

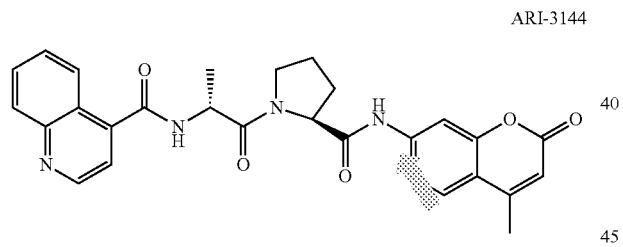

ARI-3144

Figure 11:
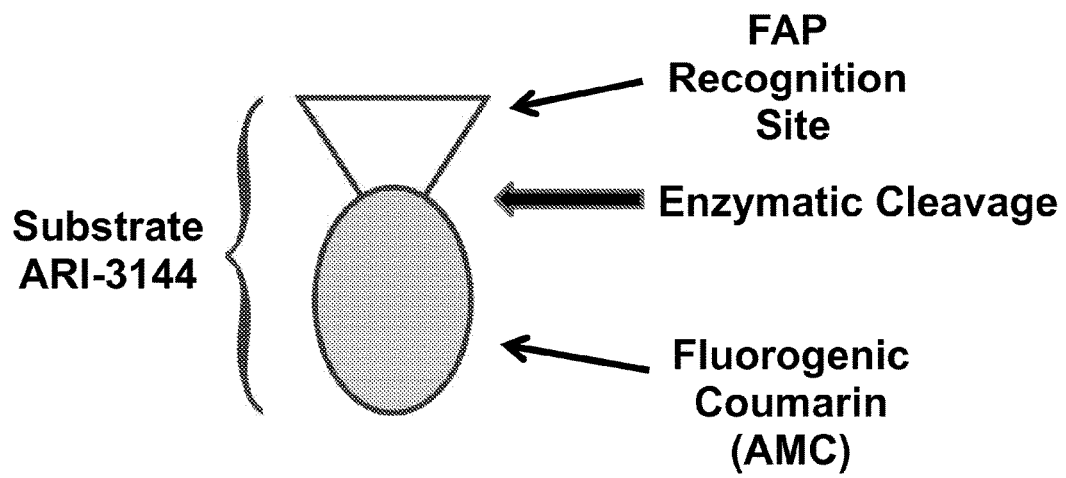
FIG. 11 shows a cartoon of diagnostic fluorogenic substrate ARI-3144. The FAP recognition site binds specifically to FAP and is cleaved by the enzyme to release the fluorogenic coumarin moiety.
Figure 12:
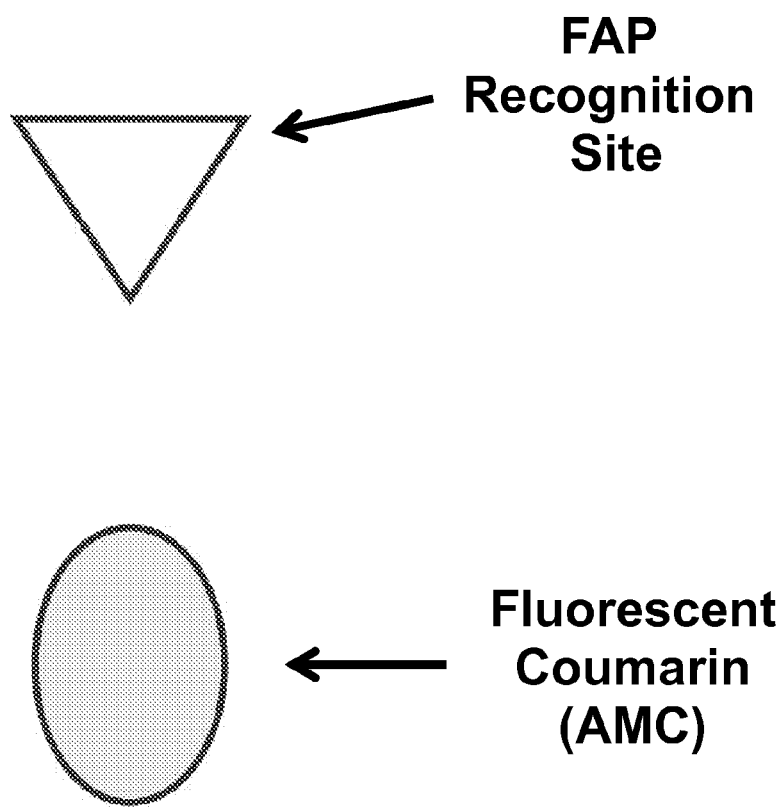
FIG. 12 shows a cartoon of ARI-3144 after binding to FAP. The FAP recognition site is cleaved to release the fluorescent coumarin moiety.

The structure of ARI-3144 is shown above and includes an arrow indicating the chemical bond that is cleaved by FAP. FIG. 11 shows a cartoon of the concept underlying the diagnostic use of this compound. The FAP recognition site is chemically attached to the fluorogenic coumarin (AMC) moiety. After binding of ARI-3144 to FAP, chemical bond cleavage takes place (FIG. 12) to release the FAP recognition site from the AMC. Once released, AMC is now fluorescent and its concentration can be quantified by measuring its spectroscopic properties.

Figure 3:
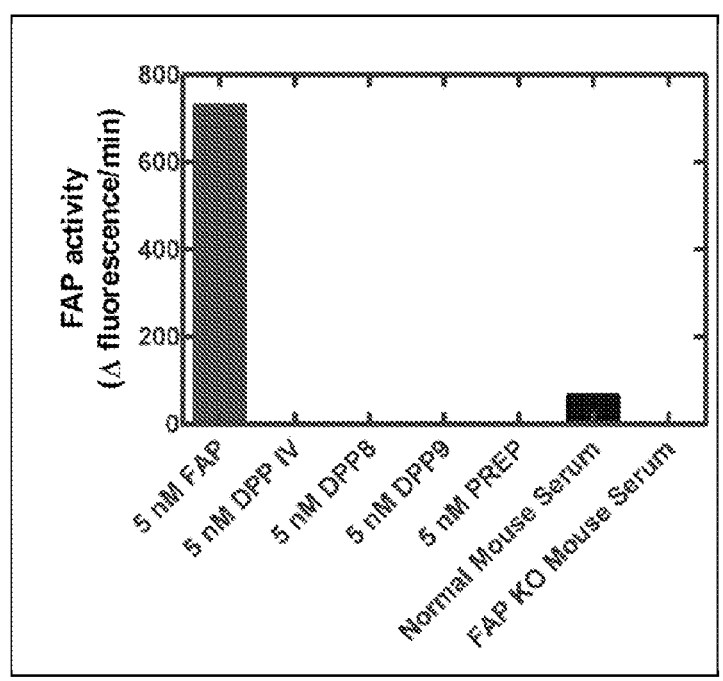
FIG. 3 shows in vitro cleavage of ARI-3144 ((N-Quinoline-4-carbonyl)-D-Ala-Pro-AMC) by FAP, but not by DPP IV, DPP 8, DPP 9 or PREP. Cleavage was monitored by measuring fluorescence of the AMC leaving group (excitation, 355 nm; emission, 460 nm).
Figure 13:
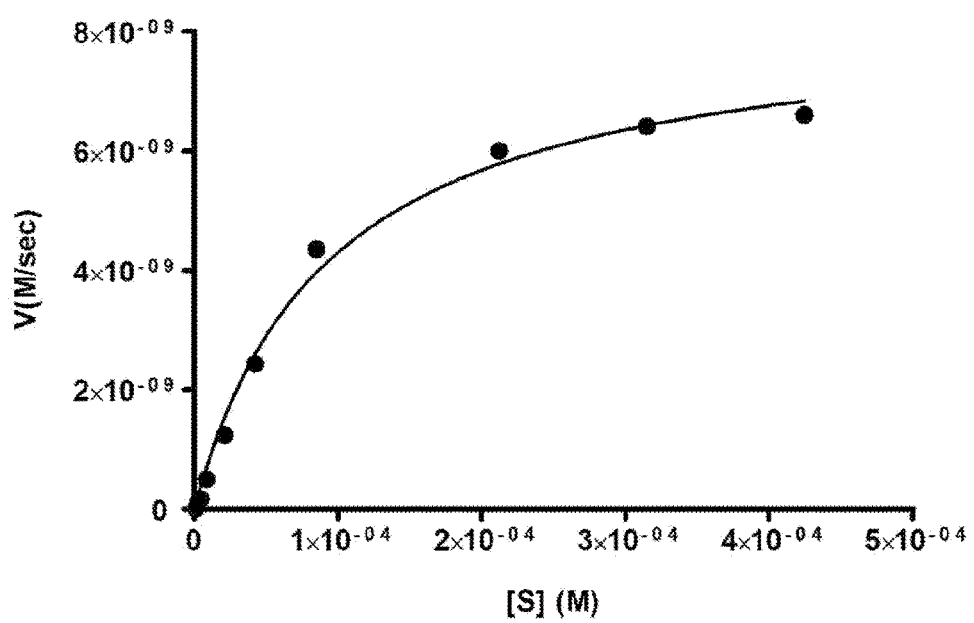
FIG. 13 shows that ARI-3144 is an excellent substrate for FAP.
Figure 14:
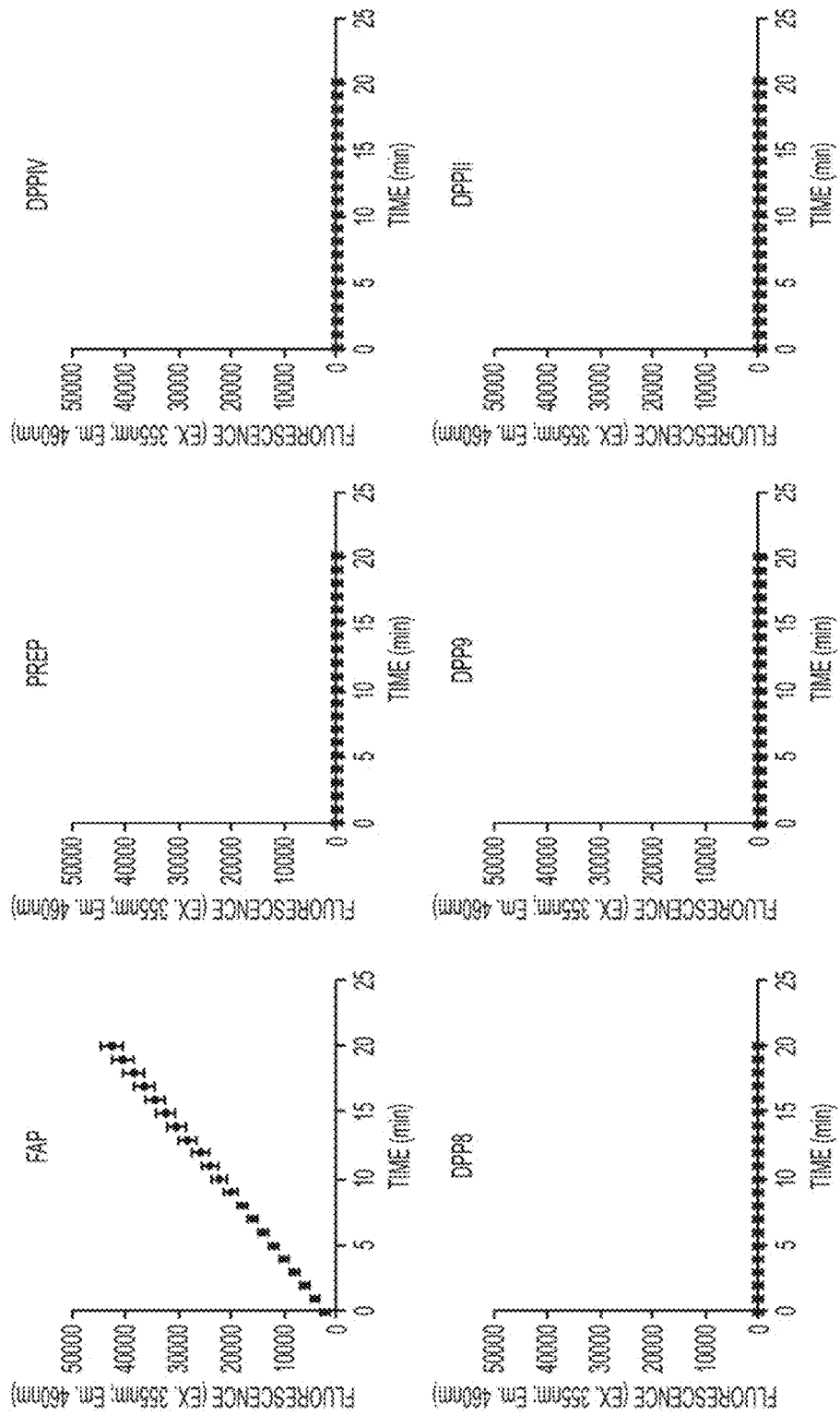
FIG. 14 shows fluorescence measurements of the rate of ARI-3144 cleavage by PREP, DPPIV, DPP8, DPP9, and DPPII. ARI-3144 is highly selective for FAP.

The D-alanine at $P_2$ of the fluorogenic substrate, N-(Quinoline-4-carbonyl)-D-Ala-Pro-AMC [AMC=7-amino-4-methylcoumarin] (ARI-3144), confers selectivity for FAP so that it is cleaved to release fluorescent AMC by recombinant FAP but not by other DPP-IV-like proteases (FIG. 3). As shown in FIG. 13, ARI-3144 is an excellent substrate for FAP, and no cleavage by PREP, DPPIV, DPP8, DPP9, or DPPII was detected (FIG. 14). FAP is reportedly not expressed constitutively in healthy tissue with the exception of endometrium, although FAP proteolytic activity is detectable in plasma. Ovarian and prostate tumors excepted, induction of FAP expression in stromal fibroblasts of common epithelial tumors (lung, colon, breast and pancreas) has been demonstrated by immunohistochemistry and mRNA analysis. The ability to measure FAP proteolytic activity in tumors is required to evaluate the usefulness of ARI-3996 as a chemotherapeutic agent. Hitherto, FAP activity has not been quantified in human or mouse tumors. We have used the ARI-3144 assay ex vivo to demonstrate increased FAP proteolytic activity in human pancreatic carcinoma relative to healthy tissues and plasma. We will use the assay to select a mouse tumor model for investigation of ARI-3996's activity in which the increase in tumor-associated FAP activity relative to plasma is equivalent to that in human epithelial cancer.

Besides coumarin-based chromophores, other widely-used chromophores would work just as well as long as an amide linkage could be used for attachment (i.e., the chromophore has a primary amino group available for attachment to the proline of the FAP recognition site. Such commonly-used chromophores are, for example:

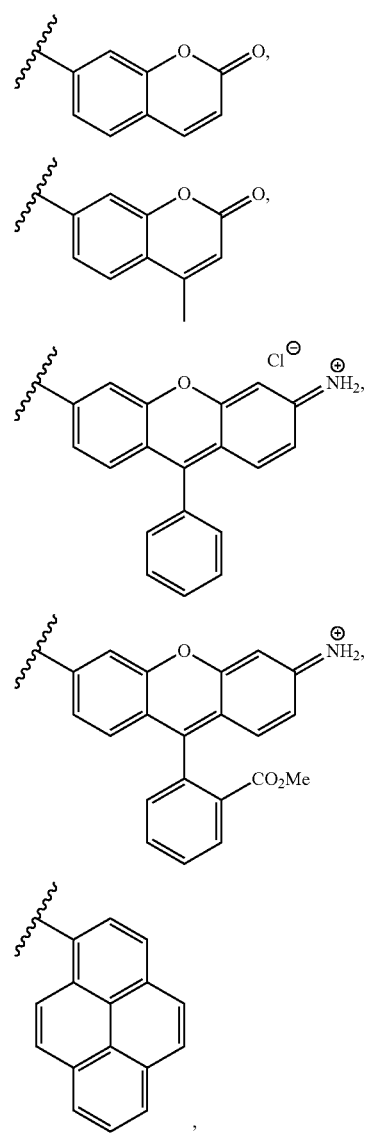

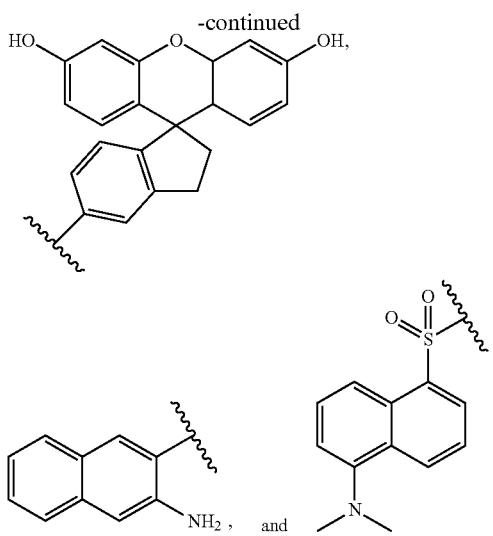

Example 3. Mouse Model of Epithelial Cancer in which the FAP Proteolytic Activity of Tumor Tissue is Equivalent to that in Human Cancer Patients The FAP-specific fluorogenic substrate ARI-3144 was used to measure FAP proteolytic activity in tissue homogenates and plasma in a standard continuous fluorometric assay as previously described.

Figure 4:
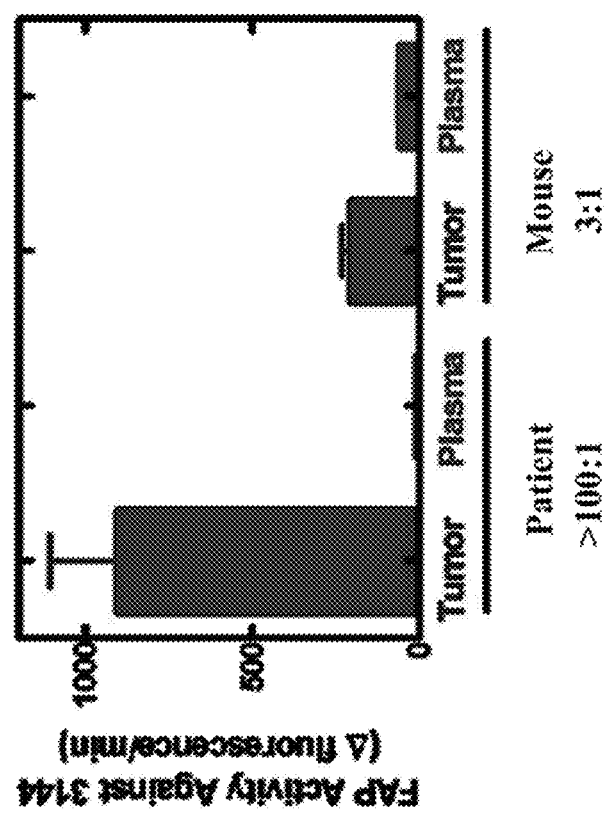
FIG. 4 shows the ratio of FAP proteolytic activity in humans and mice for pancreatic tumor tissue and plasma. FAP activity was assayed ex vivo in tumor homogenates and plasma using ARI-3144 fluorogenic substrate.
Figure 16:
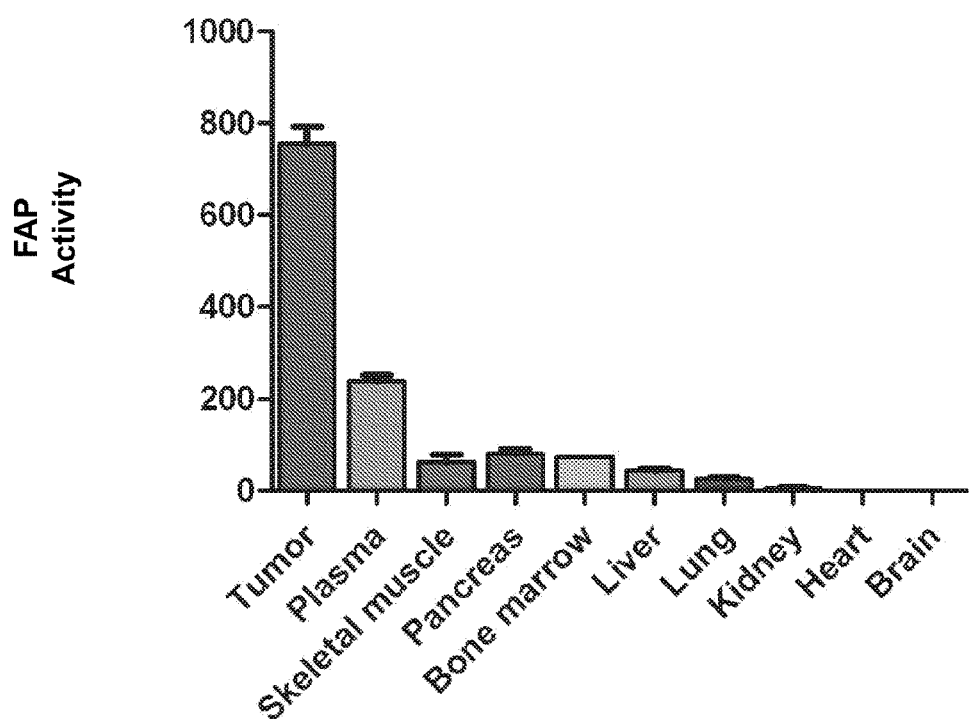
FIG. 16 shows FAP activity in cancerous and normal mouse tissues. The much higher FAP activity in and around the tumor indicates that FAP is upregulated in that tissue.

In tissue specimens from 14 pancreatic cancer patients at the Fox Chase Cancer Center, we determined mean (±SE) FAP activity in cancerous tissue of 903.7±161.4 expressed as change in fluorescent units (ΔFU)/min/mg protein. FAP activity varied between patients with 4 high-expressers that were in the range of 1,200 to 3,000. In contrast, HPAF-II pancreatic adenocarcinoma xenografts in scid mice exhibited mean activity of only 200±12.5. In mice, we have found that circulating levels of plasma FAP activity are approximately 6-fold higher than in humans regardless of whether either species bears a tumor. Thus, the tumor:plasma ratio of FAP activity is at least 100:1 in humans; but only 3:1 in the HPAFII xenografted mice (FIGS. 4 and 16).

Figure 17:
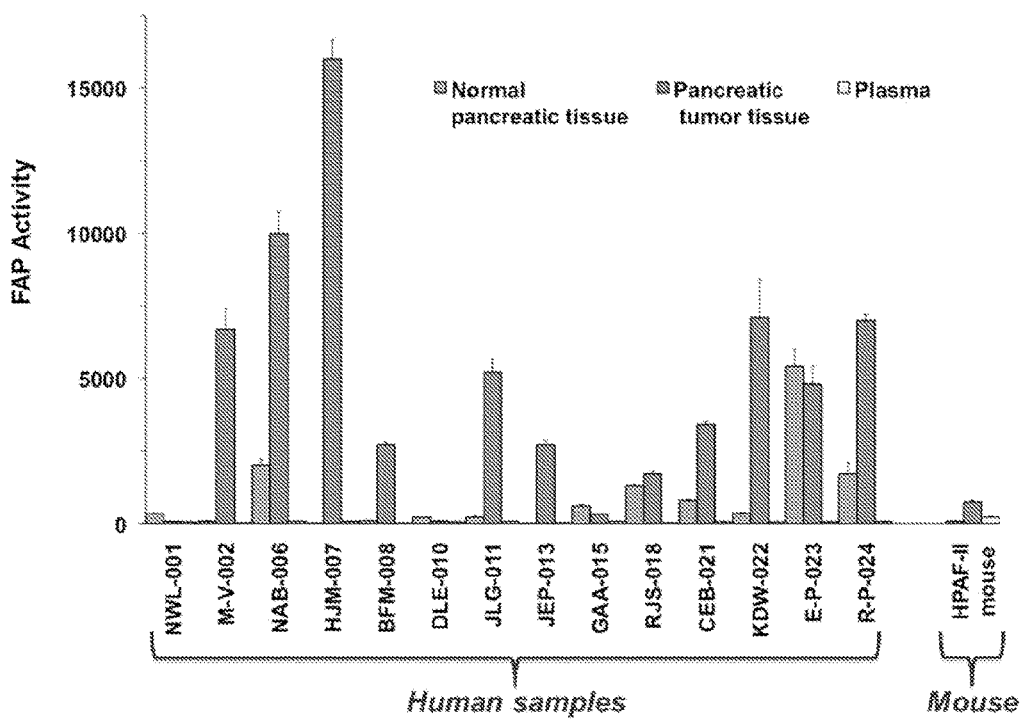
FIG. 17 shows FAP activity in human tumor cell lines and HPAF-II mouse tumor xenografts. FAP activity is generally higher in human tumor cell lines than mouse tumor xenografts. FAP activity is likely to be even higher than shown due to some deactivation of FAP during sample collection and handling.

The TI of a FAP-activated pro-drug such as ARI-3996 is expected to depend on the difference between the systemic level of FAP proteolytic activity and the level in tumor tissue. ARI-3996 has exhibited significant antitumor activity in HPAF-II mice (see below). However, the HPAF-II model does not accurately reflect the tumor:systemic ratio of FAP activity in human pancreatic carcinoma patients (FIGS. 16 and 17). In order to test the feasibility of ARI-3996 as a safer and more effective PI than bortezomib in solid cancer, a carcinoma model in which tumor FAP activity is ~35-fold higher than in HPAF-II xenografts is needed. Because FAP is induced in reactive stromal fibroblasts during tumorigenesis, the level of tumor FAP activity should be higher in mouse models that recapitulate the pattern of stromal development in human cancer than in xenografts of cell lines. Two different models appear promising. In the Cre-recombinase inducible lung adenocarcinoma model in Lox-Stop-Lox (LSL)-K-ras$^{G12D}$ mice, endogenous tumor development induces a FAP$^+$ stroma that closely resembles that in human carcinoma histologically. An alternative model is provided by patient tumors directly transplanted into immunodeficient mice. The transplanted human tumors are reported to maintain the stromal organization and vasculature of the original tumor. FAP activity will be assayed in samples of xenograft transplants of human epithelial carcinomas with well-developed stroma provided by Oncotest http://www.oncotest.de/for-pharma/index.php.

Figure 5:
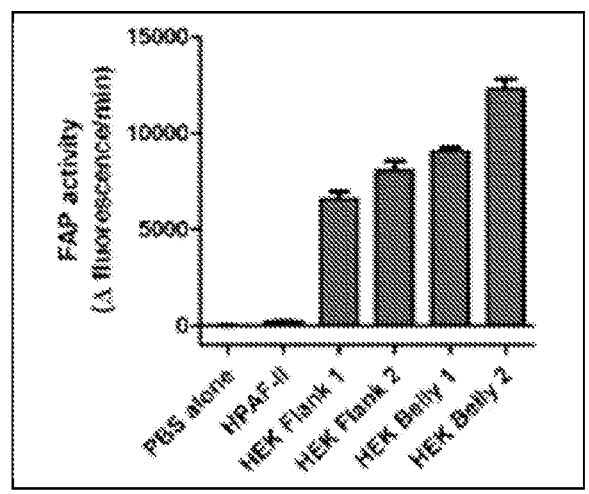
FIG. 5 shows FAP proteolytic activity in xenografts of FAP-transfected HEK293 cells and HPAF-11 cells. FAP activity was assayed using the ARI-3144 assay.

As shown in FIG. 5, the FAP transfected HEK293 xenograft model can be used to model human tumors overexpressing FAP to a similar degree as in tumors found in human cancer patients. A FAP-transfected variant of the HEK293 cell line forms tumors of FAP$^+$ epithelial cells in scid mice (69). We have demonstrated FAP activity levels of 6,000 to 12,500 ΔFU/min/mg in FAP-HEK293 tumors in vivo (FIG. 5). The FAP-HEK293 model is, therefore, suitable for investigation of ARI-3996's TI. However, unlike the K-ras$^{G12D}$-driven lung tumor and direct patient transplant models, the HEK293 model does not mimic the stromal expression of FAP in human carcinoma.

Figure 18:
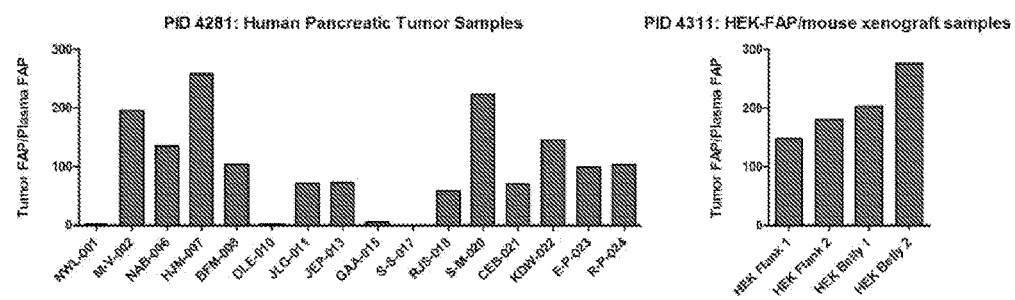
FIG. 18 shows a graph of FAP activity in several tissues. FAP transfected HEK tumor xenografts match human pancreatic tumor tissue for FAP content.

Furthermore, as shown in FIG. 18, FAP transfected HEK tumor xenografts have FAP activity matching human pancreatic cancer tumors. A battery of human pancreatic tumor samples had FAP activity levels ranging from negligible to over 250 (tumor FAP/plasma FAP). The right hand side of FIG. 18 shows that HEK mouse xenograft samples display ratios of tumor FAP/plasma FAP from 150-270.

Example 4. Validation of the HEK Tumor Xenograft Mouse Model

Figure 20:
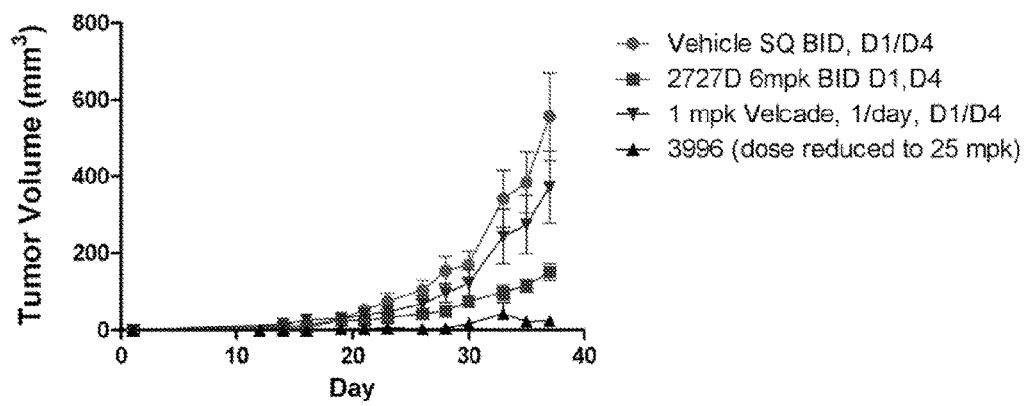
FIG. 20 shows the anticancer activity of ARI-3996 in FAP-transfected HEK tumor xenograft.
Figure 20:
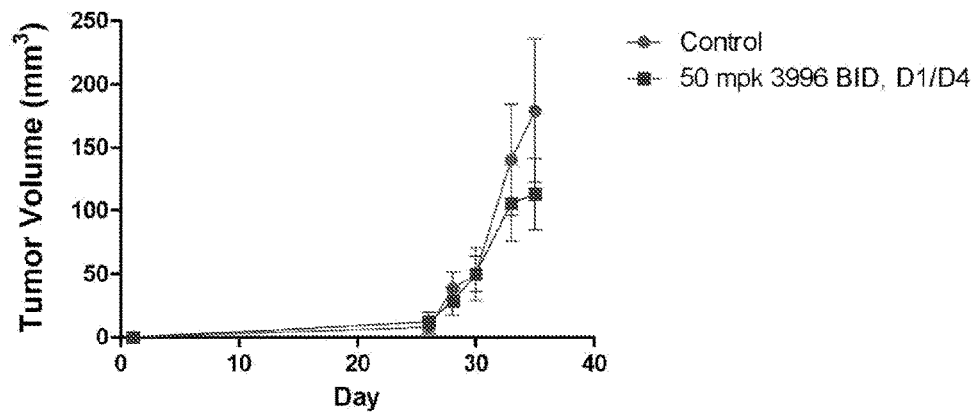

Having determined the levels of FAP expression in the HEK xenograft model, the anticancer activity of ARI-3996 was next evaluated in a 40-day study. FIG. 20 shows the results. Impressively, while Velcade® hardly slowed the growth of the tumors, both ARI-2727D and ARI-3996 exhibited potent tumor inhibition. ARI-2727D is expected to be less potent than ARI-3996 because it lacks the FAP recognition site, or address moiety. It also suffers conformation-dependent inactivation over time. Nonetheless, ARI-2727 showed a markedly greater inhibitory effect than Velcade®.

At a dose of 25 mg/kg, ARI-3996 showed nearly complete inhibition of tumor growth. Even in an HEK-mock model (FIG. 20 bottom) at a dose of 50 mg/kg ARI-3996 was well tolerated and showed an inhibitory effect over the control.

Figure 19:
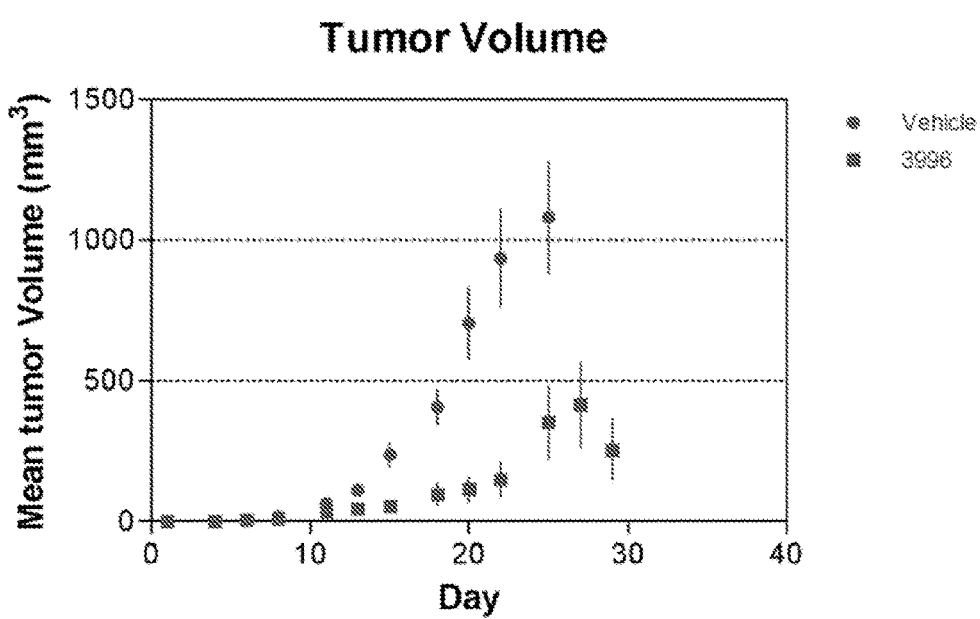
FIG. 19 shows the mean tumor volume of mice treated with either a vehicle control or with ARI-3996. ARI-3996 induces tumor regression in immunocompetent mice.

As a further test of its efficacy, ARI-3996 was administered to immunocompetent WT BALB/c mice. As FIG. 19 shows, tumor regression was observed over the course of a 30-day experiment.

Figure 6:
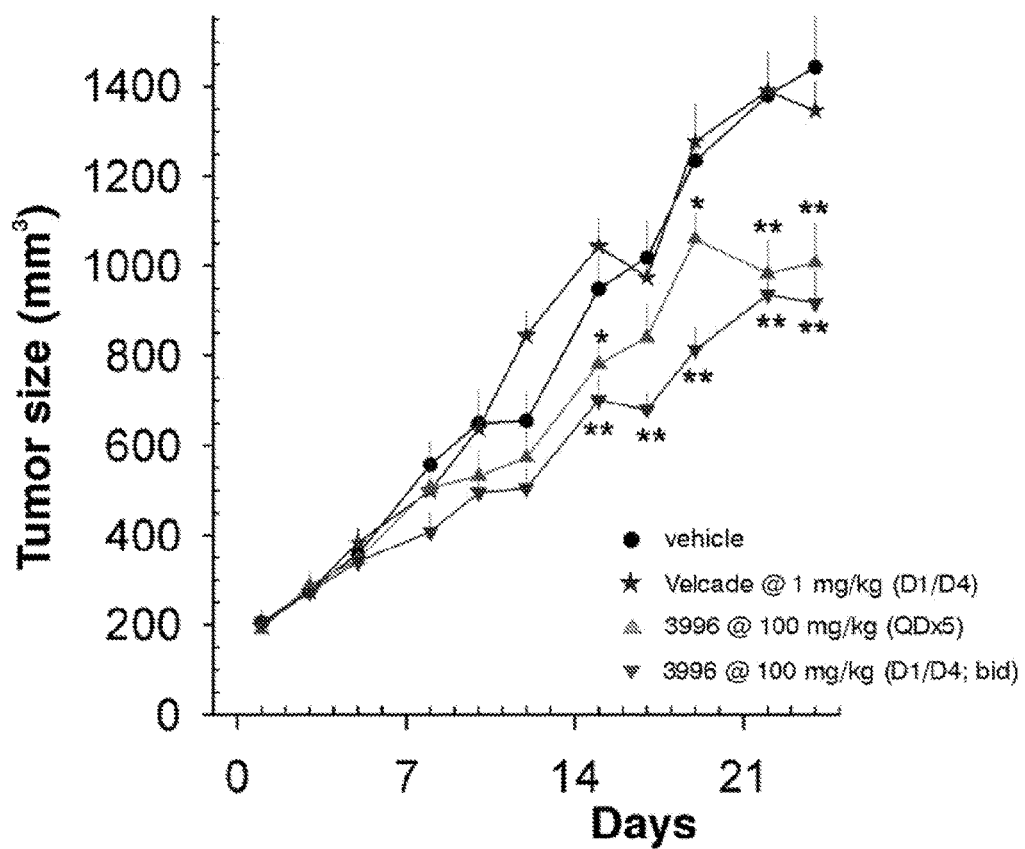
FIG. 6 shows a comparison of antitumor activities of ARI-3996 and bortezomib (Velcade®) at respective MTDs in SCID mice bearing established (~200 mm$^3$) HPAF-II carcinoma xenografts. ARI-3996 and bortezomib were administered twice weekly (day (D)1/D4 schedule), and ARI-3996 was also given from day 1 to day 5 for 5 consecutive days (QD×5 schedule). Asterisks indicate significant (p<0.05) reductions in tumor size in mice treated with ARI-3996, compared to controls.
Figure 9:
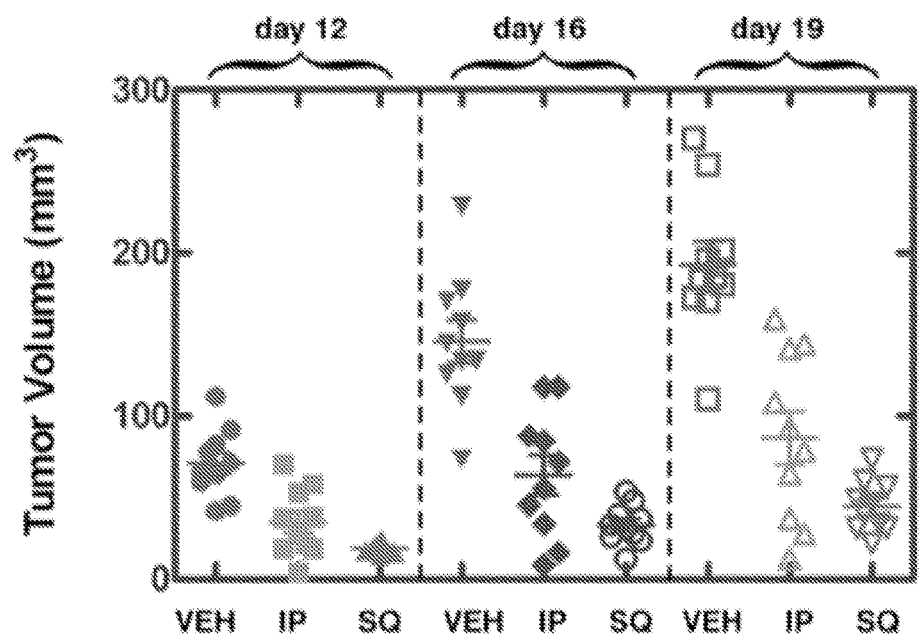
FIG. 9 shows the antitumor effect of ARI-3996 administered by i.p. (IP) and s.c. (SQ) routes at 50 mg/kg twice daily (b.i.d) on days 1 and 4 to SCID mice bearing HPAF-II xenografts. One-way ANOVA with Dunnett's post test for test versus vehicle (P<0.0001).
Figure 10:
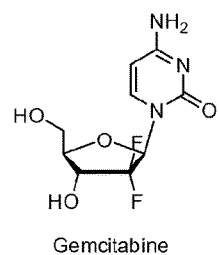
FIG. 10 shows antitumor activity of 50 mg/kg ARI-3996 with or without 6 mg/kg gemcitabine. ARI-3996 b.i.d. s.c. and gemcitabine once per day i.p. were administered twice weekly. Mean±SEM. The two compounds exhibit a strong synergistic effect when administered together.
Figure 10:
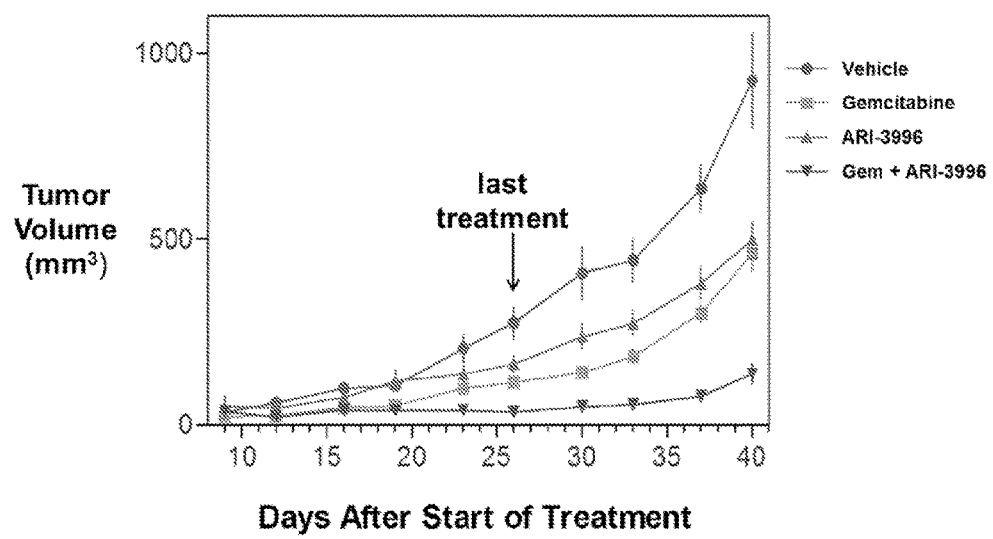

Example 5. Maximum Tolerated Doses (MTD) and Minimum Effective Doses (MED) of ARI-3996, ARI-2727D, and Bortezomib in the FAP$^+$ Cancer Model ARI-3996 administered (i.p.) to mice xenografted with the HPAF-II cell line significantly reduced tumor growth at its MTD of 100 mg/kg (FIG. 6). The antitumor effect of ARI-3996 was confirmed both as a single agent and in combination with gemcitabine (FIGS. 9 & 10). In particular, highly significant antitumor effect was observed when ARI-3996 was administered s.c. instead of i.p. (FIG. 9). In contrast, HPAF-II tumors were refractory to bortezomib at its MTD of 1 mg/kg (FIG. 6). ARI-3996, therefore, appears to be 100-fold safer than bortezomib based on MTD and to outperform bortezomib in a model of epithelial cancer. However, the antitumor effect of ARI-3996 was likely limited by the relatively low level of FAP activity, which is required to activate the prodrug, in HPAF-II tumors. As described above, the FAP tumor:plasma ration is ≥100:1 for human pancreatic cancer versus 3:1 in HPAF-II xenografted mice (FIG. 4). Therefore, in order to better judge ARI-3996's potential for producing antitumor effects in carcinoma patients at tolerated dose levels, MTDs and MEDs of ARI-3996, bortezomib and ARI-2727D will be compared in the mouse model selected for tumor-associated FAP activity equivalent to that in human cancer.

MTDs will be determined by administering (i.p.) escalating doses of compounds twice weekly (days 1 and 4) to groups of normal and tumor-bearing mice (n=2 female+2 male). Comparison of toxicity in tumor-bearing versus non-tumor-bearing mice will determine whether activation of ARI-3996 by tumor FAP contributes to systemic toxicity. Health of mice will be monitored daily, and mice will be weighed twice weekly. At sublethal dose levels, the highest dose that causes no ill health and no greater than 10% weight loss will be defined as the MTD. MEDs will be determined from dose responses of antitumor effects in tumor-bearing mice (n=5-7 per treatment group) administered compounds twice weekly. The MED will be defined as the smallest dose that produces a significant reduction in tumor growth as determined by unpaired, two-tailed Student's t test for comparison of tumor sizes between test and control mice. Experimental details will depend on the model chosen in Experiment 1. Study design will be similar to that previously described for the demonstration of the antitumor effect of the FAP-targeting antitumor agent, Glu-boroPro. TIs for ARI-3996, bortezomib and the 'warhead', ARI-2727D, will be calculated by the formula: TI=MTD÷MED. If the availability of LSL-K-ras$^{G12D}$ or Oncotest mice is limiting, toxicity and MTD can be investigated in FAP-HEK293 xenografted scid mice (FIG. 5).

Example 6. Characterization of the Mechanism of the Antitumor Effect of ARI-3996 by Investigating Inhibition of the 20S Proteasome, Induction of Apoptosis, and Reduction of Angiogenesis in FAP$^+$ Tumors One hour after final drug administration at termination of Example 5, peripheral blood, tumor, spleen and liver will be collected. Tissue lysates will be prepared from snap-frozen samples for assay of proteasome inhibition. Histological tissue specimens will be fixed in formalin and embedded in paraffin under conditions suited to immunostaining and apoptosis assay and sectioned.

Chymotryptic subunit activity of the 20S proteasome will be determined using the fluorogenic substrate succ-Leu-Leu-Val-Tyr-AMC (Enzo Life Science). Bortezomib and ARI-2727D will distribute to all tissues and are expected to inhibit proteasome activity in all tissues, uniformly, in a dose-dependent manner. The assay will test whether ARI-3996 targets tumor proteasome activity more selectively using a paired, two-tailed Student's t test for comparisons between paired samples of tumor and non-tumor tissue (e.g., spleen) in each animal. Histological sections of tumors that responded optimally to drug treatments will be compared to controls for microvessel density (MVD) by immunostaining with mouse CD34-specific antibody (BD-Pharmingen). Apoptosis will be quantified by terminal deoxynucleotidyl transferase-mediated nick end labeling (TUNEL) using the ApopTag peroxidase in situ apoptosis detection kit (Millipore). Events will be counted microscopically in a blinded manner, and significance of differences between vehicle- and drug-treated tumors will be determined by unpaired, two-tailed Student's t test for at least 5 mice per treatment group. Tissues will also be stained with H&E for investigation of systemic toxicity.

Figure 21:
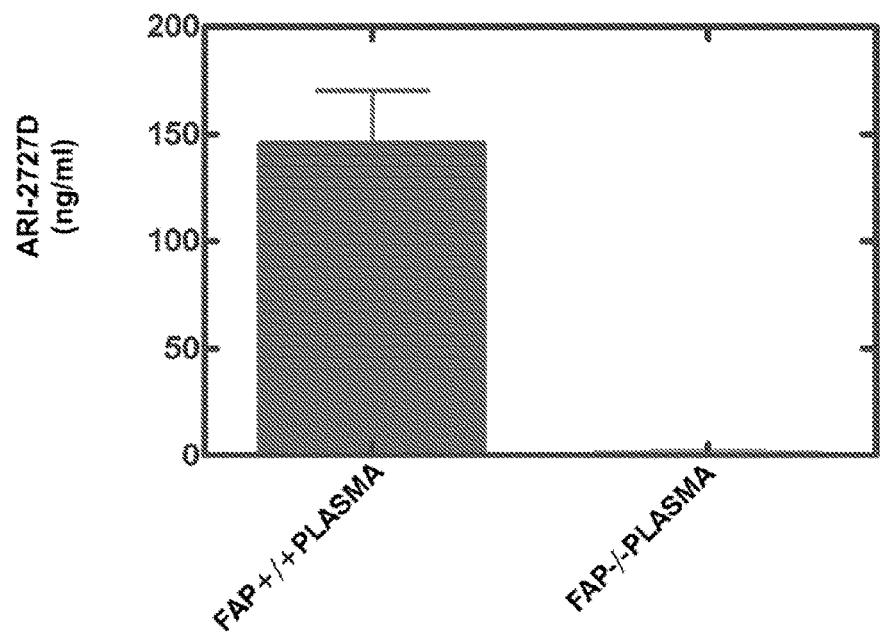
FIG. 21 shows that FAP knockout mouse blood plasma does not activate ARI-3996 to release ARI-2727.

We have found that FAP proteolytic activity of blood plasma appears to be approximately 6-fold higher in mice (~60 ΔFU/min) than in humans (~10 ΔFU/min) regardless of tumor status. Mouse models may over-report systemic toxicity of ARI-3996 compared with that possible in cancer patients. This was further verified by treatment of FAP knockout mice with ARI-3996. In knockout mice (FIG. 21), no activation of ARI-3996 to release ARI-2727 took place, whereas in FAP+ mice a concentration of the released warhead ARI-2727 of 150 ng/mL was reached.

Greater pro-drug activation in the peripheral blood of mice could result in greater systemic exposure to the ARI-2727D "warhead" than in humans. If mouse toxicity prevents achievement of the targeted 10-fold greater TI for ARI-3996 versus bortezomib, we will investigate toxicity in mice that are genetically deficient in FAP (Fap$^{LacZ/LacZ}$) (70). We have demonstrated that FAP-deficient mice have no significant proteolytic activity detectable with the FAP-specific substrate ARI-3144 (FIG. 1). Therefore, comparison of the MTD of ARI-3996 in FAP-sufficient versus FAP-deficient mice will determine how plasma FAP activity affects toxicity. If we find that ARI-3996 has highly significant preclinical antitumor activity, but the TI is compromised due to the basal level of plasma FAP activity in mice, we would consider the Test of Feasibility to be met.

Example 7. Evidence for Tumor Delivery of ARI-2727D by the FAP Activated Prodrug ARI-3996

Figure 7:
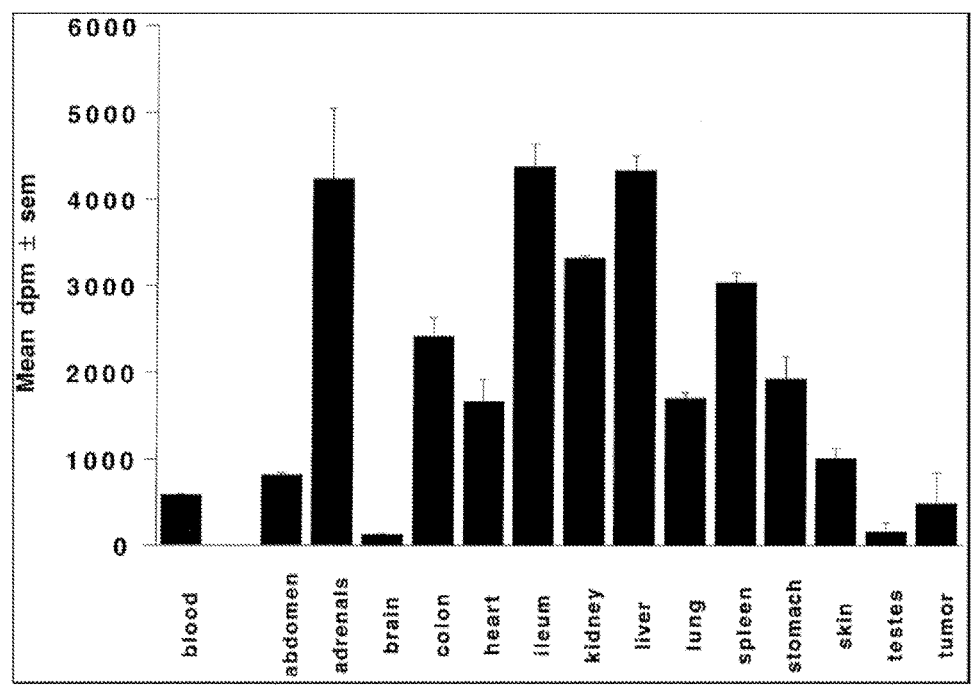
FIG. 7 shows the distribution of [$^{14}$C] bortezomib to tissues and tumor 1 hour after i.v. injection. The graph and data were taken from Adams et al (71). Data are mean dpm/100 mg tissue and mean dpm/100 μL blood.

Dose-limiting toxicity (DLT) prevents administration of high-enough doses of bortezomib to produce tumor responses in solid cancer. Preclinical results in mice xenografted s.c. with the human PC-3 prostate tumor suggest that DLT is due to the low exposure of solid tumors to bortezomib relative to the exposure of non-cancerous tissue (FIG. 7). ARI-3996 is a pro-drug designed to release a bortezomib-like PI, ARI-2727D, at the tumor site upon cleavage by proteolytic activity of fibroblast activation protein (FAP). Because FAP is predominantly expressed in stroma of human epithelial cancer, ARI-3996 should increase tumor exposure to the PI and reduce exposure in healthy tissues relative to bortezomib.

Figure 8:
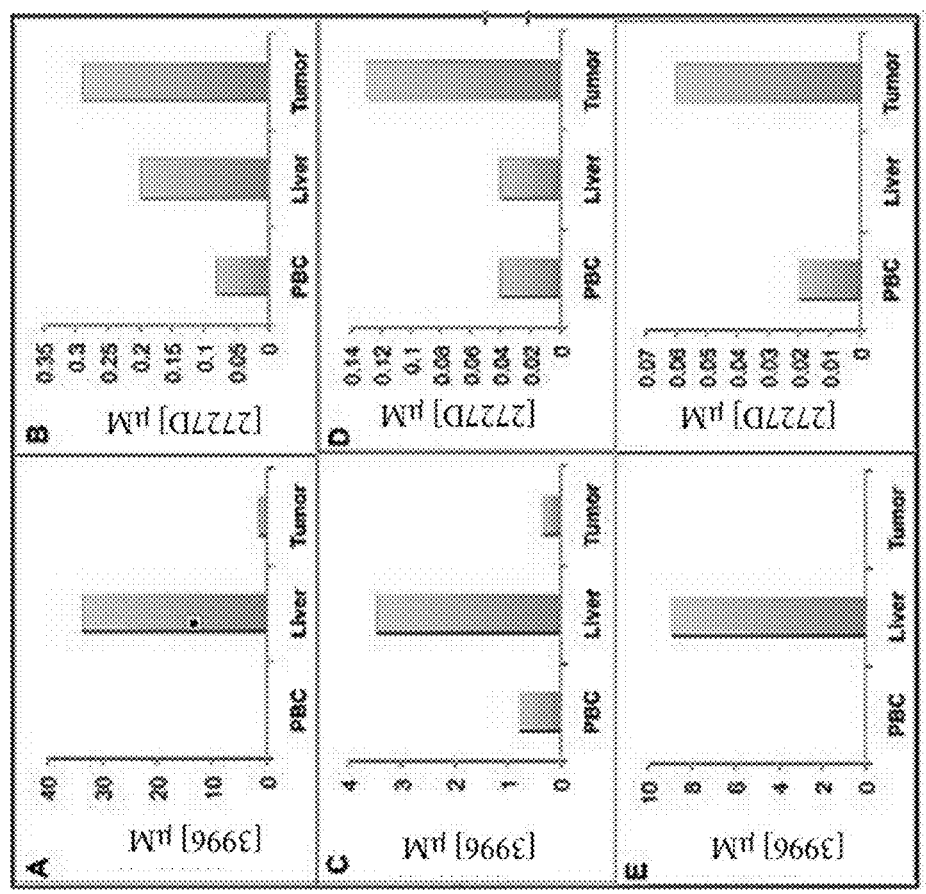
FIG. 8 shows tissue distribution of ARI-3996 and the warhead 2727D in SCID mice bearing HPAF-II s.c. tumors. Tumor-bearing mice were injected s.c. with 50 mg/kg ARI-3996. Tissues were harvested at 1 (A, B), 2 (C, D) and 3 hours (n=2) after administration of ARI-3996, and drug concentrations in tissue extracts were determined by LCMS.

In SCID mice xenografted with the human HPAF-II pancreatic adenocarcinoma, we have compared the tissue distribution of ARI-3996 and ARI-2727D in liver, peripheral blood cells (PBC) and tumor following a single s.c. injection of ARI-3996 at a dose of 50 mg/kg. At 1, 3 and 6 hours after administration, as for bortezomib (FIG. 7), liver exposure to intact ARI-3996 is greater than tumor exposure (FIG. 8 A, C, E), and exposure of PBC and tumor to pro-drug is similar at 3 hours. However, at all time points, tumor exposure to the active "warhead", ARI-3996 exceeded either liver or PBC exposures (FIG. 8 B, D, F).

Figure 22:
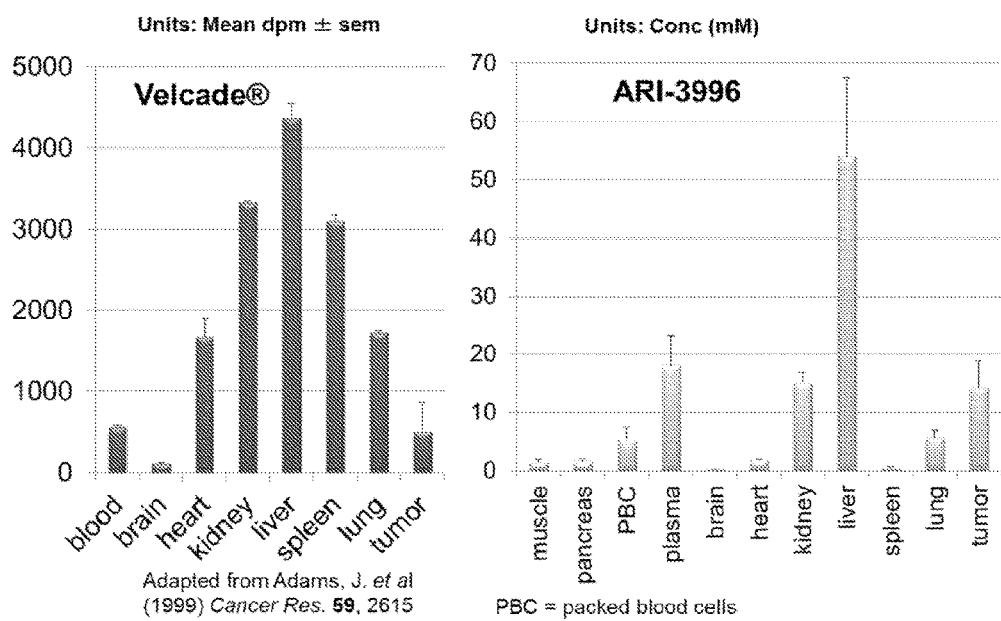
FIG. 22 shows tissue distribution of Velcade® versus ARI-3996 in mice.
Figure 23:
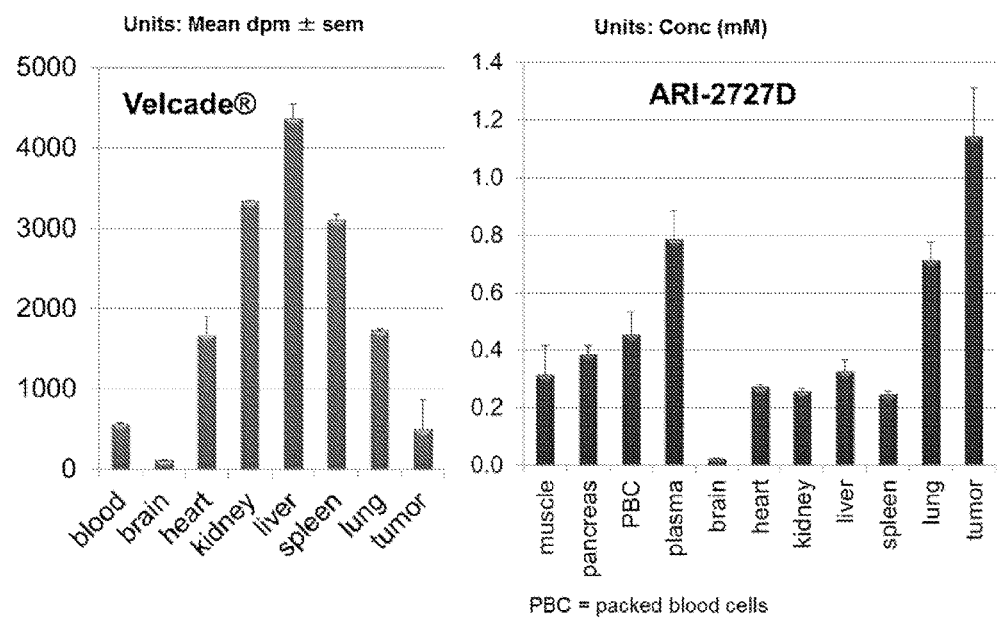
FIG. 23 shows tissue distribution of Velcade® versus ARI-2727D in mice. ARI-3996 is cleaved to ARI-2727D in and around tumors, thus facilitating the buildup of ARI-2727D in tumors.

Further evaluation (FIGS. 22 and 23) of the tissue distribution of Velcade® vs. ARI-3996 in mice showed that Velcade® reached much higher concentrations in the heart, lung, kidney, liver, spleen, and lung than in the tumor, suggesting that the drug's ineffectiveness against solid tumors results from its low concentration in the tumor. Velcade®'s high toxicity would also result from the accumulation of the drug in the organs at the expense of accumulation in the tumor. In contrast, ARI-3996 accumulates primarily in the liver initially; FAP activation/cleavage to form ARI-2727D results in ARI-2727D forming much higher relative concentrations in the tumor with lesser amounts in the lungs and plasma. Thus ARI-2727D is being selectively delivered to solid tumors via FAP activation of ARI-3996.

Figure 24:
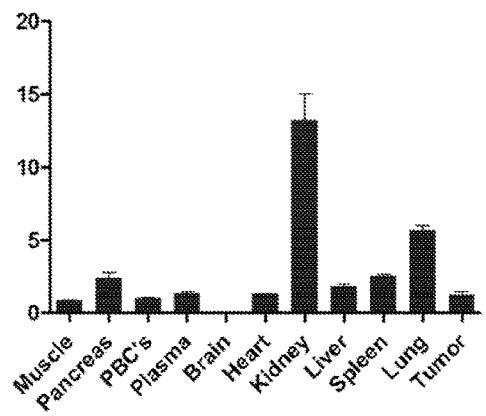
FIG. 24 shows the tissue distribution of ARI-2727D 1 hour after direct administration vs. administration as the prodrug form, ARI-3996 (top); and the average ratio at which ARI-2727D accumulates in the tumor versus the liver.
Figure 24:
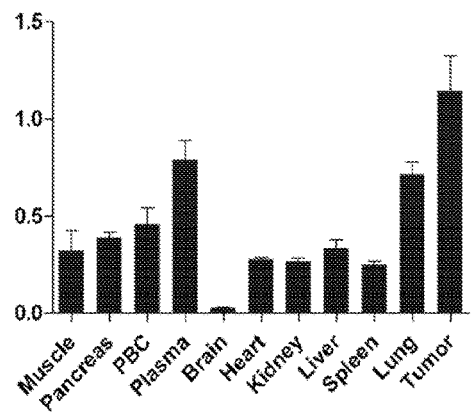

Finally, FAP activation was verified as the mode by which ARI-2727D tumor accumulation was taking place. In FIG. 24, ARI-2727D concentrations at 1 hour post-injection were compared with ARI-2727D concentrations 1 hour after injection of the prodrug form (ARI-3996). Direct injection of ARI-2727D resulted in the highest concentration of the drug accumulating in the kidneys and lung; when ARI-3996 was injected the highest concentration of ARI-2727D was found in the tumor, followed by lungs and plasma.

Remarkably, the results suggest that ARI-3996 increases tumor exposure to the active PI while sparing non-tumor tissue. Interestingly, in the HPAF-II tumor model, we have found that bortezomib lacks significant antitumor activity at the maximum tolerated dose of 1 mg/kg in mice (FIG. 6), whereas ARI-3996 is well tolerated and produces significant reductions in tumor size at 50 mg/kg (FIGS. 9 and 10). The HPAF-II tumor response to ARI-3996 strengthens our hypothesis that solid tumors can respond to proteasome inhibition. The tumor:plasma ratio of FAP activity is only 3:1 in HPAF-II mice, whereas in pancreatic cancer patients the ratio is 100:1 or greater. Therefore, we anticipate significantly greater activation of ARI-3996 and, consequently, further improvements in tumor responses in the mouse model with a higher tumor:plasma FAP will be identified in further studies.

Example 8. Cytotoxicity of Velcade® Versus ARI-2727D and ARI-3996 in Multiple Myeloma, Normal Cells, and Solid Tumors Although Velcade® has robust clinical activity in MM patients, drug resistance develops in all patients who initially respond to treatment. Stromal fibroblasts in epithelial tumors promote tumor progression and metastasis through the remodeling of the extracellular matrix and as a source of paracrine growth factors such as fibroblast growth factor, epidermal growth factor and transforming growth factor-β. By targeting proteasome inhibition to the tumor microenvironment, ARI-3996 may kill stromal fibroblasts as well as malignant epithelial cells. This would provide the opportunity to attack the tumor by killing a cell type that is less likely than the tumor cell itself to develop drug-resistance.

Figure 25:
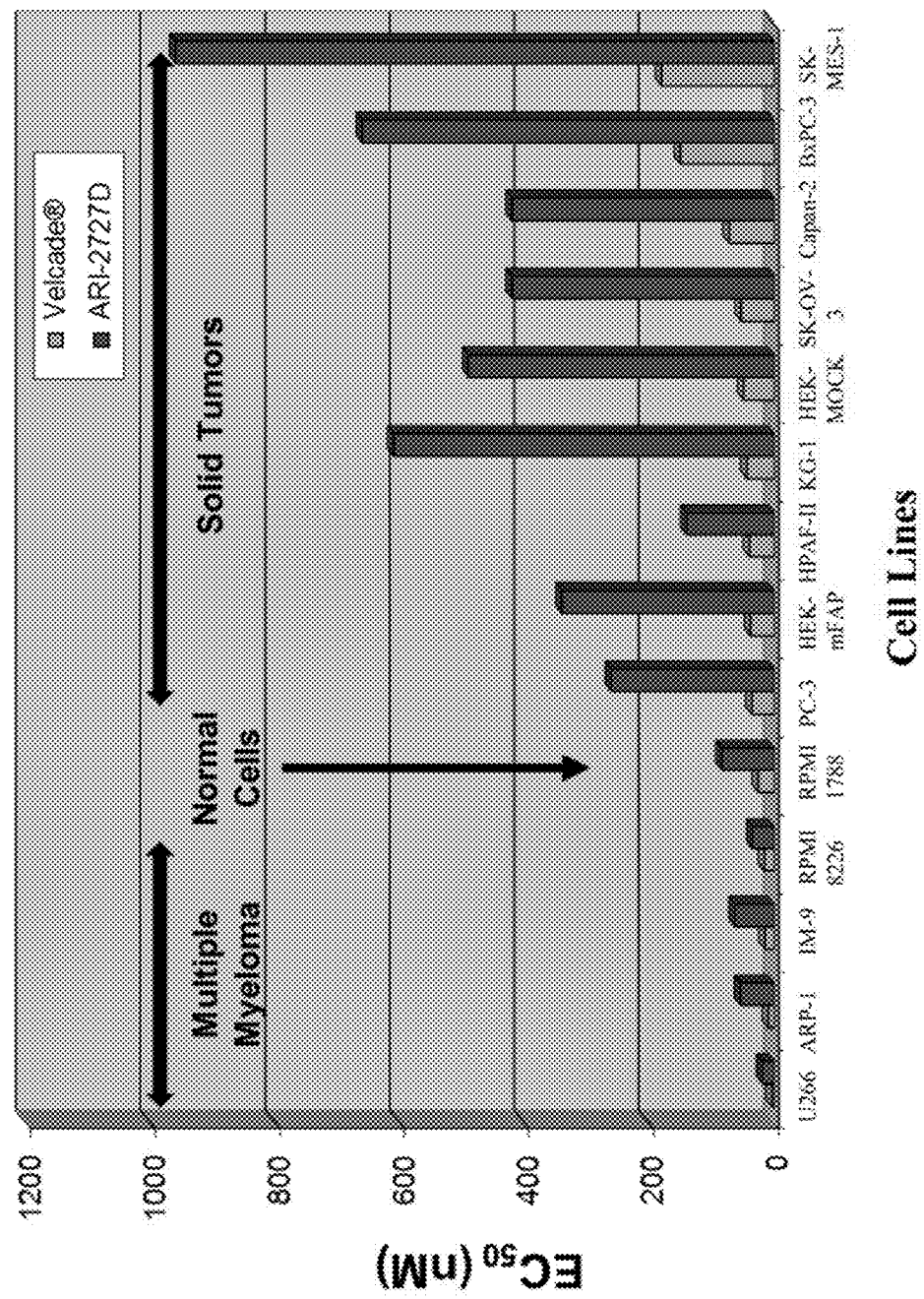
FIG. 25 shows the cytotoxicity of Velcade® versus ARI-2727D in multiple myeloma, normal cells, and solid tumors.
Figure 26:
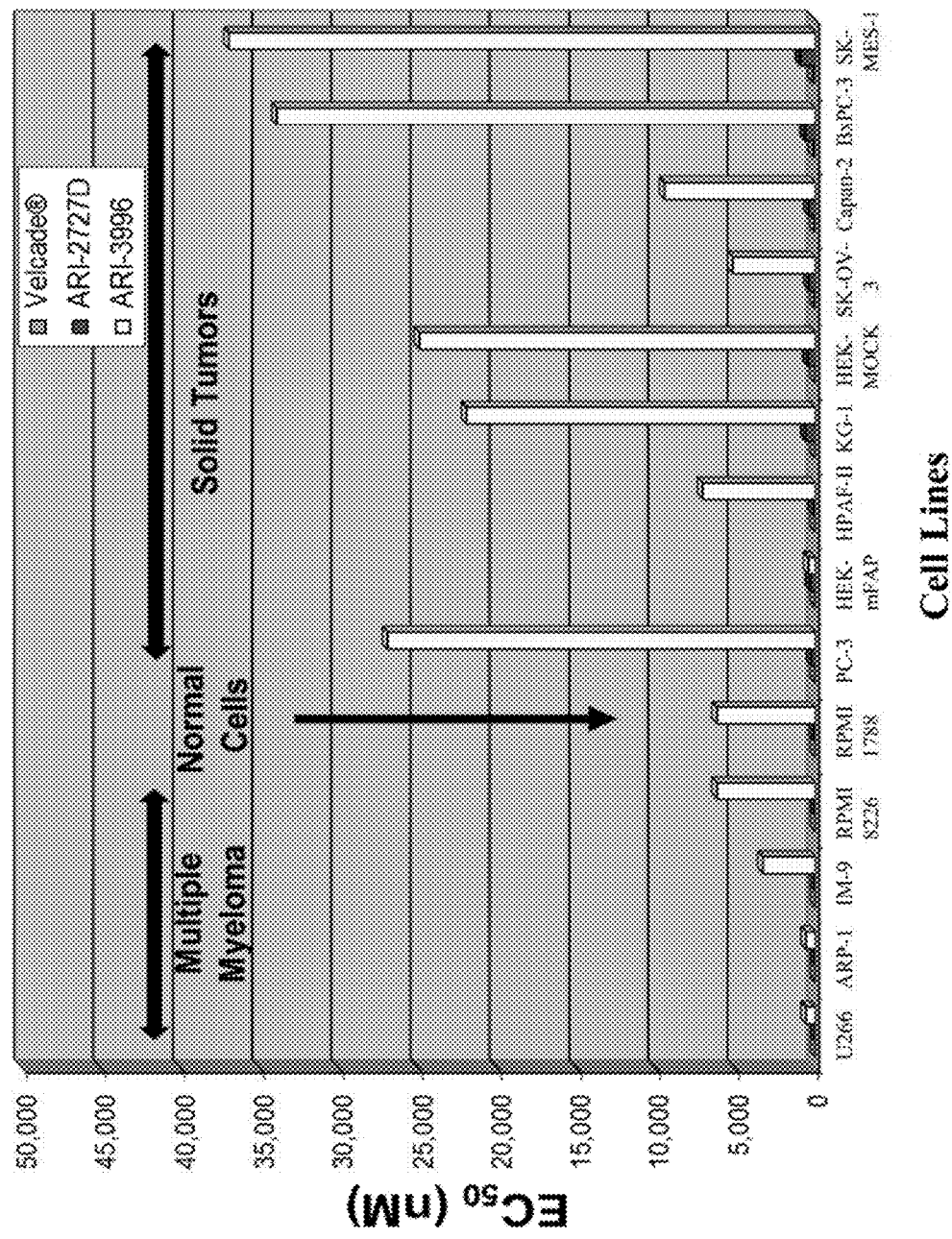
FIG. 26 shows the cytotoxicity of Velcade® versus ARI-2727D versus ARI-3996 in multiple myeloma, normal cells, and solid tumors.

FIGS. 25 and 26 demonstrate further biological evaluation of ARI-2727D and ARI-3996 vs. Velcade® for cytotoxicity toward Multiple Myeloma (MM), normal cells, and various solid tumors. FIG. 25 shows that both Velcade® and ARI-2727D have extremely high potency against various MM cell lines and slightly lower toxicity against normal cells. Their toxicity is much lower against solid tumors. In FIG. 26 ARI-3996 is compared with ARI-2727D and Velcade®. Its cytotoxicity is much lower across the board, particularly in solid tumors.

These results underscore the importance of selective delivery in solving the ongoing challenges in conventional cancer chemotherapy. Without selective delivery of cytotoxic agents to cancer cells, they often display equal toxicity to normal and cancerous cells alike.

Example 9. FAP Activity of Human Cancers

One important aspect of determining which cancers will benefit from treatment with the compounds of the invention. As mentioned above, FAP has very low expression in normal human tissues. A large number of tissue samples from tumors were collected and their FAP activity—not expression levels—measured. As FIG. 27 shows, virtually all the samples show a much higher level of FAP activity in the tumor vs. the serum. Thus, most solid tumors susceptible to proteasome inhibitors are expected to respond to treatment with FAP-activated prodrugs of the invention. As shown in FIG. 4, human tumors have, on average, 100:1 the FAP activity levels of normal human tissue.

Figure 28:
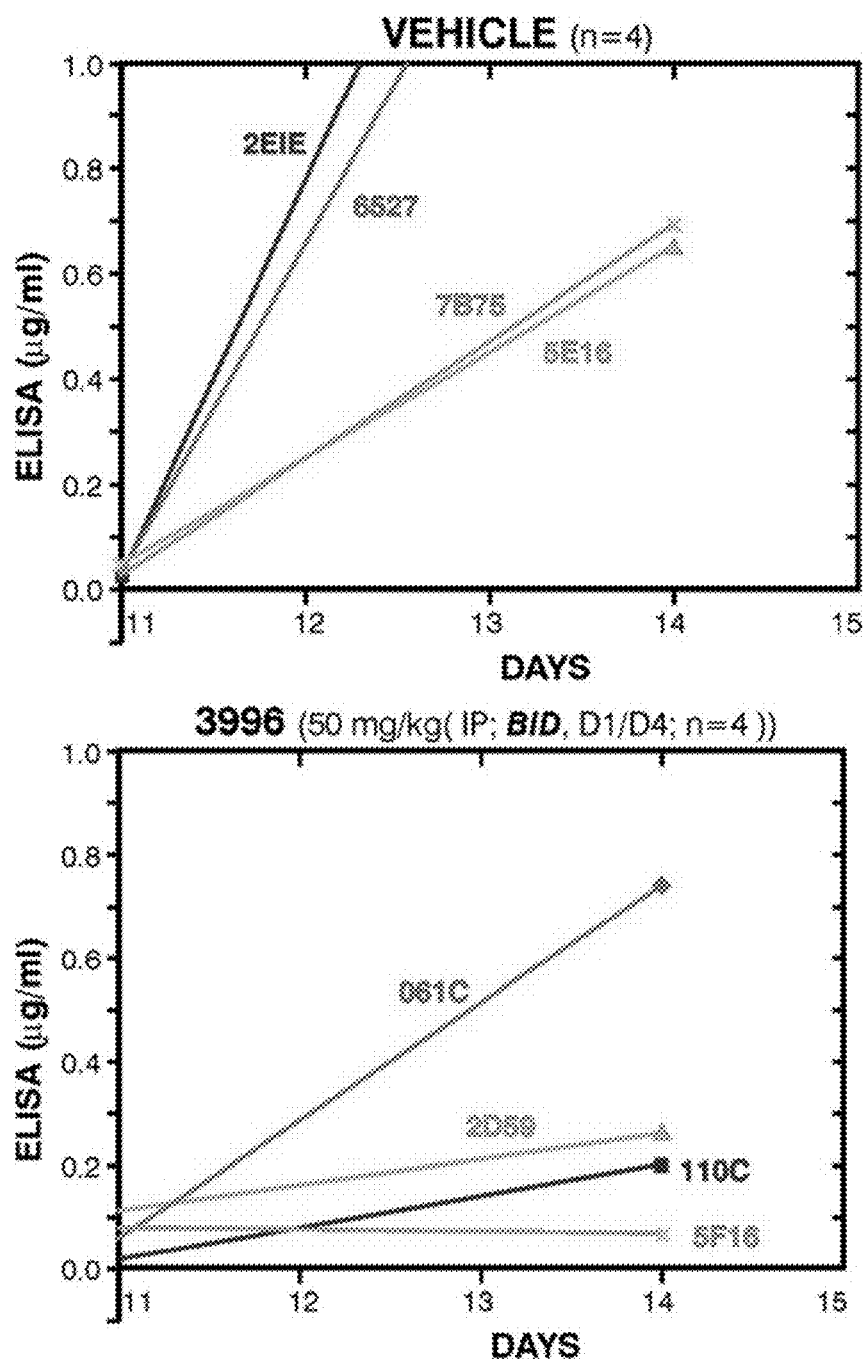
FIG. 28 shows the anticancer effects of proteasome inhibitors Velcade® and ARI-3996 in U266 tumor-bearing mice.
Figure 28:
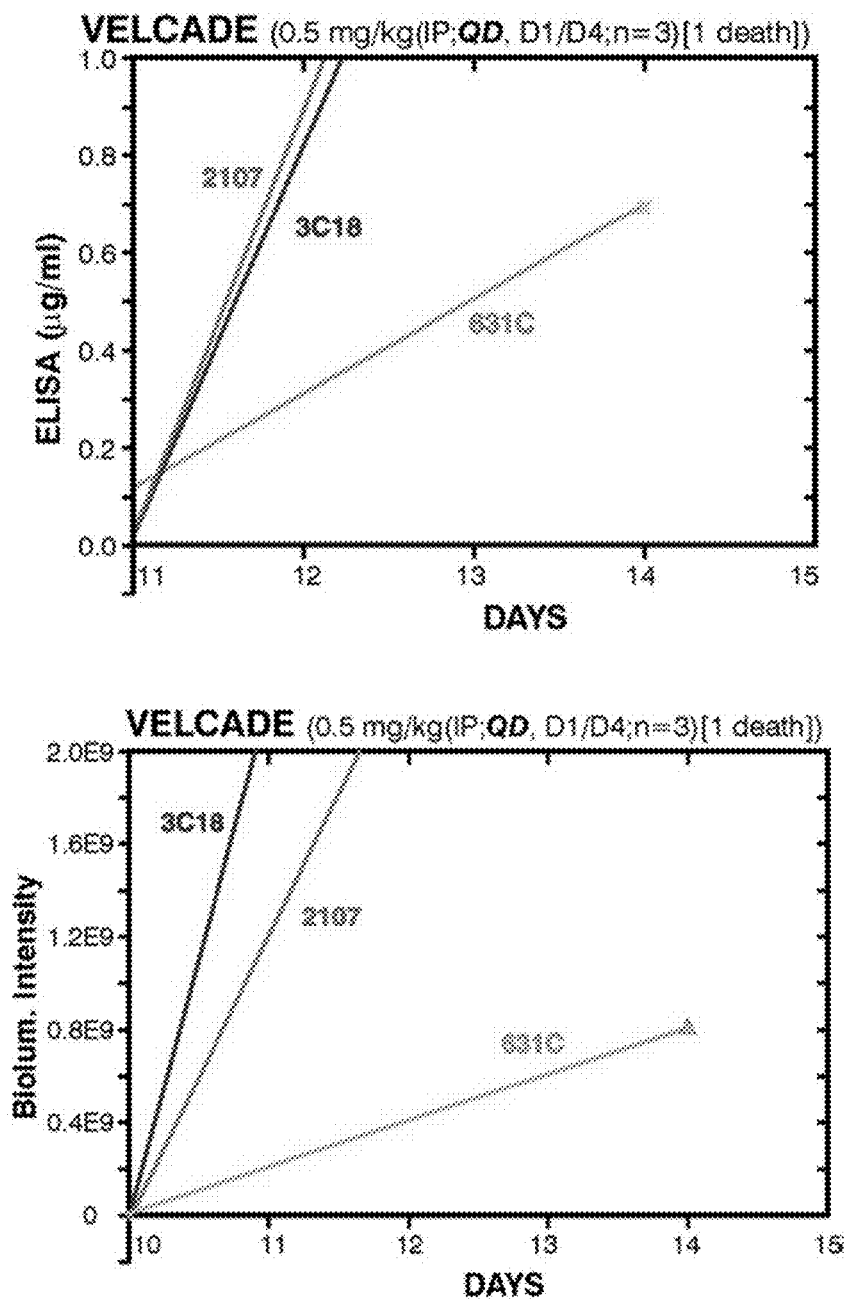
Figure 28:
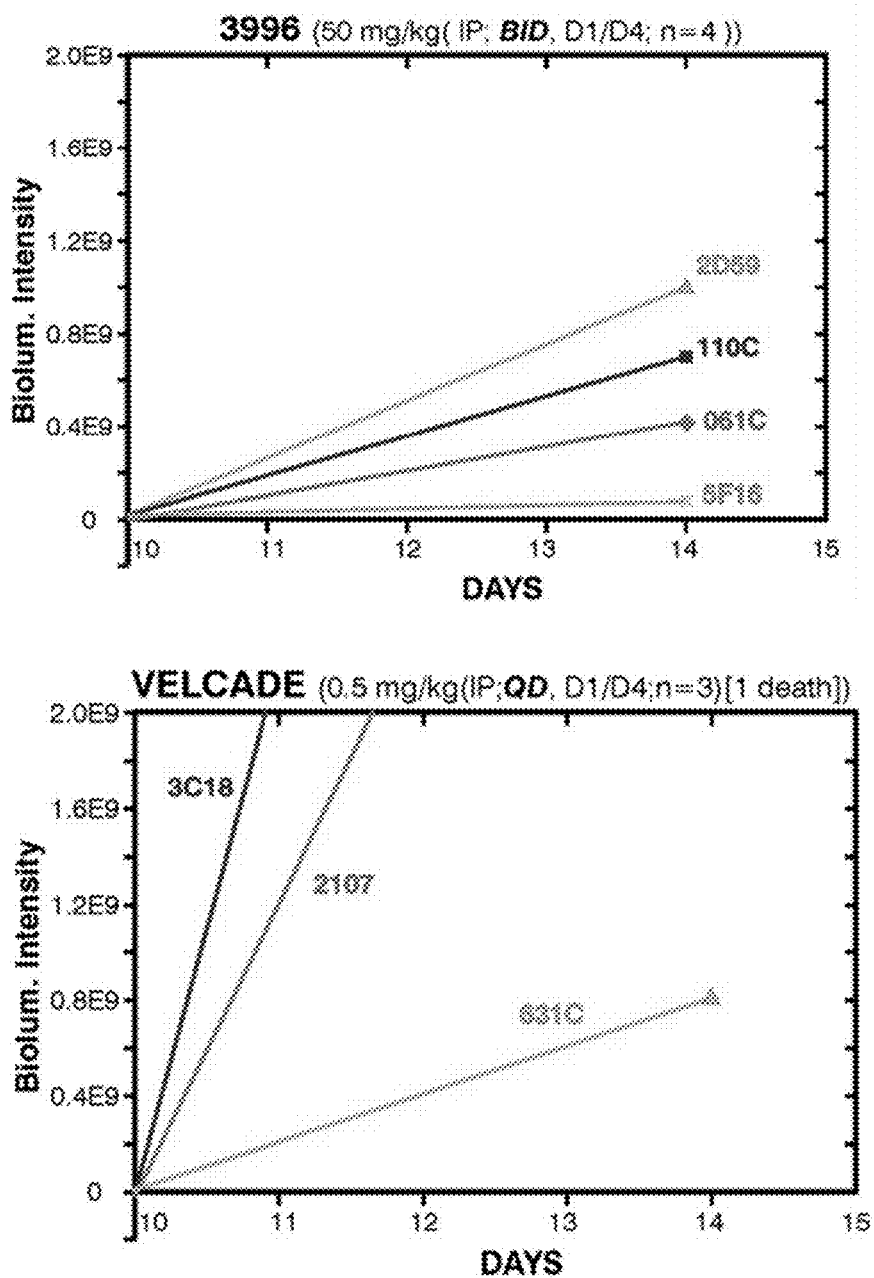

Example 10. Anticancer Effects of Proteasome Inhibitors in U266 Tumor-Bearing Mice ARI-3996 consistently outperformed Velcade® in a mouse MM model. Mice bearing U266 tumor xenografts (2 female, 2 male) were treated with either the vehicle, ARI-3996, or Velcade® twice a week (day 1 and day 4) for 2 weeks. As shown in FIG. 28, ARI-3996 was dosed at 50 mg/kg (½ the MTD) and Velcade® at 0.5 mg/kg (also ½ the MTD). The inhibition of the tumor was evaluated using ELISA (g/mL) and bioluminescence. ARI-3996 showed a marked advantage over Velcade®. While 1 death took place in the Velcade® group, all mice in the ARI-3996 group survived with improved outcomes vs. the Velcade® group.

Example 11. Conjugation of FAP Recognition Site to Known Proteasome Inhibitors

Since the above Examples demonstrate that the FAP recognition site (the short peptide chain conferring FAP specificity) when attached to ARI-2727D confers selective delivery of the warhead to tumors and the surrounding stromal cells, it is reasonable to conclude that the same FAP recognition sequence could be attached to other proteasome inhibitors to yield the same effect. Many short peptide and peptide analogue sequences are known to inhibit the proteasome. Attachment of these sequences to the FAP recognition site by the N-terminal amide of the inhibitor/warhead will form prodrug of similar potency, specificity, and (low) toxicity as ARI-3996.

Many of the most potent proteasome inhibitors contain 2-4 peptides or peptide analogues with an electrophilic moiety replacing or appended to the carboxyl terminus. This electrophilic moiety is a reactive species that covalently modifies a nucleophilic residue of the proteasome, destroying its catalytic activity. Such a method of inactivating an enzyme is commonly referred to as "suicide inhibition" in the literature. Examples of successfully validated electrophilic moieties include boronates, epoxyketones, aldehydes, cyanates, vinyl sulfones, α,β-unsaturated carbonyls, and ketoaldehydes.

Figure 29:
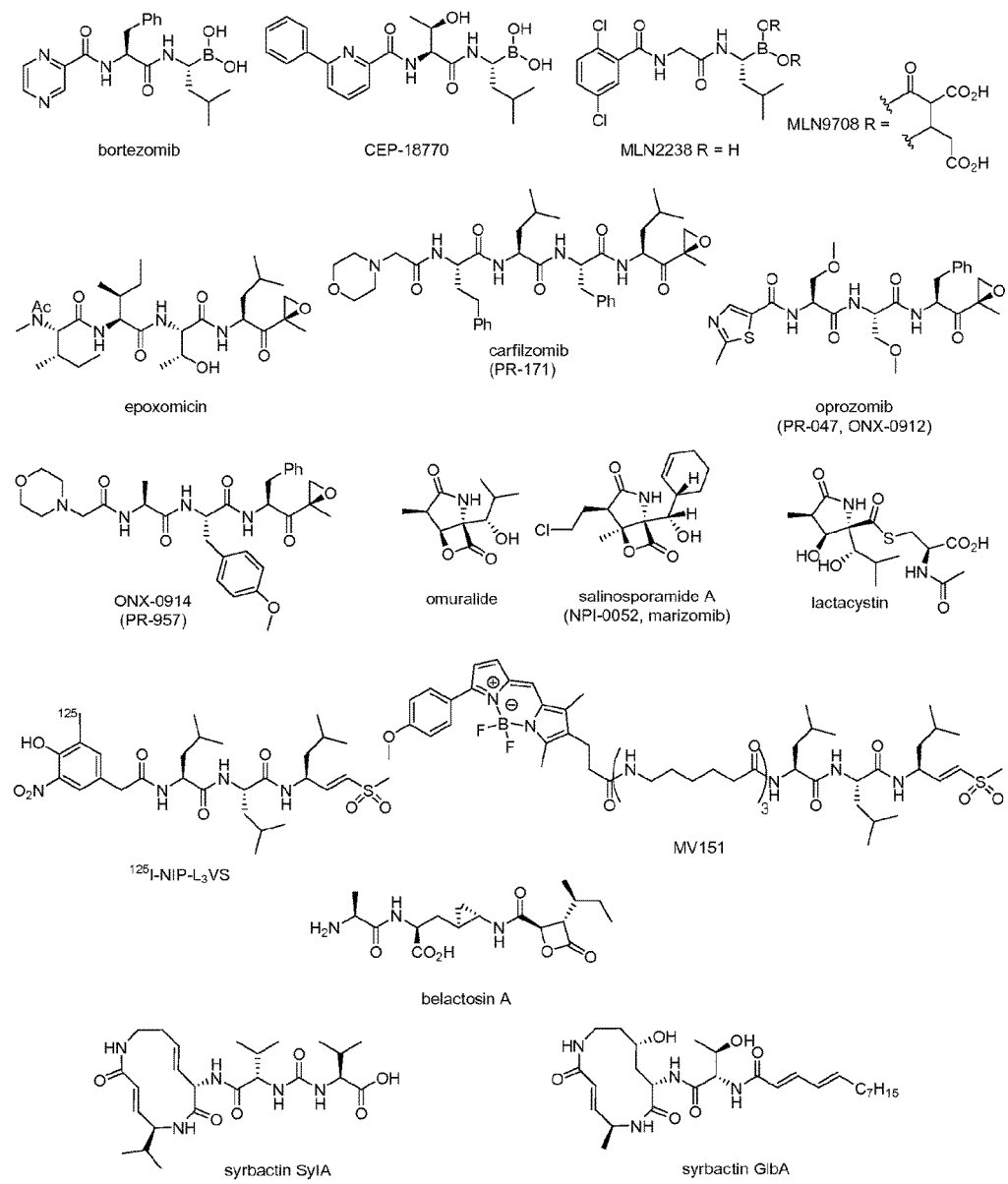
FIG. 29 shows the chemical structures and names of a number of known proteasome inhibitors.
Figure 29:
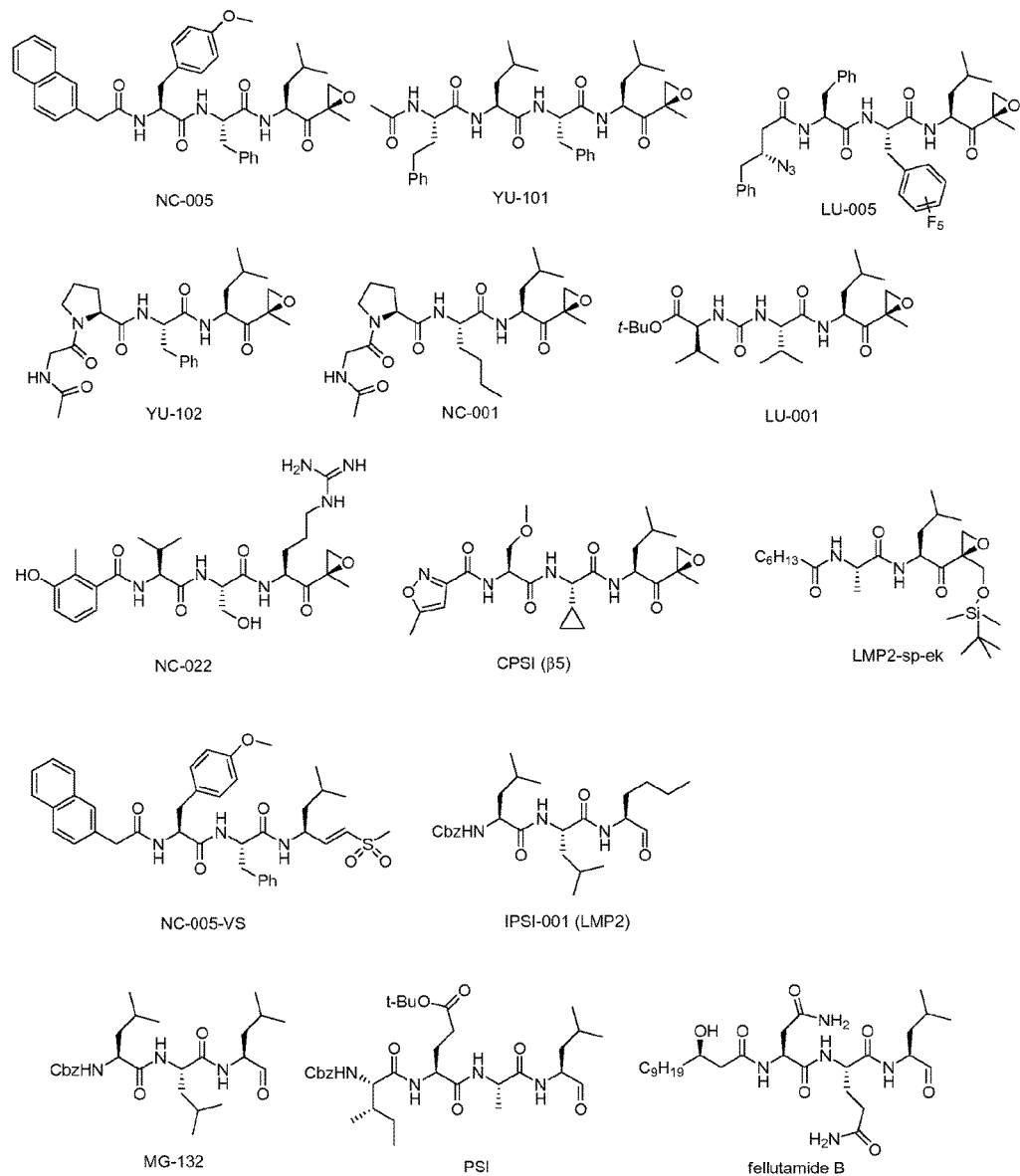

The structures of a number of clinically relevant or otherwise validated proteasome inhibitors are shown in FIG. 29. Careful consideration of the chemical structures reveals certain similarities. Most are di-, tri-, or tetrapeptides with an electrophilic moiety attached to the carboxyl terminus. At the amino terminus is generally an acyl or aracyl group (bortezomib, CEP-18770, MLN2238, MLN9708, MG-132, PSI, $^{125}$I-NIP-L$_3$VS, carfilzomib, oprozomib, epoximicin, PR-957, NC-005, NC-005-VS, YU-101, LU-005, YU-102, NC-001, NC-022, CPSI, and IPSI-001). These acyl or aracyl groups are present to increase the resistance of the proteasome inhibitor against nonspecific proteases that might otherwise degrade short peptides.

If these N-terminal acyl or aracyl groups attached to the various proteasome inhibitors shown in FIG. 29 are removed and replaced with the FAP recognition site described herein, the result would be novel FAP-activated proteasome inhibitors whose specificity and toxicity would be greatly improved over their parent molecules.

REFERENCES CITED

1. Dolznig, H., N. Schweifer, C. Puri, N. Kraut, W. J. Rettig, D. Kerjaschki, and P. Garin-Chesa. 2005. Characterization of cancer stroma markers: in silico analysis of an mRNA expression database for fibroblast activation protein and endosialin. *Cancer Immun* 5:10.
2. Lee, K. N., K. W. Jackson, V. J. Christiansen, C. S. Lee, J. G. Chun, and P. A. McKee. 2006. Antiplasmin-cleaving enzyme is a soluble form of fibroblast activation protein. *Blood* 107:1397-1404.
3. Orlowski, R. Z., and D. J. Kuhn. 2008. Proteasome inhibitors in cancer therapy: lessons from the first decade. *Clin Cancer Res* 14:1649-1657.
4. Orlowski, R. Z., and A. S. Baldwin, Jr. 2002. NF-kappaB as a therapeutic target in cancer. *Trends Mol Med* 8:385-389.
5. Hideshima, T., P. Richardson, D. Chauhan, V. J. Palombella, P. J. Elliott, J. Adams, and K. C. Anderson. 2001. The proteasome inhibitor PS-341 inhibits growth, induces apoptosis, and overcomes drug resistance in human multiple myeloma cells. *Cancer Res* 61:3071-3076.
6. LeBlanc, R., L. P. Catley, T. Hideshima, S. Lentzsch, C. S. Mitsiades, N. Mitsiades, D. Neuberg, O. Goloubeva, C. S. Pien, J. Adams, D. Gupta, P. G. Richardson, N. C. Munshi, and K. C. Anderson. 2002. Proteasome inhibitor PS-341 inhibits human myeloma cell growth in vivo and prolongs survival in a murine model. *Cancer Res* 62:4996-5000.
7. Orlowski, R. Z., J. R. Eswara, A. Lafond-Walker, M. R. Grever, M. Orlowski, and C. V. Dang. 1998. Tumor growth inhibition induced in a murine model of human Burkitt's lymphoma by a proteasome inhibitor. *Cancer Res* 58:4342-4348.
8. Richardson, P. G., T. Hideshima, and K. C. Anderson. 2003. Bortezomib (PS-341): a novel, first-in-class proteasome inhibitor for the treatment of multiple myeloma and other cancers. *Cancer Control* 10:361-369.
9. Bross, P. F., R. Kane, A. T. Farrell, S. Abraham, K. Benson, M. E. Brower, S. Bradley, J. V. Gobburu, A. Goheer, S.-L. Lee, J. Leighton, C. Y. Liang, R. T. Lostritto, W. D. McGuinn, D. E. Morse, A. Rahman, L. A. Rosario, S. L. Verbois, G. Williams, Y.-C. Wang, and R. Pazdur. 2004. Approval summary for bortezomib for injection in the treatment of multiple myeloma. *Clin Cancer Res* 10:3954-3964.
10. Chauhan, D., H. Uchiyama, Y. Akbarali, M. Urashima, K. Yamamoto, T. A. Libermann, and K. C. Anderson. 1996. Multiple myeloma cell adhesion-induced interleukin-6 expression in bone marrow stromal cells involves activation of NF-kappa B. *Blood* 87:1104-1112.
11. Obeng, E. A., L. M. Carlson, D. M. Gutman, W. J. Harrington, Jr., K. P. Lee, and L. H. Boise. 2006. Proteasome inhibitors induce a terminal unfolded protein response in multiple myeloma cells. *Blood* 107:4907-4916.
12. McConkey, D. J., and K. Zhu. 2008. Mechanisms of proteasome inhibitor action and resistance in cancer. *Drug Resist Updat* 11:164-179.
13. Engel, R. H., J. A. Brown, J. H. Von Roenn, R. M. O'Regan, R. Bergan, S. Badve, A. Rademaker, and W. J. Gradishar. 2007. A phase II study of single agent bortezomib in patients with metastatic breast cancer: a single institution experience. *Cancer Invest* 25:733-737.
14. Dees, E. C., and R. Z. Orlowski. 2006. Targeting the ubiquitin-proteasome pathway in breast cancer therapy. *Future Oncol* 2:121-135.
15. Hamilton, A. L., J. P. Eder, A. C. Pavlick, J. W. Clark, L. Liebes, R. Garcia-Carbonero, A. Chachoua, D. P. Ryan, V. Soma, K. Farrell, N. Kinchla, J. Boyden, H. Yee, A. Zeleniuch-Jacquotte, J. Wright, P. Elliott, J. Adams, and F. M. Muggia. 2005. Proteasome inhibition with bortezomib (PS-341): a phase I study with pharmacodynamic end points using a day 1 and day 4 schedule in a 14-day cycle. *J Clin Oncol* 23:6107-6116.
16. Aghajanian, C., J. A. Blessing, K. M. Darcy, G. Reid, K. DeGeest, S. C. Rubin, R. S. Mannel, J. Rotmensch, R. J. Schilder, and W. Riordan. 2009. A phase II evaluation of bortezomib in the treatment of recurrent platinum-sensitive ovarian or primary peritoneal cancer: a Gynecologic Oncology Group study. *Gynecol Oncol* 115:215-220.
17. Lonial, S., E. K. Waller, P. G. Richardson, S. Jagannath, R. Z. Orlowski, C. R. Giver, D. L. Jaye, D. Francis, S. Giusti, C. Torre, B. Barlogie, J. R. Berenson, S. Singhal, D. P. Schenkein, D. L. Esseltine, J. Anderson, H. Xiao, L. T. Heffner, and K. C. Anderson. 2005. Risk factors and kinetics of thrombocytopenia associated with bortezomib for relapsed, refractory multiple myeloma. *Blood* 106:3777-3784.
18. Richardson, P. G., H. Briemberg, S. Jagannath, P. Y. Wen, B. Barlogie, J. Berenson, S. Singhal, D. S. Siegel, D. Irwin, M. Schuster, G. Srkalovic, R. Alexanian, S. V. Rajkumar, S. Limentani, M. Alsina, R. Z. Orlowski, K. Najarian, D. Esseltine, K. C. Anderson, and A. A. Amato. 2006. Frequency, characteristics, and reversibility of peripheral neuropathy during treatment of advanced multiple myeloma with bortezomib. *J Clin Oncol* 24:3113-3120.
19. Groll, M., R. Huber, and L. Moroder. 2009. The persisting challenge of selective and specific proteasome inhibition. *J Pept Sci* 15:58-66.
20. Park, J. E., M. C. Lenter, R. N. Zimmermann, P. Garin-Chesa, L. J. Old, and W. J. Rettig. 1999. Fibroblast activation protein, a dual specificity serine protease expressed in reactive human tumor stromal fibroblasts. *J Biol Chem* 274:36505-36512.
21. Scanlan, M. J., B. K. Raj, B. Calvo, P. Garin-Chesa, M. P. Sanz-Moncasi, J. H. Healey, L. J. Old, and W. J. Rettig. 1994. Molecular cloning of fibroblast activation protein alpha, a member of the serine protease family selectively expressed in stromal fibroblasts of epithelial cancers. *Proc Natl Acad Sci USA* 91:5657-5661.
22. Jemal, A., R. Siegel, E. Ward, Y. Hao, J. Xu, and M. J. Thun. 2009. Cancer statistics, 2009. *CA Cancer J Clin* 59:225-249.
23. Stinchcombe, T. E., and M. A. Socinski. 2009. Current treatments for advanced stage non-small cell lung cancer. *Proc Am Thorac Soc* 6:233-241.
24. Pennell, N. A., and T. Mekhail. 2009. Investigational agents in the management of non-small cell lung cancer. *Curr Oncol Rep* 11:275-284.
25. Di Costanzo, F., F. Mazzoni, M. Micol Mela, L. Antonuzzo, D. Checcacci, and M. Saggese. 2008. Bevacizumab in non-small cell lung cancer. *Drugs* 68:737-746.
26. Baselga, J., D. Tripathy, J. Mendelsohn, S. Baughman, C. C. Benz, L. Dantis, N. T. Sklarin, A. D. Seidman, C. A. Hudis, J. Moore, P. P. Rosen, T. Twaddell, I. C. Henderson, and L. Norton. 1996. Phase II study of weekly intravenous recombinant humanized anti-p185HER2

27. Cobleigh, M. A., C. L. Vogel, D. Tripathy, N. J. Robert, S. Scholl, L. Fehrenbacher, J. M. Wolter, V. Paton, S. Shak, G. Lieberman, and D. J. Slamon. 1999. Multinational study of the efficacy and safety of humanized anti-HER2 monoclonal antibody in women who have HER2-overexpressing metastatic breast cancer that has progressed after chemotherapy for metastatic disease. *J Clin Oncol* 17:2639-2648.

28. Vogel, C. L., M. A. Cobleigh, D. Tripathy, J. C. Gutheil, L. N. Harris, L. Fehrenbacher, D. J. Slamon, M. Murphy, W. F. Novotny, M. Burchmore, S. Shak, S. J. Stewart, and M. Press. 2002. Efficacy and safety of trastuzumab as a single agent in first-line treatment of HER2-overexpressing metastatic breast cancer. *J Clin Oncol* 20:719-726.

29. Nahta, R., and F. J. Esteva. 2006. HER2 therapy: molecular mechanisms of trastuzumab resistance. *Breast Cancer Res* 8:215.

30. Richardson, P. G., C. Mitsiades, T. Hideshima, and K. C. Anderson. 2006. Bortezomib: proteasome inhibition as an effective anticancer therapy. *Annu Rev Med* 57:33-47.

31. Milano, A., R. V. Iaffaioli, and F. Caponigro. 2007. The proteasome: a worthwhile target for the treatment of solid tumours? *Eur J Cancer* 43:1125-1133.

32. Caravita, T., P. de Fabritiis, A. Palumbo, S. Amadori, and M. Boccadoro. 2006. Bortezomib: efficacy comparisons in solid tumors and hematologic malignancies. *Nat Clin Pract Oncol* 3:374-387.

33. Gilardini, A., P. Marmiroli, and G. Cavaletti. 2008. Proteasome inhibition: a promising strategy for treating cancer, but what about neurotoxicity? *Curr Med Chem* 15:3025-3035.

34. Sterz, J., I. von Metzler, J. C. Hahne, B. Lamottke, J. Rademacher, U. Heider, E. Terpos, and O. Sezer. 2008. The potential of proteasome inhibitors in cancer therapy. *Expert Opin Investig Drugs* 17:879-895.

35. Zavrski, I., L. Kleeberg, M. Kaiser, C. Fleissner, U. Heider, J. Sterz, C. Jakob, and O. Sezer. 2007. Proteasome as an emerging therapeutic target in cancer. *Curr Pharm Des* 13:471-485.

36. Spataro, V., C. Norbury, and A. L. Harris. 1998. The ubiquitin-proteasome pathway in cancer. *Br J Cancer* 77:448-455.

37. Windebank, A. J., and W. Grisold. 2008. Chemotherapy-induced neuropathy. *J Peripher Nerv Syst* 13:27-46.

38. Adams, J., V. J. Palombella, E. A. Sausville, J. Johnson, A. Destree, D. D. Lazarus, J. Maas, C. S. Pien, S. Prakash, and P. J. Elliott. 1999. Proteasome inhibitors: a novel class of potent and effective antitumor agents. *Cancer Res* 59:2615-2622.

39. Wang, C. Y., M. W. Mayo, and A. S. Baldwin, Jr. 1996. TNF- and cancer therapy-induced apoptosis: potentiation by inhibition of NF-kappaB. *Science* 274:784-787.

40. Wang, C. Y., J. C. Cusack, Jr., R. Liu, and A. S. Baldwin, Jr. 1999. Control of inducible chemoresistance: enhanced anti-tumor therapy through increased apoptosis by inhibition of NF-kappaB. *Nat Med* 5:412-417.

41. Cusack, J. C., Jr., R. Liu, M. Houston, K. Abendroth, P. J. Elliott, J. Adams, and A. S. Baldwin, Jr. 2001. Enhanced chemosensitivity to CPT-11 with proteasome inhibitor PS-341: implications for systemic nuclear factor-kappaB inhibition. *Cancer Res* 61:3535-3540.

42. Ling, Y. H., L. Liebes, B. Ng, M. Buckley, P. J. Elliott, J. Adams, J. D. Jiang, F. M. Muggia, and R. Perez-Soler. 2002. PS-341, a novel proteasome inhibitor, induces Bcl-2 phosphorylation and cleavage in association with G2-M phase arrest and apoptosis. *Mol Cancer Ther* 1:841-849.

43. Loo, T. W., and D. M. Clarke. 1998. Superfolding of the partially unfolded core-glycosylated intermediate of human P-glycoprotein into the mature enzyme is promoted by substrate-induced transmembrane domain interactions. *J Biol Chem* 273:14671-14674.

44. Messersmith, W. A., S. D. Baker, L. Lassiter, R. A. Sullivan, K. Dinh, V. I. Almuete, J. J. Wright, R. C. Donehower, M. A. Carducci, and D. K. Armstrong. 2006. Phase I trial of bortezomib in combination with docetaxel in patients with advanced solid tumors. *Clin Cancer Res* 12:1270-1275.

45. Lieu, C., L. Chow, A. S. Pierson, S. G. Eckhardt, C. L. O'Bryant, M. Morrow, Z. V. Tran, J. J. Wright, and L. Gore. 2009. A phase I study of bortezomib, etoposide and carboplatin in patients with advanced solid tumors refractory to standard therapy. *Invest New Drugs* 27:53-62.

46. Ryan, D. P., L. J. Appleman, T. Lynch, J. G. Supko, P. Fidias, J. W. Clark, M. Fishman, A. X. Zhu, P. C. Enzinger, O. Kashala, J. Cusack, Jr., and J. P. Eder. 2006. Phase I clinical trial of bortezomib in combination with gemcitabine in patients with advanced solid tumors. *Cancer* 107:2482-2489.

47. Voortman, J., E. F. Smit, R. Honeywell, B. C. Kuenen, G. J. Peters, H. van de Velde, and G. Giaccone. 2007. A parallel dose-escalation study of weekly and twice-weekly bortezomib in combination with gemcitabine and cisplatin in the first-line treatment of patients with advanced solid tumors. *Clin Cancer Res* 13:3642-3651.

48. Emmenegger, U., G. Francia, Y. Shaked, and R. S. Kerbel. Metronomic chemotherapy: principles and lessons learned from applications in the treatment of metastatic prostate cancer. *Recent Results Cancer Res* 180: 165-183.

49. Mutsaers, A. J. 2009. Metronomic chemotherapy. *Top Companion Anim Med* 24:137-143.

50. Navon, A., and A. Ciechanover. 2009. The 26 S proteasome: from basic mechanisms to drug targeting. *J Biol Chem* 284:33713-33718.

51. Adams, J. 2002. Development of the proteasome inhibitor PS-341. *Oncologist* 7:9-16.

52. Sayers, T. 2008. Productively combining proteasome inhibition with the immunotherapy of cancer. *JMolMed* 86:857-860.

53. Landowski, T. H., C. J. Megli, K. D. Nullmeyer, R. M. Lynch, and R. T. Dorr. 2005. Mitochondrial-mediated disregulation of Ca2+ is a critical determinant of Velcade® (PS-341/bortezomib) cytotoxicity in myeloma cell lines. *Cancer Res* 65:3828-3836.

54. Pei, X. Y., Y. Dai, and S. Grant. 2004. Synergistic induction of oxidative injury and apoptosis in human multiple myeloma cells by the proteasome inhibitor bortezomib and histone deacetylase inhibitors. *Clin Cancer Res* 10:3839-3852.

55. Pineiro-Sanchez, M. L., L. A. Goldstein, J. Dodt, L. Howard, Y. Yeh, H. Tran, W. S. Argraves, and W. T. Chen. 1997. Identification of the 170-kDa melanoma membrane-bound gelatinase (seprase) as a serine integral membrane protease. *J Biol Chem* 272:7595-7601.

56. Rosenblum, J. S., and J. W. Kozarich. 2003. Prolyl peptidases: a serine protease subfamily with high potential for drug discovery. *Curr Opin Chem Biol* 7:496-504.

57. Edosada, C. Y., C. Quan, T. Tran, V. Pham, C. Wiesmann, W. Fairbrother, and B. B. Wolf. 2006. Peptide substrate profiling defines fibroblast activation protein as an endopeptidase of strict Gly(2)-Pro(1)-cleaving specificity. *FEBSLett* 580:1581-1586.
58. Garin-Chesa, P., L. J. Old, and W. J. Rettig. 1990. Cell surface glycoprotein of reactive stromal fibroblasts as a potential antibody target in human epithelial cancers. *Proc Natl Acad Sci USA* 87:7235-7239.
59. Rettig, W. J., P. Garin-Chesa, J. H. Healey, S. L. Su, H. L. Ozer, M. Schwab, A. P. Albino, and L. J. Old. 1993. Regulation and heteromeric structure of the fibroblast activation protein in normal and transformed cells of mesenchymal and neuroectodermal origin. *Cancer Res* 53:3327-3335.
60. Rettig, W. J., P. Garin-Chesa, H. R. Beresford, H. F. Oettgen, M. R. Melamed, and L. J. Old. 1988. Cell-surface glycoproteins of human sarcomas: differential expression in normal and malignant tissues and cultured cells. *Proc NatlAcad Sci USA* 85:3110-3114.
61. Bhowmick, N. A., E. G., Neilson, and H. L. Moses. 2004. Stromal fibroblasts in cancer initiation and progression. *Nature* 432:332-337.
62. Orlowski, R. Z., K. Stewart, M. Vallone, and e. al. 2007. Safety and antitumor efficacy of the proteasome inhibitor carfilzomib (PR-171) dosed for five consecutive days in hematologic malignancies: phase I result [abstract 409]. *Blood* 110: 127a.
63. Alsina, M., S. Trudel, M. Vallone, and e. al. 2007. Phase I single agent antitumor activity of twice weekly-consecutive day dosing of the proteasome inhibitor carfilzomib (PR-171) in hematologic malignancies [abstract 411]. *Blood* 110:128a.
64. Ciechanover, A. 1998. The ubiquitin-proteasome pathway: on protein death and cell life. *EMBO J* 17:7151-7160.
65. Bachovchin, W. W., A. G. Plaut, G. R. Flentke, M. Lynch, and C. A. Kettner. 1990. Inhibition of IgA1 proteinases from *Neisseria gonorrhoeae* and *Hemophilus influenzae* by peptide prolyl boronic acids. *J Biol Chem* 265:3738-3743.
66. Connolly, B. A., D. G. Sanford, A. K. Chiluwal, S. E. Healey, D. E. Peters, M. T. Dimare, W. Wu, Y. Liu, H. Maw, Y. Zhou, Y. Li, Z. Jin, J. L. Sudmeier, J. H. Lai, and W. W. Bachovchin. 2008. Dipeptide boronic acid inhibitors of dipeptidyl peptidase IV: determinants of potency and in vivo efficacy and safety. *J Med Chem* 51:6005-6013.
67. Jackson, E. L., N. Willis, K. Mercer, R. T. Bronson, D. Crowley, R. Montoya, T. Jacks, and D. A. Tuveson. 2001. Analysis of lung tumor initiation and progression using conditional expression of oncogenic K-ras. *Genes Dev* 15:3243-3248.
68. Santos, A. M., J. Jung, N. Aziz, J. L. Kissil, and E. Pure. 2009. Targeting fibroblast activation protein inhibits tumor stromagenesis and growth in mice. *J Clin Invest* 119:3613-3625.
69. Cheng, J. D., M. Valianou, A. A. Canutescu, E. K. Jaffe, H. O. Lee, H. Wang, J. H. Lai, W. W. Bachovchin, and L. M. Weiner. 2005. Abrogation of fibroblast activation protein enzymatic activity attenuates tumor growth. *Mol Cancer Ther* 4:351-360.
70. Niedermeyer, J., M. Kriz, F. Hilberg, P. Garin-Chesa, U. Bamberger, M. C. Lenter, J. Park, B. Viertel, H. Puschner, M. Mauz, W. J. Rettig, and A. Schnapp. 2000. Targeted disruption of mouse fibroblast activation protein. *Mol Cell Biol* 20:1089-1094.
71. Adams, J., V. J. Palombella, E. A. Sausville, J. Johnson, A. Destree, D. D. Lazarus, J. Maas, C. S. Pien, S. Prakash, and P. J. Elliott. 1999. Proteasome inhibitors: a novel class of potent and effective antitumor agents. *Cancer Res* 59:2615-2622.
72. McConkey, D. J., and K. Zhu. 2008. Mechanisms of proteasome inhibitor action and resistance in cancer. *Drug Resist Update* 11:164-179.
73. Dolznig, H., N. Schweifer, C. Purl, N. Kraut, W. J. Rettig, D. Kerjaschki, and P. Garin-Chesa. 2005. Characterization of cancer stroma markers: in silico analysis of an mRNA expression database for fibroblast activation protein and endosialin. *Cancer Immun* 5:10.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

All of the U.S. patents and U.S. patent application publications cited herein are hereby incorporated by reference.

We claim:
1. A method of treating cancer, psoriasis, restenosis, or other cell proliferative disease, comprising administering to a mammal in need thereof a therapeutically effective amount of a fibroblast activation protein (FAP)-activated proteasome inhibitor represented by formula III:

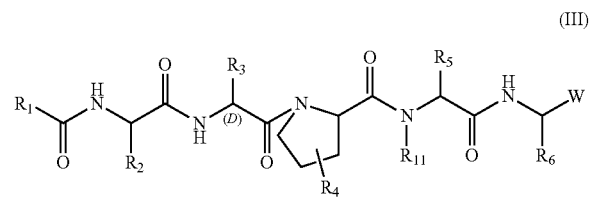

wherein
$R_1$—(C=O)— represents an acyl N-terminal blocking group;
$R_2$ represents H, lower alkyl, or a mono- or di-hydroxy-substituted lower alkyl;
$R_3$ represents lower alkyl;
$R_4$ is absent
$R_5$ represents a hydrophobic amino acid sidechain;
$R_6$ represents alkyl, cycloalkyl, aryl, heterocycle or —(CH$_2$)$_n$—R$_7$;
$R_7$ represents aryl, aralkyl, cycloalkyl, alkoxy, alkylthio, —OH or —SH;
$R_{11}$ represents H or lower alkyl;
W represents

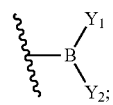

$Y_1$ and $Y_2$ are independently OH, or a group capable of being hydrolyzed to a hydroxyl group; or $Y_1$ and $Y_2$ taken together with the B to which they are attached form a ring having from 5 to 8 atoms in the ring structure; and
n is an integer in the range of 1 to 8.

2. The method of claim 1, wherein the FAP-activated proteasome inhibitor is represented by

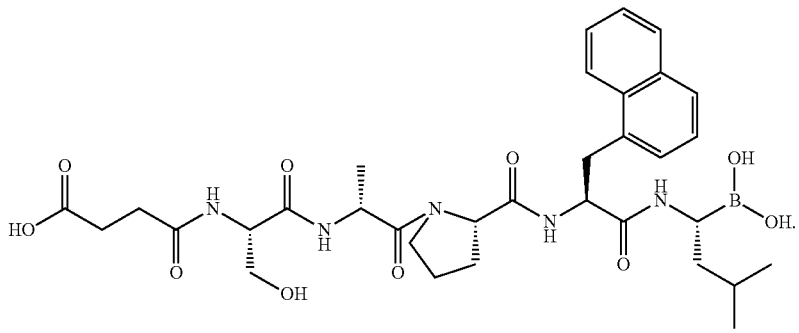 [SMILES: CC(C)C[C@H](NC(=O)[C@H](Cc1cccc2ccccc12)NC(=O)[C@@H]1CCCN1C(=O)[C@@H](C)NC(=O)[C@H](CO)NC(=O)CCC(=O)O)B(O)O]

3. The method of claim 1, wherein the method is a method of treating cancer.

4. The method of claim 3, wherein the cancer is a solid tumor.

5. The method of claim 4, wherein the solid tumor is prostate, pancreatic, or breast cancer.

6. The method of claim 3, wherein the cancer is pancreatic cancer.

7. The method of claim 3, wherein the cancer is multiple myeloma.

8. The method of claim 1, wherein $Y_1$ is OH; and $Y_2$ is OH.

9. The method of claim 2, wherein the method is a method of treating cancer.

10. The method of claim 8, wherein the method is a method of treating cancer.

11. The method of claim 9, wherein the cancer is a solid tumor.

12. The method of claim 11, wherein the solid tumor is prostate, pancreatic, or breast cancer.

13. The method of claim 12, wherein the cancer is pancreatic cancer.

14. The method of claim 9, wherein the cancer is multiple myeloma.

15. The method of claim 10, wherein the cancer is a solid tumor.

16. The method of claim 15, wherein the solid tumor is prostate, pancreatic, or breast cancer.

17. The method of claim 16, wherein the cancer is pancreatic cancer.

18. The method of claim 10, wherein the cancer is multiple myeloma.

* * * * *